United States Patent
Agrawal et al.

(10) Patent No.: US 7,498,425 B2
(45) Date of Patent: Mar. 3, 2009

(54) IMMUNOSTIMULATORY OLIGONUCLEOTIDE MULTIMERS

(75) Inventors: Sudhir Agrawal, Shrewsbury, MA (US); Ekambar Kandimalla, Southboro, MA (US); Dong Yu, Westboro, MA (US)

(73) Assignee: Idera Pharmaceuticals, Inc., Cambridge, MA (US)

( * ) Notice: Subject to any disclaimer, the term of this patent is extended or adjusted under 35 U.S.C. 154(b) by 385 days.

(21) Appl. No.: 11/174,448

(22) Filed: Jul. 1, 2005

(65) Prior Publication Data

US 2006/0025365 A1 Feb. 2, 2006

Related U.S. Application Data

(63) Continuation of application No. 11/153,054, filed on Jun. 15, 2005, and a continuation of application No. 10/892,550, filed on Jul. 15, 2004.

(60) Provisional application No. 60/599,362, filed on Aug. 6, 2004, provisional application No. 60/579,985, filed on Jun. 15, 2004.

(51) Int. Cl.
*C07H 21/02* (2006.01)
*C07H 21/00* (2006.01)
*C07H 19/00* (2006.01)

(52) U.S. Cl. .................... 536/23.1; 536/22.1; 536/24.5; 536/25.6; 514/48; 514/49; 514/52; 514/885; 424/1.11; 424/1.73; 424/1.77; 424/8.81

(58) Field of Classification Search ................ None
See application file for complete search history.

(56) References Cited

U.S. PATENT DOCUMENTS 7,255,868 B2 * 8/2007 Fearon et al. ............ 424/280.1
7,276,489 B2 * 10/2007 Agrawal et al. ............... 514/44

OTHER PUBLICATIONS

Weiner (2000) J. of Leukocyte Biology. 68: 455-463.*
DeGruijl and Curiel (1999) Nature Medicine. 5(10): 1124-1125.*
Donnelly (2003) Nature Medicine. 9(11): 1354-1356.*
Kandimalla et al (2003) PNAS. 100(24): 14303-14308.*
Kandimalla et al (2002) Bioconjugate Chem. 13: 966-974.*

* cited by examiner

*Primary Examiner*—Bruce Campell
*Assistant Examiner*—Michelle Horning
(74) *Attorney, Agent, or Firm*—Keown & Zucchero, LLP; Wayne A. Keown; Joseph C. Zucchero

(57) ABSTRACT

The invention provides an immunostimulatory nucleic acid. In certain embodiments according to this aspect of the invention, the sequence of the immunostimulatory oligonucleotide and/or immunomer is at least partially self-complementary.

7 Claims, 6 Drawing Sheets

Parallel Synthesis of Immunomers

No linker

S, Glycerol brancher,
Short linker

K, Sym. brancher,
Long linker

IMMUNOSTIMULATORY OLIGONUCLEOTIDE MULTIMERS

RELATED APPLICATIONS

This application is a continuation-in-part of U.S. patent application Ser. No. 10/892,550, filed Jul. 15, 2004 and a continuation of U.S. patent application Ser. No. 11/153,054, filed Jun. 15, 2005, which claims the benefit of U.S. Provisional Application Ser. No. 60/579,985, filed Jun. 15, 2004, and U.S. Provisional Application Ser. No. 60/599,362, filed on Aug. 6, 2004. The entire teachings of the above-referenced Applications are incorporated herein by reference.

BACKGROUND OF THE INVENTION

1. Field of the Invention

The invention relates to immune stimulation by oligonucleotide analogs.

2. Summary of the Related Art

Tokunaga et al., J. Natl. Cancer Inst. 72 (1984) 955-96; Pisetsky et al.; Reich et al., Mol. Biol. Rep. 18 (1993) 217-221; Krieg et al., Yi et al., Nature 374 (1995) 546-549 and Sato et al., Science 273 (1996) 352-354 teach that bacterial DNA, synthetic oligodeoxynucleotides, and DNA vaccines containing unmethylated CpG-dinucleotides in specific sequence contexts (CpG DNA) activate the vertebrate immune system.

Krieg et al., Annu. Rev. Immunol. 20 (2002) 709-760; Dalpke et al., Biol. Chem. 383 (2002) 1491-1500 and Kandimalla et al., Curr. Opin. Mol. Ther. 4 (2002) 122-129 teach that CpG DNAs induce innate immune cells to produce Th1 cytokines that promote cytotoxic T lymphocyte (CTL) responses and production of immunoglobulins by B cells. The immunostimulatory properties of CpG DNAs have allowed their use as therapeutic agents for a broad spectrum of disease indications including cancers, viral and bacterial infections, inflammatory disorders and as adjuvant in immunotherapy.

In addition to chemical modifications, a number of structural modifications influenced the activity of CpG DNAs. Kandimalla et al., Nucleic Acids Res. 30 (2002) 4460-4469 teaches that CpG DNAs that contained two freely accessible 5'-ends through a 3'-3'-linkage had greater activity than did conventional CpG DNAs containing multiple copies of CpG motifs and a single 5'-end.

Kandimalla et al, Biochem. Biophys. Res. Commun. 306 (2003) 948-953 teaches that the presence of a secondary structure in CpG DNAs significantly affected their activity depending on the position and nature of the secondary structure, that the presence of a hairpin structure at the 5'-end abrogated stimulatory activity, and that the same structure at the 3'-end had an insignificant effect on stimulatory activity but caused lower IL-6 secretion and contributed to higher stability against nucleases.

There remains a need to "customize" the immune response through modification of oligonucleotide analogs.

BRIEF SUMMARY OF THE INVENTION

In a first aspect the invention provides an immunostimulatory oligonucleotide the sequence of which is at least partially self-complementary. The immunostimulatory nucleic acid comprises an oligonucleotide sequence containing at least one dinucleotide selected from the group consisting of CpG, C*pG, C*pG* and CpG*, wherein C is cytidine or 2'-deoxycytidine, G is guanosine or 2'-deoxyguanosine, C* is 2'-deoxythymidine, 1-(2'-deoxy-β-D-ribofuranosyl)-2-oxo-7-deaza-8-methyl-purine, 2'-dideoxy-5-halocytosine, 2'-dideoxy-5-nitrocytosine, arabinocytidine, 2'-deoxy-2'-substituted arabinocytidine, 2'-O-substituted arabinocytidine, 2'-deoxy-5-hydroxycytidine, 2'-deoxy-N4-alkyl-cytidine, 2'-deoxy-4-thiouridine, or other pyrimidine nucleoside analogs, G* is 2'-deoxy-7-deazaguanosine, 2'-deoxy-6-thioguanosine, arabinoguanosine, 2'-deoxy-2'substituted-arabinoguanosine, 2'-O-substituted-arabinoguanosine, 2'-deoxyinosine, or other purine nucleoside analogs, and p is an internucleoside linkage selected from the group consisting of phosphodiester, phosphorothioate, and phosphorodithioate.

In some embodiments, the immunostimulatory nucleic acid is from about 2 to about 50 nucleotides in length. In certain embodiments the immunostimulatory nucleic acid is from about 12 to about 26 nucleotides in length. In some embodiments, the oligonucleotides each have from about 3 to about 35 nucleoside residues, in further embodiments from about 4 to about 30 nucleoside residues, in even further embodiments from about 4 to about 20 nucleoside residues. In some embodiments, the oligonucleotides have from about 5 to about 18, or from about 5 to about 14, nucleoside residues. As used herein, the term "about" implies that the exact number is not critical. Thus, the number of nucleoside residues in the oligonucleotides is not critical, and oligonucleotides having one or two fewer nucleoside residues, or from one to several additional nucleoside residues are contemplated as equivalents of each of the embodiments described above. In some embodiments, one or more of the oligonucleotides have 11 nucleotides.

In a second aspect the invention provides an immunomer comprising at least two oligonucleotides linked by a non-nucleotide linker, wherein the sequences of the immunostimulatory oligonucleotides are at least partially self-complementary. In certain embodiments according to this aspect of the invention at least one of the oligonucleotides contains at least one dinucleotide selected from the group consisting of CpG, C*pG, C*pG* and CpG*, wherein C is cytidine or 2'-deoxycytidine, G is guanosine or 2'-deoxyguanosine, C* is 2'-deoxythymidine, 1-(2'-deoxy-β-D-ribofuranosyl)-2-oxo-7-deaza-8-methyl-purine, 2'-dideoxy-5-halocytosine, 2'-dideoxy-5-nitrocytosine, arabinocytidine, 2'-deoxy-2'-substituted arabinocytidine, 2'-O-substituted arabinocytidine, 2'-deoxy-5-hydroxycytidine, 2'-deoxy-N4-alkyl-cytidine, 2'-deoxy-4-thiouridine, or other pyrimidine nucleoside analogs, G* is 2'-deoxy-7-deazaguanosine, 2'-deoxy-6-thioguanosine, arabinoguanosine, 2'-deoxy-2'substituted-arabinoguanosine, 2'-O-substituted-arabinoguanosine, 2'-deoxyinosine, or other purine nucleoside analogs, and p is an internucleoside linkage selected from the group consisting of phosphodiester, phosphorothioate, and phosphorodithioate.

In some embodiments, the immunostimulatory nucleic acid is from about 2 to about 50 nucleotides in length. In certain embodiments the immunostimulatory nucleic acid is from about 12 to about 26 nucleotides in length. In some embodiments, the oligonucleotides each have from about 3 to about 35 nucleoside residues, or from about 4 to about 30 nucleoside residues, or from about 4 to about 20 nucleoside residues. In some embodiments, the oligonucleotides have from about 5 to about 18, or from about 5 to about 14, nucleoside residues. As used herein, the term "about" implies that the exact number is not critical. Thus, the number of nucleoside residues in the oligonucleotides is not critical, and oligonucleotides having one or two fewer nucleoside residues, or from one to several additional nucleoside residues are contemplated as equivalents of each of the embodiments described above. In some embodiments, one or more of the oligonucleotides have 11 nucleotides.

In a third aspect the invention provides pharmaceutical compositions. These compositions comprise any one of the compositions disclosed in the first and second aspects of the invention either alone or in combination and a pharmaceutically acceptable carrier.

In a fourth aspect the invention provides a method for generating an immune response in a vertebrate. This method comprises administering to the vertebrate any one of the compositions, alone or in combination, disclosed in the first, second and third aspects of the invention. The compositions disclosed herein can be administered through any suitable route of administration including, but not limited to, parenteral, oral, sublingual, transdermal, topical, intranasal, aerosol, intraocular, intratracheal, intrarectal, vaginal, gene gun, dermal patch, eye drop and mouthwash.

In a fifth aspect the invention provides a method for therapeutically treating a vertebrate having cancer, an autoimmune disorder, airway inflammation, inflammatory disorders, skin disorders, allergy, asthma or a disease caused by a pathogen. This method comprises administering to the vertebrate any one of the compositions, alone or in combination, disclosed in the first, second and third aspects of the invention. The compositions disclosed herein can be administered through any suitable route of administration including, but not limited to, parenteral, oral, sublingual, transdermal, topical, intranasal, aerosol, intraocular, intratracheal, intrarectal, vaginal, gene gun, dermal patch, eye drop, ear drop and mouthwash.

In a sixth aspect the invention provides a method for preventing cancer, an autoimmune disorder, airway inflammation, inflammatory disorders, skin disorders, allergy, asthma or a disease caused by a pathogen in a vertebrate. This method comprises administering to the vertebrate any one of the compositions, alone or in combination, disclosed in the first, second and third aspects of the invention. The compositions disclosed herein can be administered through any suitable route of administration including, but not limited to, parenteral, oral, sublingual, transdermal, topical, intranasal, aerosol, intraocular, intratracheal, intrarectal, vaginal, gene gun, dermal patch, eye drop, ear drop and mouthwash.

BRIEF DESCRIPTION OF THE DRAWINGS

In FIG. 1B, m and n are independently 0-1000.

DETAILED DESCRIPTION OF THE PREFERRED EMBODIMENTS

Figure 1A:
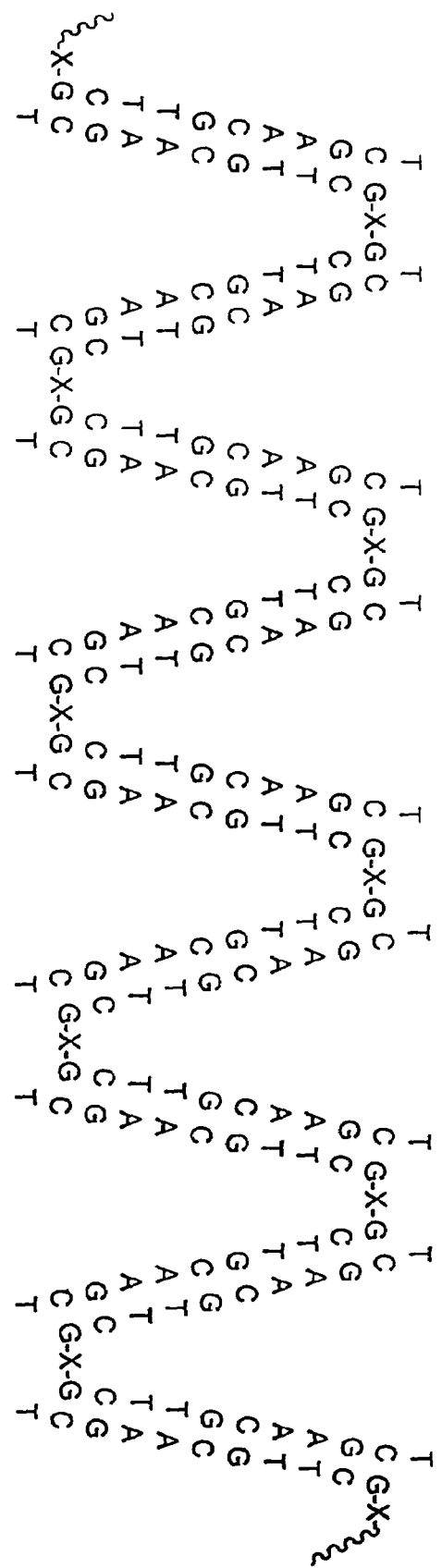
FIGS. 1A and 1B are representations of various embodiments of the invention (SEQ ID NO: 41).

The issued patents, patent applications, and references that are cited herein are hereby incorporated by reference to the same extent as if each was specifically and individually indicated to be incorporated by reference. In the event of inconsistencies between any teaching of any reference cited herein and the present specification, the latter shall prevail for purposes of the invention.

The invention relates to the therapeutic use of oligonucleotides as immunostimulatory agents for immunotherapy applications. The invention also provides methods for generating, enhancing and modifying the immune response caused by immunostimulatory compounds used for immunotherapy applications such as, but not limited to, treatment and/or prevention of cancer, autoimmune disorders, asthma, respiratory allergies, food allergies, and bacteria, parasitic, and viral infections in adult and pediatric human and veterinary applications. Allergic asthma is a certain embodied condition for treatment by the present methods and compounds. Thus, the invention further provides compounds having optimal levels of immunostimulatory effect for immunotherapy and methods for making and using such compounds. In addition, immunostimulatory oligonucleotides/immunomers of the invention are useful as adjuvants in combination with DNA vaccines, antibodies, allergens, chemotherapeutic agents, and antisense oligonucleotides.

In a first aspect the invention provides an immunostimulatory oligonucleotide the sequence of which is at least partially self-complementary. The immunostimulatory nucleic acid comprises a nucleic acid sequence containing at least one dinucleotide selected from the group consisting of CpG, C*pG, C*pG* and CpG*, wherein C is cytidine or 2'-deoxycytidine, G is guanosine or 2'-deoxyguanosine, C* is 2'-deoxythymidine, 1-(2'-deoxy-β-D-ribofuranosyl)-2-oxo-7-deaza-8-methyl-purine, 2'-dideoxy-5-halocytosine, 2'-dideoxy-5-nitrocytosine, arabinocytidine, 2'-deoxy-2'-substituted arabinocytidine, 2'-O-substituted arabinocytidine, 2'-deoxy-5-hydroxycytidine, 2'-deoxy-N4-alkyl -cytidine, 2'-deoxy-4-thiouridine, or other pyrimidine nucleoside analogs, G* is 2'-deoxy-7-deazaguanosine, 2'-deoxy-6-thioguanosine, arabinoguanosine, 2'-deoxy-2'substituted-arabinoguanosine, 2'-O-substituted-arabinoguanosine, 2'-deoxyinosine, or other purine nucleoside analogs, and p is an internucleoside linkage selected from the group consisting of phosphodiester, phosphorothioate, and phosphorodithioate.

In some embodiments, the immunostimulatory oligonucleotide is from about 2 to about 50 nucleotides in length. In certain embodiments the immunostimulatory oligonucleotide is from about 12 to about 26 nucleotides in length. In some embodiments, the oligonucleotides are from about 3 to about 35 nucleoside residues, or from about 4 to about 30 nucleoside residues, or from about 4 to about 20 nucleoside residues. In some embodiments, the oligonucleotides have from about 5 to about 18, or from about 5 to about 14, nucleoside residues. As used herein, the term "about" implies that the exact number is not critical. Thus, the number of nucleoside residues in the oligonucleotides is not critical, and oligonucleotides having one or two fewer nucleoside residues, or from one to several additional nucleoside residues are contemplated as equivalents of each of the embodiments described above. In some embodiments, one or more of the oligonucleotides have 11 nucleotides.

As would be recognized by one skilled in the art, the complementary sequence of the oligonucleotides allows for intermolecular hydrogen bonding thereby giving the oligonucleotides secondary structure. Additional oligonucleotides can bind together thereby creating a chain, or multimers, of oligonucleotides according to the invention.

In a second aspect the invention provides an immunomer comprising at least two oligonucleotides linked by a non-nucleotide linker, wherein the sequences of the immunostimulatory oligonucleotides are at least partially self-complementary. In certain embodiments according to this aspect of the invention at least one of the oligonucleotides contains at least one dinucleotide selected from the group consisting of CpG, C*pG, C*pG* and CpG*, wherein C is cytidine or 2'-deoxycytidine, G is guanosine or 2'-deoxyguanosine, C* is 2'-deoxythymidine, 1-(2'-deoxy-β-D-ribofuranosyl)-2-oxo-7-deaza-8-methyl-purine, 2'-dideoxy-5-halocytosine, 2'-dideoxy-5-nitrocytosine, arabinocytidine, 2'-deoxy-2'-substituted arabinocytidine, 2'-O-substituted arabinocytidine, 2'-deoxy-5-hydroxycytidine, 2'-deoxy-N4-alkyl-cytidine, 2'-deoxy4-thiouridine, or other pyrimidine nucleoside analogs, G* is 2'-deoxy-7-deazaguanosine, 2'-deoxy-6-thioguanosine, arabinoguanosine, 2'-deoxy-2'substituted-arabinoguanosine, 2'-O-substituted-arabinoguanosine, 2'-deoxyinosine, or other purine nucleoside analogs, and p is an internucleoside linkage selected from the group consisting of phosphodiester, phosphorothioate, and phosphorodithioate.

In this aspect, immunostimulatory nucleic acid comprises a structure as detailed in formula (I).

Domain A-Domain B-Domain C        (I)

Domains may be from about 2 to about 12 nucleotides in length. Domain A may be 5'-3' or 3'-5' or 2'-5' DNA, RNA, RNA-DNA, DNA-RNA having a palindromic or self-complementary domain containing or not containing at least one dinucleotide selected from the group consisting of CpG, C*pG, C*pG* and CpG*, wherein C is cytidine or 2'-deoxycytidine, G is guanosine or 2'-deoxyguanosine, C* is 2'-deoxythymidine, 1-(2'-deoxy-β-D-ribofuranosyl)-2-oxo-7-deaza-8-methyl-purine, 2'-deoxy-5-halocytosine, 2'-deoxy-5-nitrocytosine, arabinocytidine, 2'-deoxy-2'-substituted arabinocytidine, 2'-O-substituted arabinocytidine, 2'-deoxy-5-hydroxycytidine, 2'-deoxy-N4-alkyl-cytidine, 2'-deoxy-4-thiouridine, or other pyrimidine nucleoside analogs, G* is 2'-deoxy-7-deazaguanosine, 2'-deoxy-6-thioguanosine, arabinoguanosine, 2'-deoxy-2'substituted-arabinoguanosine, 2'-O-substituted-arabinoguanosine, 2'-deoxyinosine, or other purine nucleoside analogs, and p is an internucleoside linkage selected from the group consisting of phosphodiester, phosphorothioate, and phosphorodithioate. In certain embodiments, the immunostimulatory dinucleotide is not CpG.

In certain embodiments, Domain A will have more than one dinucleotide selected from the group consisting of CpG, C*pG, C*pG* and CpG*.

Domain B, as depicted by an "X" below, is a linker joining Domains A and C that may be a 3'-'5' linkage, a 2'-5' linkage, a 3'-3' linkage, a phosphate group, a nucleoside, or a non-nucleoside linker that may be aliphatic, aromatic, aryl, cyclic, chiral, achiral, a peptide, a carbohydrate, a lipid, a fatty acid, mono- tri- or hexapolyethylene glycol, or a heterocyclic moiety.

Domain C may be 5'-3' or 3'-5', 2'-5' DNA, RNA, RNA-DNA, DNA-RNA Poly I-Poly C having a palindromic or self-complementary sequence, containing or not containing a dinucleotide selected from the group consisting of CpG, C*pG, C*pG*, CpG*, wherein C is cytidine or 2'-deoxycytidine, G is guanosine or 2'-deoxyguanosine, C* is 2'-deoxythymidine, 1-(2'-deoxy-β-D-ribofuranosyl)-2-oxo-7-deaza-8-methyl-purine, 2'-deoxy-5-halocytosine, 2'-dideoxy-5-nitrocytosine, arabinocytidine, 2'-deoxy-2'-substituted arabinocytidine, 2'-O-substituted arabinocytidine, 2'-deoxy-5-hydroxycytidine, 2'-deoxy-N4-alkyl -cytidine, 2'-deoxy-4-thiouridine, other pyrimidine nucleoside analogs, G* is 2'-deoxy-7-deazaguanosine, 2'-deoxy-6-thioguanosine, arabinoguanosine, 2'-deoxy-2'substituted-arabinoguanosine, 2'-O-substituted-arabinoguanosine, 2'-deoxyinosine, or other purine nucleoside analogs, and p is an internucleoside linkage selected from the group consisting of phosphodiester, phosphorothioate, and phosphorodithioate. In certain embodiments, the immunostimulatory dinucleotide is not CpG. In some embodiments, Domain B is preferably a non-nucleotidic linker connecting oligonucleotides of Domain A and Domain C, which are referred to as "immunomers." In certain embodiments, Domain C does not have the dinucleotide CpG, C*pG, C*pG* or CpG*.

In some embodiments, the oligonucleotides contained in formula (I) are from about 2 to about 50 nucleotides in length. In certain embodiments the oligonucleotides contained in formula (I) are from about 12 to about 26 nucleotides in length. In some embodiments, the oligonucleotides each have from about 3 to about 35 nucleoside residues, preferably from about 4 to about 30 nucleoside residues, more preferably from about 4 to about 20 nucleoside residues. In some embodiments, the oligonucleotides have from about 5 to about 18, or from about 5 to about 14, nucleoside residues. As used herein, the term "about" implies that the exact number is not critical. Thus, the number of nucleoside residues in the oligonucleotides is not critical, and oligonucleotides having one or two fewer nucleoside residues, or from one to several additional nucleoside residues are contemplated as equivalents of each of the embodiments described above. In some embodiments, one or more of the oligonucleotides have 11 nucleotides.

A self-complementary sequence as used herein refers to a base sequence which, upon suitable alignment, may form intramolecular or, more typically, intermolecular base pairing between G-C, A-T, A-U and/or G-U wobble pairs. In one embodiment the extent of self-complementarity is at least 50 percent. For example an 8-mer that is at least 50 percent self-complementary may have a sequence capable of forming 4, 5, 6, 7, or 8 G-C, A-T, A-U and/or G-U wobble basepairs. Such basepairs may but need not necessarily involve bases located at either end of the self-complementary immunostimulatory oligonucleotide and/or immunomer. Where nucleic acid stabilization may be important to the immunostimulatory oligonucleotide and/or immunomer, it may be advantageous to "clamp" together one or both ends of a double-stranded nucleic acid, either by basepairing or by any other suitable means. The degree of self-complementarity may depend on the alignment between immunostimulatory oligonucleotide and/or' immunomer, and such alignment may or may not include single- or multiple-nucleoside overhangs. In other embodiments, the degree of self-complementarity is at least 60 percent, at least 70 percent, at least 80 percent, at least 90 percent, or even 100 percent.

Similar considerations apply to intermolecular basepairing between immunostimulatory oligonucleotides and/or immunomers of different base sequence. Thus, where a plurality of immunostimulatory oligonucleotides and/or immunomers are used together, the plurality of immunostimulatory oligonucleotides and/or immunomers may, but need not, include sequences which are at least partially complementary to one another. In one embodiment the plurality of immunostimulatory oligonucleotides and/or immunomers includes an immunostimulatory oligonucleotide and/or immunomer having a first sequence and an immunostimulatory oligonucleotide and/or immunomer having a second sequence, wherein the first sequence and the second sequence are at least 50 percent complementary. For example, as between two 8-mers that are at least 50 percent complementary, they may form 4, 5, 6, 7, or 8 G-C, A-T, A-U, and/or G-U wobble basepairs. Such basepairs may but need not necessarily involve bases located at either end of the complementary immunostimulatory oligonucleotides and/or immunomers. The degree of complementarity may depend on the alignment between immunostimulatory oligonucleotides and/or immunomers, and such alignment may or may not include single- or multiple-nucleoside overhangs. In other embodiments, the degree of complementarity is at least 60 percent, at least 70 percent, at least 80 percent, at least 90 percent, or even 100 percent.

By way of non-limiting example, in certain embodiments of this aspect the immunostimulatory nucleic acid will have a structure as detailed in formula (II).

(II)

Figure 1B:
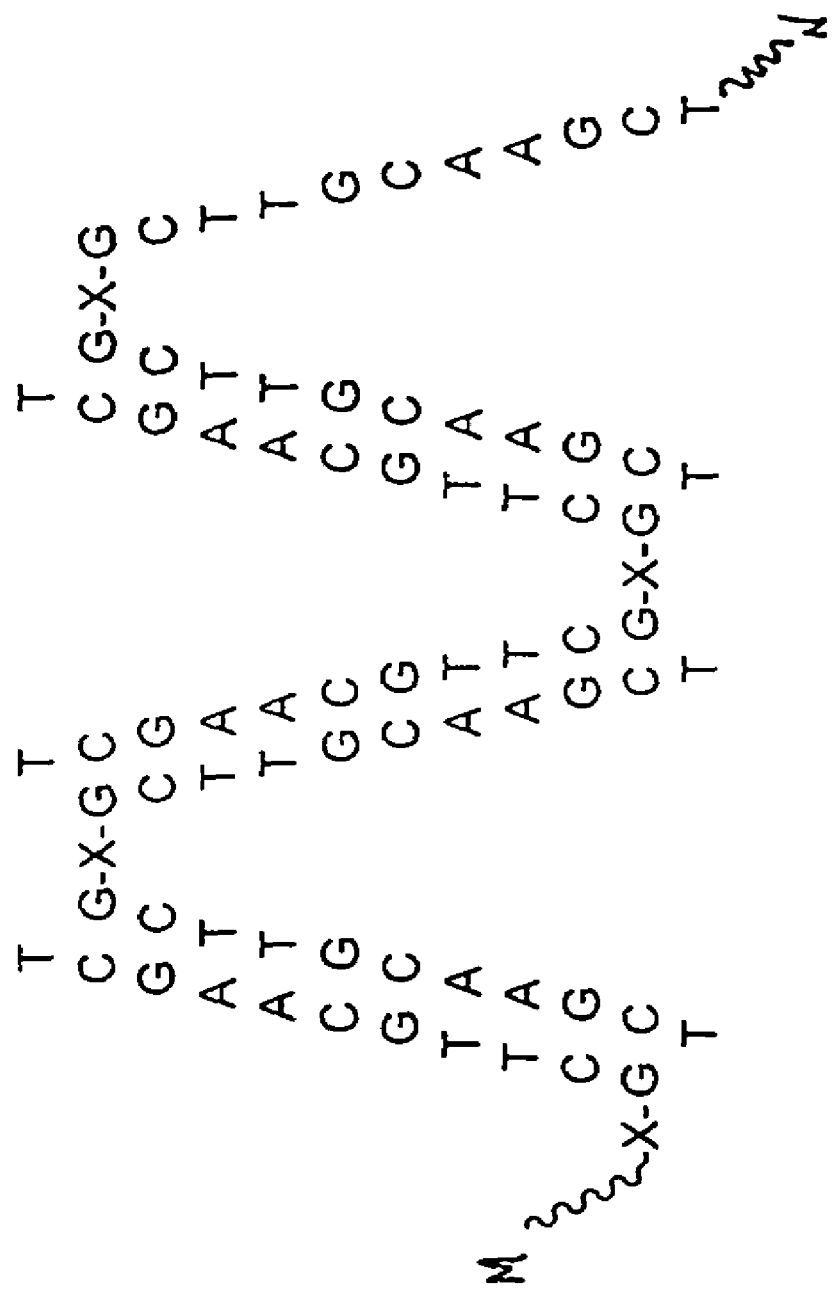

As would be recognized by one skilled in the art, the depicted immunostimulatory nucleic acid/immunomer compounds have secondary structure because the sequences of the domains are complementary allowing for intermolecular hydrogen bonding. Domains A and A' may or may not be identical, domains A and C may or may not be identical, domains A and C' may or may not be identical, domains A' and C may or may not be identical, domains A' and C' may or may not be identical, domains B and B' may or may not be identical and domains C and C' may or may not be identical. Moreover, as shown in FIG. 1, additional immunomers can bind through intermolecular hydrogen bonding thereby creating a chain, or multimers, of immunomers according to the invention. n can be any number of continuous, self complementary immunomer compounds.

As used herein, the term "complementary" means having the ability to hybridize to a nucleic acid. Such hybridization is ordinarily the result of hydrogen bonding between complementary strands, preferably to form Watson-Crick or Hoogsteen base pairs, although other modes of hydrogen bonding, as well as base stacking can also lead to hybridization.

As used herein, the term "secondary structure" refers to intermolecular hydrogen bonding. Intermolecular hydrogen bonding results in the formation of a duplexed nucleic acid molecule.

"Palindromic sequence" shall mean an inverted repeat (i.e., a sequence such as ABCDEE'D'C'B'A' in which A and A', B and B', etc., are bases capable of forming the usual Watson-Crick base pairs. In vivo, such sequences may form double-stranded structures. In one embodiment the CpG nucleic acid contains a palindromic sequence. A palindromic sequence used in this context refers to a palindrome in which the CpG is part of the palindrome. In some embodiments the CpG is the center of the palindrome. In another embodiment the CpG nucleic acid is free of a palindrome. An immunostimulatory nucleic acid that is free of a palindrome is one in which the CpG dinucleotide is not part of a palindrome. Such an oligonucleotide may include a palindrome in which the CpG is not the center of the palindrome.

For purposes of the invention, the term "oligonucleotide" refers to a polynucleoside formed from a plurality of linked nucleoside units. Such oligonucleotides can be obtained from existing nucleic acid sources, including genomic or cDNA, but are preferably produced by synthetic methods. In some embodiments each nucleoside unit includes a heterocyclic base and a pentofuranosyl, 2'-deoxypentfuranosyl, trehalose, arabinose, 2'-deoxy-2'-substituted arabinose, 2'-O-substituted arabinose or hexose sugar group. The nucleoside residues can be coupled to each other by any of the numerous known internucleoside linkages. Such internucleoside linkages include, without limitation, phosphodiester, phosphorothioate, phosphorodithioate, alkylphosphonate, alkylphosphonothioate, phosphotriester, phosphoramidate, siloxane, carbonate, carboalkoxy, acetamidate, carbamate, morpholino, borano, thioether, bridged phosphoramidate, bridged methylene phosphonate, bridged phosphorothioate, and sulfone internucleoside linkages. The term "oligonucleotide" also encompasses polynucleosides having one or more stereospecific internucleoside linkage (e.g., (RP)- or (SP)-phosphorothioate, alkylphosphonate, or phosphotriester linkages). As used herein, the terms "oligonucleotide" and "dinucleotide" are expressly intended to include polynucleosides and dinucleosides having any such internucleoside linkage, whether or not the linkage comprises a phosphate group. In certain embodiments, these internucleoside linkages may be phosphodiester, phosphorothioate, or phosphorodithioate linkages, or combinations thereof.

The term "oligonucleotide" also encompasses polynucleosides having additional substituents including, without limitation, protein groups, lipophilic groups, intercalating agents, diamines, folic acid, cholesterol and adamantane. The term "oligonucleotide" also encompasses any other nucleobase containing polymer, including, without limitation, peptide nucleic acids (PNA), peptide nucleic acids with phosphate groups (PHONA), locked nucleic acids (LNA), morpholino-backbone oligonucleotides, and oligonucleotides having backbone sections with alkyl linkers or amino linkers.

The oligonucleotides of the invention can include naturally occurring nucleosides, modified nucleosides, or mixtures thereof. As used herein, the term "modified nucleoside" is a nucleoside that includes a modified heterocyclic base, a modified sugar moiety, or a combination thereof. In some embodiments, the modified nucleoside is a non-natural pyrimidine or purine nucleoside, as herein described. In some embodiments, the modified nucleoside is a 2'-substituted ribonucleoside an arabinonucleoside or a 2'-deoxy-2'-substituted-arabinoside.

For purposes of the invention, the term "2'-substituted ribonucleoside" or "2'-substituted arabinoside" includes ribonucleosides or arabinonucleosides in which the hydroxyl group at the 2' position of the pentose moiety is substituted to produce a 2'-substituted or 2'-O-substituted ribonucleoside. In certain embodiments, such substitution is with a lower alkyl group containing 1-6 saturated or unsaturated carbon atoms, or with an aryl group having 6-10 carbon atoms, wherein such alkyl, or aryl group may be unsubstituted or may be substituted, e.g., with halo, hydroxy, trifluoromethyl, cyano, nitro, acyl, acyloxy, alkoxy, carboxyl, carboalkoxy, or amino groups. Examples of 2'-O-substituted ribonucleosides or 2'-O-substituted -arabinosides include, without limitation 2'-O-methylribonucleosides or 2'-O-methylarabinosides and 2'-O-methoxyethoxyribonucleosides or 2'-O-methoxyethoxyarabinosides.

The term "2'-substituted ribonucleoside" or "2'-substituted arabinoside" also includes ribonucleosides or arabinonucleosides in which the 2'-hydroxyl group is replaced with a lower alkyl group containing 1-6 saturated or unsaturated carbon atoms, or with an amino or halo group. Examples of such 2'-substituted ribonucleosides or 2'-substituted arabinosides include, without limitation, 2'-amino, 2'-fluoro, 2'-allyl, and 2'-propargyl ribonucleosides or arabinosides.

The term "oligonucleotide" includes hybrid and chimeric oligonucleotides. A "chimeric oligonucleotide" is an oligonucleotide having more than one type of internucleoside linkage. One non-limiting example of such a chimeric oligonucleotide is a chimeric oligonucleotide comprising a phosphorothioate, phosphodiester or phosphorodithioate region and non-ionic linkages such as alkylphosphonate or alkylphosphonothioate linkages (see e.g., Pederson et al. U.S. Pat. Nos. 5,635,377 and 5,366,878).

A "hybrid oligonucleotide" is an oligonucleotide having more than one type of nucleoside. One non-limiting example of such a hybrid oligonucleotide comprises a ribonucleotide or 2' substituted ribonucleotide region, and a deoxyribonucleotide region (see, e.g., Metelev and Agrawal, U.S. Pat. Nos. 5,652,355, 6,346,614 and 6,143,881).

Alternatively, the nucleic acid molecule of the invention can be two immunomers linked by way of a non-nucleotidic linker.

In certain embodiments of the invention, at least one immunostimulatory oligonucleotide of the invention comprises an immunostimulatory dinucleotide of the formula 5'-Pyr-Pur-3', wherein Pyr is a natural pyrimidine nucleoside or analog thereof and Pur is a natural purine nucleoside or analog thereof. As used herein, the term "pyrimidine nucleoside" refers to a nucleoside wherein the base component of the nucleoside is a pyrimidine base. Similarly, the term "purine nucleoside" refers to a nucleoside wherein the base component of the nucleoside is a purine base. For purposes of the invention, a "synthetic" pyrimidine or purine nucleoside includes a non-naturally occurring pyrimidine or purine base, a non-naturally occurring sugar moiety, or a combination thereof.

In certain embodiments pyrimidine nucleosides in the immunostimulatory oligonucleotides and/or immunomers used in the method according to the invention have the structure (III):

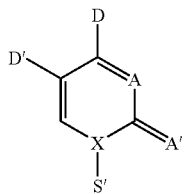

(III)

wherein:
D is a hydrogen bond donor;
D' is selected from the group consisting of hydrogen, hydrogen bond donor, hydrogen bond acceptor, hydrophilic group, hydrophobic group, electron withdrawing group and electron donating group;
A is a hydrogen bond acceptor or a hydrophilic group;
A' is selected from the group consisting of hydrogen bond acceptor, hydrophilic group, hydrophobic group, electron withdrawing group and electron donating group;
X is carbon or nitrogen; and
S' is a pentose or hexose sugar ring, or a non-naturally occurring sugar.

In certain embodiments, the sugar ring is derivatized with a phosphate moiety, modified phosphate moiety, or other linker moiety suitable for linking the pyrimidine nucleoside to another nucleoside or nucleoside analog.

In some embodiments hydrogen bond donors include, without limitation, —NH—, —NH$_2$, —SH and —OH. Preferred hydrogen bond acceptors include, without limitation, C=O, C=S, and the ring nitrogen atoms of an aromatic heterocycle, e.g., N3 of cytosine.

In some embodiments, the base moiety in (III) is a non-naturally occurring pyrimidine base. Examples of preferred non-naturally occurring pyrimidine bases include, without limitation, 5-hydroxycytosine, 5-hydroxymethylcytosine, N4-alkylcytosine, or N4-ethylcytosine, and 4-thiouracil. In some embodiments, the sugar moiety S' in (III) is a non-naturally occurring sugar moiety. For purposes of the present invention, a "naturally occurring sugar moiety" is a sugar moiety that occurs naturally as part of nucleic acid, e.g., ribose and 2'-deoxyribose, and a "non-naturally occurring sugar moiety" is any sugar that does not occur naturally as part of a nucleic acid, but which can be used in the backbone for an oligonucleotide, e.g, hexose. Arabinose and arabinose derivatives are non-limiting examples of sugar moieties.

In some embodiments purine nucleoside analogs in immunostimulatory oligonucleotides and/or immunomers used in the method according to the invention have the structure (IV):

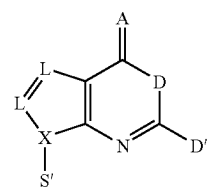

(IV)

wherein:
D is a hydrogen bond donor;
D' is selected from the group consisting of hydrogen, hydrogen bond donor, and hydrophilic group;
A is a hydrogen bond acceptor or a hydrophilic group;
X is carbon or nitrogen;
each L is independently selected from the group consisting of C, O, N and S; and
S' is a pentose or hexose sugar ring, or a non-naturally occurring sugar.

In certain embodiments, the sugar ring is derivatized with a phosphate moiety, modified phosphate moiety, or other linker moiety suitable for linking the pyrimidine nucleoside to another nucleoside or nucleoside analog.

In certain embodiments hydrogen bond donors include, without limitation, —NH—, —NH$_2$, —SH and —OH. Preferred hydrogen bond acceptors include, without limitation, C=O, C=S, —NO$_2$ and the ring nitrogen atoms of an aromatic heterocycle, e.g., N1 of guanine.

In some embodiments, the base moiety in (IV) is a non-naturally occurring purine base. Examples of preferred non-naturally occurring purine bases include, without limitation, 6-thioguanine and 7-deazaguanine. In some embodiments, the sugar moiety S' in (IV) is a naturally occurring sugar moiety, as described above for structure (III).

In a third aspect the invention provides pharmaceutical compositions. These compositions comprise any one of the compositions disclosed in the first and second of the invention either alone or in combination and a pharmaceutically acceptable carrier.

As used herein, the term "physiologically acceptable" refers to a material that does not interfere with the effectiveness of the compositions of the first, second or third aspects of the invention and is compatible with a biological system such as a cell, cell culture, tissue, or organism. In certain embodiments, the biological system is a living organism, such as a vertebrate.

As used herein, the term "carrier" encompasses any excipient, diluent, filler, salt, buffer, stabilizer, solubilizer, lipid, or other material well known in the art for use in pharmaceutical formulations. It will be understood that the characteristics of the carrier, excipient, or diluent will depend on the route of administration for a particular application. The preparation of pharmaceutically acceptable formulations containing these materials is described in, e.g., Remington's Pharmaceutical Sciences, 18th Edition, ed. A. Gennaro, Mack Publishing Co., Easton, Pa., 1990, ISBN: 0-912734-04-3.

Pharmaceutical compositions of the invention may also include a cancer vaccine, including a cancer vaccine selected from EFG, Anti-idiotypic cancer vaccines, Gp75 antigen, GMK melanoma vaccine, MGV ganglioside conjugate vaccine, Her2/new, Ovarex®, M-Vax, O-Vax, L-Vax, STn-KHL Theratope®, BLP25 (MUC-1), liposomal idiotypic vaccine, Melacine®, peptide antigen vaccines, toxin/antigen vaccines, MVA-vased vaccine, PACIS, BCG vaccine, TA-HPV, TA-CIN, DISC-virus and ImmunCyst/TheraCys®.

In various embodiments of the invention, the compositions of the first, second or third aspects of the invention may be covalently linked to an antigen or otherwise operatively associated with an antigen. As used herein, the term "operatively associated with" refers to any association that maintains the activity of both the compositions of the first, second or third aspects of the invention and the antigen. Non-limiting examples of such operative associations include being part of the same liposome or other such delivery vehicle or reagent. In embodiments wherein the compositions of the first, second or third aspects of the invention are covalently linked to an antigen, such covalent linkage is at any position on the compositions of the first, second or third aspects of the invention other than an accessible 5' end of an immunostimulatory oligonucleotide. For example, the antigen may be attached at an internucleoside linkage or may be attached to the non-nucleotidic linker. Alternatively, the antigen may itself be the non-nucleotidic linker.

In various embodiments of the invention, the compositions of the first, second or third aspects of the invention may include an oligonucleotide with antisense activity. As used herein, "antisense activity" means that the oligonucleotide, when introduced into a cell or an animal, causes a reduction in the expression of the gene to which it is complementary.

In various embodiments of the invention, the compositions of the first, second or third aspects of the invention may include an oligonucleotide sequence that is an aptamer. Aptamers are nucleic acid molecules that have been selected from random pools based on their ability to bind other molecules. Aptamers have been selected which bind nucleic acids, proteins, small organic compounds, and even entire organisms. These novel molecules have many potential uses in medicine and technology (see, e.g., Burgstaller P., et al. *Curr Opin Drug Discov Devel.* 5: 690-700 (2002)).

The pharmaceutical compositions of the invention may be administered by any suitable route, including, without limitation, parenteral, oral, sublingual, transdermal, topical, intranasal, aerosol, intraocular, intratracheal, intrarectal, vaginal, by gene gun, dermal patch or in eye drop or mouthwash form. The pharmaceutical compositions can be delivered using known procedures at dosages and for periods of time effective obtain the desired effect, e.g. the treatment of cancer, the treatment of infection and the treatment of autoimmune diseases. When administered systemically, the pharmaceutical compositions are administered at a sufficient dosage to attain a blood level of the compositions of the first, second and/or third aspects of the invention from about 0.0001 micromolar to about 10 micromolar. For localized administration, much lower concentrations than this may be effective, and much higher concentrations may be tolerated. In certain embodiments, a total dosage of immunostimulatory oligonucleotide and/or immunomer ranges from about 0.0001 mg per patient per day to about 200 mg per kg body weight per day. It may be desirable to administer simultaneously, or sequentially a therapeutically effective amount of one or more of the therapeutic compositions of the invention to an individual as a single treatment episode.

Figure 2:
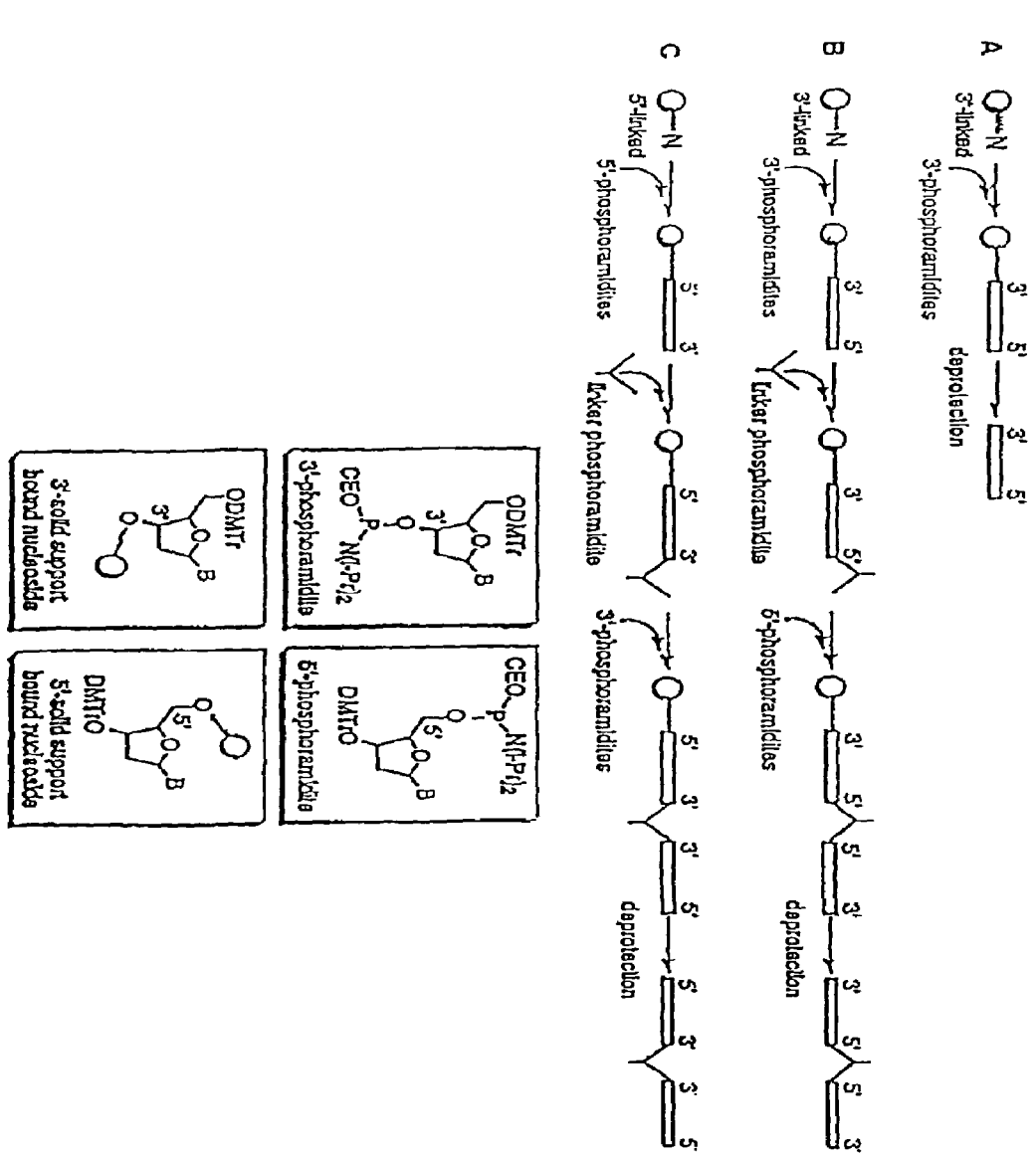
FIG. 2 is a synthetic scheme for the parallel synthesis of immunomers of the invention. DMTr=4,4'-dimethoxytrityl; CE=cyanoethyl.
Figure 3:
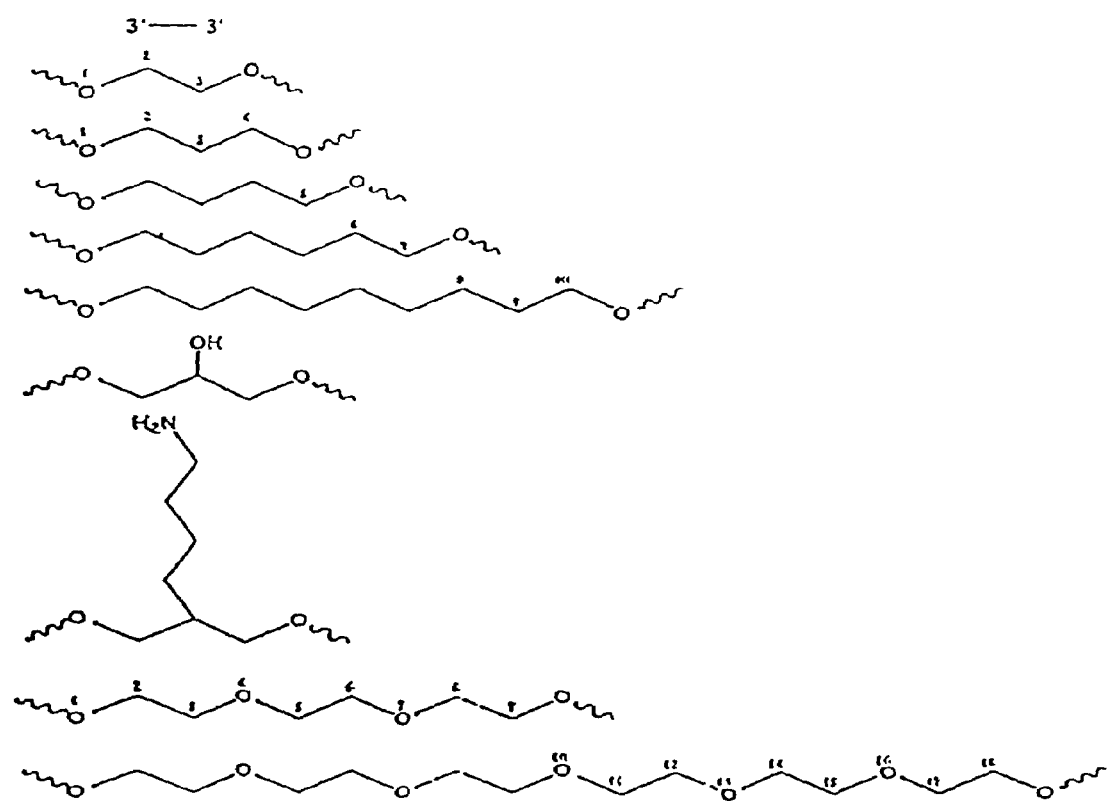
FIG. 3 depicts a group of representative small molecule linkers suitable for linear synthesis of immumomers of the invention.
Figure 4:
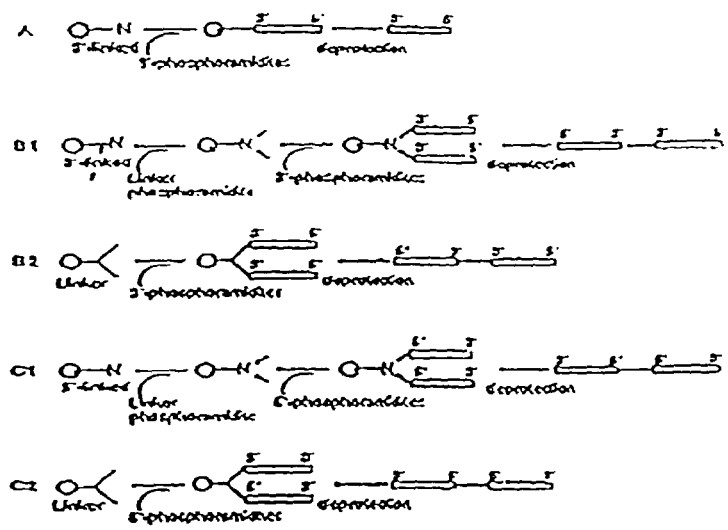
FIG. 4 is a synthetic scheme for the linear synthesis of immunomers of the invention. DMTr=4,4'-dimethoxytrityl; CE=cyanoethyl.
Figure 4:
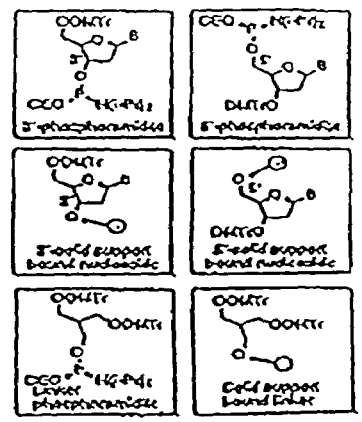

Immunostimulatory oligonucleotides were created as immunomers using the following protocols for synthesis. The immunostimulatory oligonucleotides and/or immunomers of the invention may conveniently be synthesized using an automated synthesizer and phosphoramidite approach as schematically depicted in FIGS. 2 and 4. In some embodiments, the immunostimulatory oligonucleotides and/or immunomers are synthesized by a linear synthesis approach (see FIG. 2). Representative linkers for this synthesis are presented in FIG. 3. As used herein, the term "linear synthesis" refers to a synthesis that starts at one end of the immunomer and progresses linearly to the other end. Linear synthesis permits incorporation of either identical or un-identical (in terms of length, base composition and/or chemical modifications incorporated) monomeric units into the immunostimulatory oligonucleotides and/or immunomers.

Figure 5:
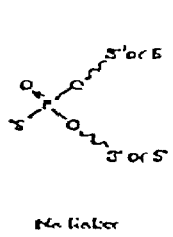
FIG. 5 depicts a group of representative small molecule linkers suitable for parallel synthesis of immunomers of the invention.
Figure 5:
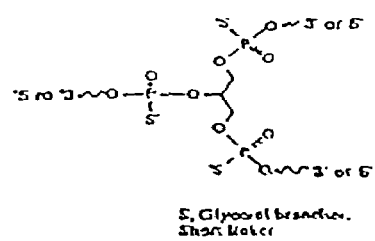
Figure 5:
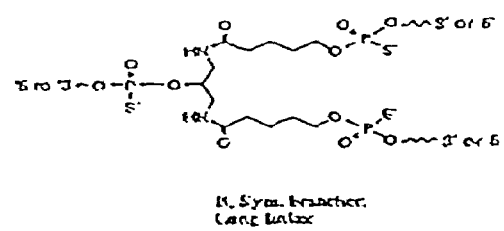

An alternative mode of synthesis for immunostimulatory oligonucleotides and/or immunomers is "parallel synthesis", in which synthesis proceeds outward from a central linker moiety (see FIG. 4). Representative linkers for this method of synthesis are presented in FIG. 5. A solid support attached linker can be used for parallel synthesis, as is described in U.S. Pat. No. 5,912,332. Alternatively, a universal solid support, such as phosphate attached to controlled pore glass support, can be used.

Parallel synthesis of immunostimulatory oligonucleotides and/or immunomers has several advantages over linear synthesis: (1) parallel synthesis permits the incorporation of identical monomeric units; (2) unlike in linear synthesis, both (or all) the monomeric units are synthesized at the same time, thereby the number of synthetic steps and the time required for the synthesis is the same as that of a monomeric unit; and (3) the reduction in synthetic steps improves purity and yield of the final immunomer product.

At the end of the synthesis by either linear synthesis or parallel synthesis protocols, the immunostimulatory oligonucleotides or immunomers according to the invention may conveniently be deprotected with concentrated ammonia solution or as recommended by the phosphoramidite supplier, if a modified nucleoside is incorporated. The product immunostimulatory oligonucleotides and/or immunomer is preferably purified by reversed phase HPLC, detritylated, desalted and dialyzed.

The compositions disclosed in the first second and third aspects of the invention can comprise the immunostimulatory oligonucleotide or immunomer alone or as oligonucleotide/immunomer conjugates. An oligonucleotide/immunomer conjugate comprises an oligonucleotide or immunomer, as described above, and an antigen conjugated to the oligonucleotide and/or immunomer at a position other than the accessible 5' end. In some embodiments, the non-nucleotidic linker comprises an antigen, which is conjugated to the oligonucleotide. In some other embodiments, the antigen is conjugated to the oligonucleotide at a position other than its 3' end. In some embodiments, the antigen produces a vaccine effect. The immunostimulatory oligonucleotide or immunomer alone or as oligonucleotide/immunomer conjugates can be administered in the methods discussed below.

The antigen is optionally selected from antigens associated with a pathogen, antigens associated with a cancer, antigens associated with an auto-immune disorder, and antigens associated with other diseases such as, but not limited to, veterinary or pediatric diseases, or wherein the antigen is an allergen. For purposes of the invention, the term "associated with" means that the antigen is present when the pathogen, cancer, auto-immune disorder, food allergy, skin allergy, respiratory allergy, asthma or other disease is present, but either is not present, or is present in reduced amounts, when the pathogen, cancer, auto-immune disorder, food allergy, skin allergy, respiratory allergy, or disease is absent.

The immunomer is covalently linked to the antigen, or it is otherwise operatively associated with the antigen. As used herein, the term "operatively associated with" refers to any association that maintains the activity of both immunomer and antigen. Nonlimiting examples of such operative associations include being part of the same liposome or other such delivery vehicle or reagent. In embodiments wherein the immunomer is covalently linked to the antigen, such covalent linkage preferably is at any position on the immunomer other than an accessible 5' end of an immunostimulatory oligonucleotide. For example, the antigen may be attached at an internucleoside linkage or may be attached to the non-nucleotidic linker. Alternatively, the antigen may itself be the non-nucleotidic linker.

In a fourth aspect, the invention provides methods for generating and/or modulating an immune response in a vertebrate, such methods comprising administering to the vertebrate an immunomer or immunomer conjugate according to the invention. In some embodiments, the vertebrate is a mammal. For purposes of this invention, the term "mammal" is expressly intended to include humans. In certain embodiments, the immunomer or immunomer conjugate is administered to a vertebrate in need of immunostimulation.

As used herein, the term "modulating" or "modulate" means to increase or decrease the immunostimulatory activity of an immunostimulatory nucleic acid relative to that of the parent immunostimulatory nucleic acid.

In the methods according to this aspect of the invention, administration of immunomers can be by any suitable route, including, without limitation, parenteral, oral, sublingual, transdermal, topical, intranasal, intramuscular, intraperitonal, subcutaneous, intradermal, aerosol, intraocular, intratracheal, intrarectal, vaginal, by gene gun, dermal patch or in eye drop or mouthwash form. Administration of the therapeutic compositions of immunomers can be carried out using known procedures at dosages and for periods of time effective to reduce symptoms or surrogate markers of the disease. When administered systemically, the therapeutic composition is preferably administered at a sufficient dosage to attain a blood level of immunomer from about 0.0001 micromolar to about 10 micromolar. For localized administration, much lower concentrations than this may be effective, and much higher concentrations may be tolerated. Preferably, a total dosage of immunomer ranges from about 0.001 mg per patient per day to about 200 mg per kg body weight per day. It may be desirable to administer simultaneously, or sequentially a therapeutically effective amount of one or more of the therapeutic compositions of the invention to an individual as a single treatment episode.

Either the immunomer or the vaccine, or both, may optionally be linked to an immunogenic protein, such as keyhole limpet hemocyanin (KLH), cholera toxin B subunit, or any other immunogenic carrier protein or nonimmunogenic carrier protein. Any of the plethora of adjuvants may be used including, without limitation, Freund's complete adjuvant, Freund's incomplete adjuvant, KLH, monophosphoryl lipid A (MPL), alum, and saponins, including QS-21, imiquimod, R848, or combinations thereof.

Toll-like receptors (TLRs) function as sensors of infection and induce the activation of innate and adaptive immune responses. TLRs recognize a wide variety of ligands, called pathogen-associated molecular patterns (PAMPs). Upon recognizing conserved pathogen-associated molecular products, TLRs activate host defense responses through their intracellular signaling domain, the Toll/interleukin-1 receptor (TIR) domain, and the downstream adaptor protein MyD88. Dendritic cells and macrophages normally respond to Toll-like receptor (TLR) ligands and cytokines (for example, interleukin-1β; IL-6 and tumor necrosis factor, TNF), which they also produce; natural killer (NK) cells and T cells are also involved in the pro-inflammatory circuit. After TLR stimulation by bacterial compounds, innate immune cells release a range of cytokines. Some examples of TLR ligands include, but are not limited to, lipoproteins; peptidoglycan, zymosan (TLR2), double-stranded RNA, polyI:polyC (TLR3), lipopolysaccharide, heat shock proteins, Taxol® (TLR4), flagellin (TLR5), and imidazoquinolines-R848, resiquimod, imiquimod; ssRNA (TLR7/8), beta-lymphocytes (TLR10) and uropathogenic *E. coli* (TLR11).

The methods according to this aspect of the invention are useful for model studies of the immune system. The methods are also useful for the prophylactic or therapeutic treatment of human or animal disease. For example, the methods are useful for pediatric and veterinary vaccine applications.

In a fifth aspect, the invention provides methods for therapeutically treating a vertebrate having a disease or disorder, such methods comprising administering to the vertebrate an immunomer or immunomer conjugate according to the invention. In various embodiments, the disease or disorder to be treated is cancer, an autoimmune disorder, airway inflammation, inflammatory disorders, allergy, asthma or a disease caused by a pathogen. Pathogens include bacteria, parasites, fungi, viruses, viroids and prions. Administration is carried out as described for the fourth aspect of the invention.

For purposes of the invention, the term "allergy" includes, without limitation, food allergies atopic dermatitis, allergic rhinitis (also known as hay fever), allergic conjunctivitis, urticaria (also known as hives), respiratory allergies and allergic reactions to other substances such as latex, medications and insect stings or problems commonly resulting from allergic rhinitis-sinusitis, otitis media and COPD. The term "airway inflammation" includes, without limitation, asthma. Specific examples of asthma include, but are not limited to, allergic asthma, non-allergic asthma, exercised-induced asthma, occupational asthma, and nocturnal asthma.

Allergic asthma is characterized by airway obstruction associated with allergies and triggered by substances called allergens. Triggers of allergic asthma include, but are not limited to, airborne pollens, molds, animal dander, house dust mites and cockroach droppings. Non-allergic asthma is caused by viral infections, certain medications or irritants found in the air, which aggravate the nose and airways. Triggers of non-allergic asthma include, but are not limited to, airborne particles (e.g., coal, chalk dust), air pollutants (e.g., tobacco smoke, wood smoke), strong odors or sprays (e.g., perfumes, household cleaners, cooking fumes, paints or varnishes), viral infections (e.g., colds, viral pneumonia, sinusitis, nasal polyps), aspirin-sensitivity, and gastroesophageal reflux disease (GERD). Exercise-induced asthma (EIA) is triggered by vigorous physical activity. Symptoms of EIA occur to varying degrees in a majority of asthma sufferers and are likely to be triggered as a result of breathing cold, dry air while exercising. Triggers of EIA include, but are not limited to, breathing airborne pollens during exercise, breathing air pollutants during exercise, exercising with viral respiratory tract infections and exercising in cold, dry air. Occupational asthma is directly related to inhaling irritants and other potentially harmful substances found in the workplace. Triggers of occupational asthma include, but are not limited to, fumes, chemicals, gases, resins, metals, dusts, vapors and insecticides.

As used herein, the term "autoimmune disorder" refers to disorders in which "self" proteins undergo attack by the immune system. Such term includes autoimmune asthma.

Without wishing to be bound to any particular theory, decreased exposure to bacteria may be partially responsible for the increased incidence of, severity of, and mortality due to allergic diseases such as asthma, atopic dermatitis, and rhinitis in the developed countries. This hypothesis is supported by evidence that bacterial infections or products can inhibit the development of allergic disorders in experimental animal models and clinical studies. Bacterial DNA or synthetic oligodeoxynucleotides containing unmethylated CpG dinucleotides and/or modified CpG dinucleotides in certain sequence contexts (CpG DNA) potently stimulate innate immune responses and thereby acquired immunity. The immune response to CpG DNA includes activation of innate immune cells, proliferation of B cells, induction of Th1 cytokine secretion, and production of immunoglobulins (Ig). The activation of immune cells by CpG DNA occurs via Toll-like receptor 9 (TLR9), a molecular pattern recognition receptor. CpG DNA induce strong Th1-dominant immune responses characterized by secretion of IL-12 and IFN-γ. Immunomers (IMO) alone or as allergen conjugates decrease production of IL4, IL-5, and IgE and reduce eosinophilia in mouse models of allergic asthma. IMO compounds also effectively reverse established atopic eosinophilic airway disease by converting a Th2 response to a Th1 response.

OVA with alum is commonly used to establish a Th2-dominant immune response in various mouse and rat models. The Th2 immune response includes increased IL-4, IL-5, and IL-13 production, elevated serum levels of total and antigen-specific IgE, IgG1, and lower levels of IgG2a. IMO compounds prevent and reverse established Th2-dominant immune responses in mice. The co-administration of IMO compounds with OVA/alum to mice reduces IL4, IL-5, and IL-13 production and induces IFN-γ production in spleen-cell cultures subjected to antigen re-stimulation. Furthermore, IMO compounds inhibit antigen-specific and total IgE and enhance IgG2a production in these mice.

Injection of OVA/alum and IMO compounds induces a lymphocyte antigen-recall response (Th1-type) in mice characterized by low levels of Th2-associated cytokines, IgE and IgG 1, and high levels of Th1-associated cytokines and IgG2a. Co-administration of IMO compounds with other kinds of antigens, such as S. masoni egg and hen egg lysozyme, also result in reversal of the Th2-response to a Th1-dominant response in in vitro and in vivo studies. As described herein, IMO compounds effectively prevent development of a Th2 immune response and allow a strong Th1 response.

While Th2 cytokines trigger an Ig isotype switch towards production of IgE and IgG1, the Th1 cytokine IFN-γ induces production of IgG2a by B-lymphocytes. Mice injected with OVA/alum and IMO compounds produce lower levels of IL4, IL-5, and IL-13 and higher levels of IFN-γ, accompanied by lower IgE and IgG1 and higher IgG2a levels, than mice injected with OVA/alum alone. This suggests the existence of a close link between Th1-cytokine induction and immunoglobulin isotype switch in mice that receive antigen and IMO compounds.

Serum antigen-specific and total IgE levels are significantly lower in mice receiving OVA/alum and IMO compounds than in mice receiving OVA/alum alone. In contrast, OVA-specific IgG1 levels are insignificantly changed and total IgG1 levels are only slightly decreased compared with mice injected with OVA/alum alone (data not shown). The different response may result from different mechanisms involved in the control of IgE and IgG1 class switch, though both isotypes are influenced by IL-4 and IL-13. For example, IL-6 promotes B lymphocytes to synthesize IgG1 in the presence of IL-4.

In a sixth aspect the invention provides a method for preventing cancer, an autoimmune disorder, airway inflammation, inflammatory disorders, skin disorders, allergy, asthma or a disease caused by a pathogen in a vertebrate. This method comprises administering to the vertebrate any one of the compositions, alone or in combination, disclosed in the first, second and third aspects of the invention. Pathogens include bacteria, parasites, fungi, viruses, viroids and prions. Administration is carried out as described for the fourth aspect of the invention.

In any of the methods according to the invention, the immunostimulatory oligonucleotide and/or immunomer or a conjugate thereof can be administered in combination with any other agent useful for treating the disease or condition that does not diminish the immunostimulatory effect of the oligonucleotide or immunomer. For purposes of this aspect of the invention, the term "in combination with" means in the course of treating the same disease in the same patient, and includes administering the oligonucleotide and/or immunomer and an agent in any order, including simultaneous administration, as well as any temporally spaced order, for example, from sequentially with one immediately following the other to up to several days apart. Such combination treatment may also include more than a single administration of the immunomer, and independently the agent. The administration of the oligonucleotide and/or immunomer and agent may be by the same or different routes.

In any of the methods according to the invention, the agent useful for treating the disease or condition includes, but is not limited to, vaccines, antigens, antibodies, cytotoxic agents, allergens, antibiotics, antisense oligonucleotides, peptides, proteins, gene therapy vectors, DNA vaccines and/or adjuvants to enhance the specificity or magnitude of the immune response, or co-stimulatory molecules such as cytokines, chemokines, protein ligands, trans-activating factors, peptides and peptides comprising modified amino acids. Additionally, the agent can include DNA vectors encoding for antigen or allergen. In these embodiments, the immunomers of the invention can variously act as adjuvants and/or produce direct immunostimulatory effects.

The examples below are intended to further illustrate certain preferred embodiments of the invention, and are not intended to limit the scope of the invention.

EXAMPLES

Example 1

Oligonucleotide Synthesis, Purification and Thermal Melt Profiles

CpG oligonucleotides (immunostimulatory oligonucleotides/immunomers) were synthesized on a 1 to 2 μmole scale using β-cyanoethylphosphoramidites on a PerSeptive Biosystem's 8909 Expedite DNA synthesizer (PerSeptive Biosystem, Boston, Mass.). The phosphoramidites of dA, dG, dC, and T were obtained from PE Biosystems (Foster City, Calif.). As described by Iyer R. P., et al. (*J. Am. Chem. Soc.* 112: 1253-1254 (1990)), an iodine oxidizing agent was used to obtain the phosphorothioate backbone modification. All oligos were deprotected using standard protocols, purified by HPLC, and dialyzed against USP quality sterile water for irrigation. The oligos were lyophilized and dissolved again in distilled water and the concentrations were determined from UV absorbance at 260 nm. All oligos were characterized by CGE and MALDI-TOF mass spectrometry (Applied Biosystem's Voyager-DE™ STR Biospectrometry™ Workstation)

for purity and molecular mass, respectively. The purity of full-length oligos ranged from 90-96% with the rest being shorter by one or two nucleotides (n-1 and n-2) as determined by CGE and/or denaturing PAGE. All oligos contained less than <0.1 EU/mL of endotoxin as determined by the Limulus assay (Bio-Whittaker now known as Cambrex Bio Science Walkersville, Inc., Walkersville, Md.).

Thermal melting studies were carried out in 1 mL solution of 10 mM disodium hydrogen phosphate, pH 7.2±0.2, containing 150 mM NaCl, and 2-mM MgCl2. The solutions were heated to 95° C. for 10 min and allowed to come to room temperature slowly before being stored at 4° C. overnight. The final concentration of oligonucleotide strand was 2.0 µM. UV thermal melting measurements were performed at 260 nm on a Perkin-Elmer Lambda 20 Spectrophotometer attached to a peltier thermal controller and a personal computer using 1 cm path length quartz cuvettes at a heating rate of 0.5° C./min. Melting temperatures (Tm) were taken as the temperature of half-dissociation and were obtained from first derivative plots. Each Tm value is an average of two or three independent experiments and the values were within ±1.0° C.

Example 2

Cell Culture Conditions and Reagents

Spleen cells from 4-8 week old BALB/c, C57BL/6 or C3H/HeJ mice were cultured in RPMI complete medium as described by Zhao, Q., et al. (*Biochem Pharmacol.* 51: 173-182 (1996)) and Branda, R. F., et al. (*Biochem. Pharmacol.* 45: 2037-2043 (1993)). Murine J774 macrophages (American Type Culture Collection, Manassas, Va.) were cultured in Dulbecco's modified Eagles medium supplemented with 10% (v/v) fetal calf serum and antibiotics (100 IU/mL of penicillin G/streptomycin). All other culture reagents were purchased from Mediatech (Gaithersburg, Md.).

Example 3

Spleen Cell Proliferation Assay

Typically, mouse (Balb-C) spleen cells were cultured with immunomer compounds at concentrations of 0.1, 1.0, and 10.0 µg/ml for 48 h and cell proliferation was determined by 3H-uridine incorporation, as described by Zhao, Q., et al. (*Biochem Pharmacol.* 51: 173-182 (1996)).

Example 4

Cytokine Induction Assays

Mouse spleen or J774 cells were plated in 24-well dishes using $5 \times 10^6$ or $1 \times 10^6$ cells/mL, respectively. The immunomer compounds dissolved in TE buffer (10 mM Tris-HCl, pH 7.5, 1 mM EDTA) were added to a final concentration of 0.03, 0.1, 0.3, 1.0, 3.0, or 10.0 µg/mL to the cell cultures. The cells were then incubated at 37° C. for 24 hr and the supernatants were collected for ELISA assays. The experiments were performed two or three times for each immunomer compound and in triplicate for each concentration. The secretion of IL-12 and IL-6 was measured by sandwich ELISA as described by Bhagat L., et al. (*Biochem. Biophys. Res. Commun.* 300: 853-861 (2003)). The required reagents, including cytokine antibodies and standards were purchased from BD Biosciences Pharmingen (San Diego, Calif.).

Example 5

Mouse Splenomegaly Assay

Female BALB/c mice (4-6 weeks, 19-21 gm) were divided into groups of three mice. Immunomer compounds were dissolved in sterile phosphate buffered saline (PBS) and administered subcutaneously (SC) to mice at a dose of 5 mg/kg. The mice were sacrificed after 48 hr and the spleens were harvested and weighed as described by Zhao, Q., et al. (*Biochem Pharmacol.* 51: 173-182 (1996)) and Branda, R. F., et al. (*Biochem. Pharmacol.* 45: 2037-2043 (1993)).

Example 6

Activation of the NF-κB Pathway

Toll-like receptor 9 (TLR9) has been shown to recognize unmethylated CpG-dinucleotides in bacterial, plasmid and synthetic DNAs (Hemmi H., et al. *Nature* 408: 740-745 (2000)) and activate stress kinase (Yi A. K., et al. *J. Immunol.* 161: 4493-4497 (1998)) and NF-κB pathways (Stacey K. J., et al. *J. Immunol.* 157: 2116-2122 (1996)). NF-κB activation in J774 cells treated with immunomer compounds was carried out and analyzed by EMSA as described Yu D., et al. (*Biochem. Biophys. Res. Commun.* 297: 83-90 (2002)) and Bhagat L., et al. (*Biochem. Biophys. Res. Commun.* 300: 853-861 (2003)).

Example 7

Isolation of Human B Cells and Plasmacytoid Dendritic Cells (pDCs).

PBMCs from freshly drawn healthy volunteer blood (CBR Laboratories, Boston, Mass.) were isolated by Ficoll density gradient centrifugation method (Histopaque-1077, Sigma) and B cells were isolated from PBMCs by positive selection using the CD19 cell isolation kit (Miltenyi Biotec) according to the manufacturer's instructions. Table 1 shows the immunostimulatory activity of immunomer compounds of the invention in C57BL/6 Splenocyte Assay.

TABLE 1

Immunomer Structure and C57BL/6 Splenocyte Assay (24 hs)

| SEQ ID NO | Sequences and Modification (5'-3') | IL-12 (pg/ml) 1 µg/ml | IL-12 (pg/ml) 1 µg/ml | IL-12 (pg/ml) 1 µg/ml |
|---|---|---|---|---|
| 19 | 5'-TCG$_1$AACG$_2$TTCG$_1$-X-G$_1$CTTG$_2$CAAG$_1$CT-5' | | | |
| 20 | 5'-TCG$_1$AAC$_1$GTTCG$_1$-X-G$_1$CTTGC$_1$AAG$_1$CT-5' | | | |

TABLE 1-continued

Immunomer Structure and C57BL/6 Splenocyte Assay (24 hs)

| SEQ ID NO | Sequences and Modification (5'-3') | | |
|---|---|---|---|
| 21 and 34 | 5'-TCG₁AACG₁TTCG₁-Y-TCTTG₁CTGTCT-5' | 6396 ± 10 | 911 ± 61 |
| 22 and 35 | 5'-TCG₁AACG₁TTCG₁-Y-TCTTG₂CTGTCT-5' | 7275 ± 77 | 749 ± 80 |
| 23 and 36 | 5'-TCG₁AACG₁TTCG₁-Y-TCTTGC₁TGTCT-5' | 8034 ± 14 | 918 ± 136 |
| 24 and 37 | 5'-TCG₁AACG₁TTCG₁-Y-TCTTCCACTCT-5' | | 752 ± 98 |
| 25 and 34 | 5'-TG₁CAAG₁CTTG₁C-Y-TCTTG₁CTGTCT-5' | | |
| 26 and 37 | 5'-TG₁CAAG₁CTTG₁C-Y-TCTTCCACTCT-5' | | |
| 27 | 5'-TG₁CAAG₁CTTG₁C-X-CG₁TTCG₁AACG₁T-5' | 389 ± | 59 |
| 28 | 5'-CTGTCG₁TTCTCo-X-oCTCTTG₂CTGTC-5' | | 717 ± 25 |
| 29 | 5'-CTGTCoG₂TTCTC-X-CTCTTG₂oCTGTC-5' | | 849 ± 29 |
| 30 | 5'-TCG₁TGTCG₁TTT-X-TTTG₁CTGTG₁CT-5' | | |
| 31 | 5'-TG₁CTGTG₁CTTT-X-TTTCG₁TGTCG₁T-5' | | |
| 32 and 38 | 5'-TCG₁AACG₁TTCG₁-Y-GACAG₁CTGTCT-5' | | |
| 33 and 39 | 5'-TG₁CAACG₁CTTG₁C-Y-GACACG₁ TGTCT-5' | | |
| Media | | 75 ± 28 | 104 ± 7 |

| SEQ ID NO | Sequences and Modification (5'-3') | IL-6 (pg/ml) 1 µg/ml | IL-6 (pg/ml) 1 µg/ml | IL-12 (pg/ml) 1 µg/ml |
|---|---|---|---|---|
| 19 | 5'-TCG₁AACG₂TTCG₁-X-G₁CTTG₂CAAG₁CT-5' | | | |
| 20 | 5'-TCG₁AAC₁GTTCG₁-X-G₁CTTGC₁AAG₁CT-5' | | | |
| 21 and 34 | 5'-TCG₁AACG₁TTCG₁-Y-TCTTG₁CTGTCT-5' | 2195 ± 77 | 423 ± 99 | |
| 22 and 35 | 5'-TCG₁AACG₁TTCG₁-Y-TCTTG₂CTGTCT-5' | 3278 ± 2 | 840 ± 243 | |
| 23 and 36 | 5'-TCG₁AACG₁TTCG₁-Y-TCTTGC₁TGTCT-5' | 7080 ± 0 | 1553 ± 670 | |
| 24 and 37 | 5'-TCG₁AACG₁TTCG₁-Y-TCTTCCACTCT-5' | | 693 ± 226 | |
| 25 and 34 | 5'-TG₁CAAG₁CTTG₁C-Y-TCTTG₁CTGTCT-5' | | | |
| 26 and 37 | 5'-TG₁CAAG₁CTTG₁C-Y-TCTTCCACTCT-5' | | | |
| 27 | 5'-TG₁CAAG₁CTTG₁C-X-CG₁TTCG₁AACG₁T-5' | 1329 ± 53 | | |
| 28 | 5'-CTGTCG₂TTCTCo-X-oCTCTTG₂CTGTC-5' | | 18 ± 3 | |
| 29 | 5'-CTGTCoG₂TTCTC-X-CTCTTG₂oCTGTC-5' | | 1230 ± 83 | |
| 30 | 5'-TCG₁TGTCG₁TTT-X-TTTG₁CTGTG₁CT-5' | | | |
| 31 | 5'-TG₁CTGTG₁CTTT-X-T1TCG₁TGTCG₁T-5' | | | |
| 32 and 38 | 5'-TCG₁AACG₁TTCG₁-Y-GACAG₁CTGTCT-5' | | | |
| 33 and 39 | 5'-TG₁CAACG₁CTTG₁C-Y-GACACG₁ TGTCT-5' | | | |
| Media | | 102 ± 25 | 12 ± 2 | |

Normal phase represents a phosphorothioate linkage; o represents a phosphodiester linkage.
$G_1$ = 2'-deoxy-7-deazaguanosine
$G_2$ = Arabinoguanosine
$C_1$ = 1-(2'-deoxy-β-D-ribofuranosyl)-2-oxo-7-deaza-8-methylpurine
X = Glycerol Linker
Y = C3 Linker

Example 8

Human pDC Cultures and IFN-α and IFN-β ELISA pDCs were isolated from human PBMCs using a BDCA-4 cell isolation kit (Miltenyi Biotec) according to the manufacturer's instructions. pDC were plated in 96-well plates using $1 \times 10^6$ cells/mL, 200 μL/well). The immunomer compounds were added to a final concentration of 0.3, 1.0, 3.0, or 10.0 μg/mL to the cell cultures and incubated at 37° C. for 24 hr. Supernatants were then harvested and assayed for IFN-α and IFN-β using ELISA kit (PBL). Tables 2A-2D show an average ±SD of IFN-α and IFN-β for immunomer compounds according to the invention at a concentration of 10.0 μg/mL.

TABLE 2A

Immunomer Structure and Immunostimulatory Activity in Human DC Assay (24 hs)

| SEQ ID NO | Sequences and Modification (5'-3') | IFN-α (pg/ml) 10 μg/ml DN1 | IFN-α (pg/ml) 10 μg/ml DN2 | IFN-α (pg/ml) 10 μg/ml DN3 |
|---|---|---|---|---|
| 1 | 5'-TCG$_1$AACG$_1$TTCG$_1$-X-G$_1$CTTG$_1$CAAG$_1$CT-5' | 26112 ± 604 | 25825 ± 416 | 96264 ± 605 |
| 2 | 5'-TCG$_1$AACG$_1$TTCG-X-GCTTG$_1$CAAG$_1$CT-5' | 20340 ± 106 | 12270 ± 306 | 105804 ± 688 |
| 3 | 5'-TCTCACCTTCT-X-TCTTCCACTCT-5' | 185 ± 0 | 311 ± 4 | 1649 ± 262 |
| 4 | 5'-TCG$_2$AACG$_2$TTCG$_2$-X-G$_2$CTTG$_2$CAAG$_2$CT-5' | | | |
| 5 | 5'-TCG$_2$AACG$_2$TTCG-X-GCTTG$_2$CMG$_2$CT-5 T | | | |
| media | | 177 ± 0 | 177 ± 0 | 0 ± 0 |

| SEQ ID NO | Sequences and Modification (5'-3') | IFN-α (pg/ml) 10 μg/ml DN4 | IFN-α (pg/ml) 10 μg/ml DN5 | IFN-α (pg/ml) 10 μg/ml DN6 |
|---|---|---|---|---|
| 1 | 5'-TCG$_1$AACG$_1$TTCG$_1$-X-G$_1$CTTG$_1$CAAG$_1$CT-5' | 41718 ± 101 | 25011 ± 5 | 19608 ± 5 |
| 2 | 5'-TCG$_1$AACG$_1$TTCG-X-GCTTG$_1$CAAG$_1$CT-5' | 49176 ± 302 | 14014 ± 1414 | 21988 ± 1413 |
| 3 | 5'-TCTCACCTTCT-X-TCTTCCACTCT-5' | 0 ± 0 | 197 ± 0 | 201 ± 0 |
| 4 | 5'-TCG$_2$AACG$_2$TTCG$_2$-X-G$_2$CTTG$_2$CAAG$_2$CT-5' | | | |
| 5 | 5'-TCG$_2$AACG$_2$TTCG-X-GCTTG$_2$CAAG$_2$CT-5' | | | |
| media | | 0 ± 0 | 201 ± 0 | 196 ± 0 |

Normal phase represents a phosphorothioate linkage
$G_1$ = 2'-deoxy-7-deazaguanosine
$G_2$ = Arabinoguanosine
X = Glycerol linker

TABLE 2B

Immunomer Structure and Immunostimulatory Activity in Human DC Assay (24 hs)

| SEQ ID NO | Sequences and Modification (5'-3') | IFN-α (pg/ml) 10 μg/ml DN1 | IFN-α (pg/ml) 10 μg/ml DN2 | IFN-α (pg/ml) 10 μg/ml DN3 |
|---|---|---|---|---|
| 6 | 5'-TCG$_1$TCG$_1$AACG$_1$TTCG$_1$AGATGAT-3' | 37116 ± 1108 | 44624 ± 321 | 58908 ± 707 |
| 7 | 5'-TCG$_2$TCG$_2$AACG$_2$TTCG$_2$AGATGAT-3' | 6606 ± 950 | 5022 ± 334 | 15637 ± 698 |
| 8 | 5'-TCG$_3$TCG$_3$AACG$_3$TTCG$_3$AGATGAT-3' | 1405 ± 121 | 7750 ± 618 | 46311 ± 506 |
| 9 | 5'-TC$_1$GTC$_1$GAAC$_1$GTTC$_1$GAGATGAT-3' | 611 ± 33 | 231 ± 4 | 0 ± 0 |
| 10 | 5'-TC$_2$GTC$_2$GAAC$_2$GTTC$_2$GAGATGAT-3' | 269 ± 7 | 185 ± 0 | 2574 ± 64 |
| 11 | 5'-TC$_3$GTC$_3$GAAC$_3$GTTC$_3$GAGATGAT-3' | 191 ± 0 | 188 ± 0 | 0 ± 0 |
| media | | 177 ± 0 | 177 ± 0 | 0 ± 0 |

TABLE 2B-continued

Immunomer Structure and Immunostimulatory Activity in Human DC Assay (24 hs)

| SEQ ID NO | Sequences and Modification (5'-3') | IFN-α (pg/ml) 10 µg/ml DN4 | IFN-α (pg/ml) 10 µg/ml DN5 | IFN-α (pg/ml) 10 µg/ml DN6 |
|---|---|---|---|---|
| 6 | 5'-TCG$_1$TCG$_1$AACG$_1$TTCG$_1$AGATGAT-3' | 98178 ± 375 | 68722 ± 1358 | 31678 ± 715 |
| 7 | 5'-TCG$_2$TCG$_2$AACG$_2$TTCG$_2$AGATGAT-3' | 40782 ± 885 | 19180 ± 735 | 8696 ± 1122 |
| 8 | 5'-TCG$_3$TCG$_3$AACG$_3$TTCG$_3$AGATGAT-3' | 12446 ± 894 | 42195 ± 2665 | 582 ± 78 |
| 9 | 5'-TC$_1$GTC$_1$GAAC$_1$GTTC$_1$GAGATGAT-3' | 10175 ± 206 | 15966 ± 1256 | 6857 ± 1335 |
| 10 | 5'-TC$_2$GTC$_2$GAAC$_2$GTTC$_2$GAGATGAT-3' | 13028 ± 911 | 1947 ± 204 | 30 ± 5 |
| 11 | 5'-TC$_3$GTC$_3$GAAC$_3$GTTC$_3$GAGATGAT-3' | 0 ± 0 | 355 ± 16 | 17 ± 0 |
| media | | 0 ± 0 | 12 ± 0 | 10 ± 0 |

Normal phase represents a phosphorothioate linkage
$G_1$ = 2'-deoxy-7-deazaguanosine
$G_2$ = Arabinoguanosine
$G_3$ = 2'-deoxyinosine
$C_1$ = 1-(2'-deoxy-β-D-ribofuranosyl)-2-oxo-7-deaza-8-methylpurine
$C_2$ = Arabinocytidine
$C_3$ = 2'-deoxy-5-hydroxycytidine

TABLE 2C

Immunomer Structure and Immunostimulatory Activity in Human DC Assay (24 hs)

| SEQ ID NO | Sequences and Modification (5'-3') | IFN-α (pg/ml) 10 µg/ml DN1 | IFN-α (pg/ml) 10 µg/ml DN2 | IFN-α (pg/ml) 10 µg/ml DN3 |
|---|---|---|---|---|
| 1 | 5'-TCG$_1$AACG$_1$TTCG$_1$-X-G$_1$CTTG$_1$CAAG$_1$CT-5' | 67088 ± 306 | 35055 ± 659 | 62805 ± 328 |
| 40 | 5'-TCG$_1$AACG$_1$TTCT-X-TCTTG$_1$CAAG$_1$CT-5' | 12588 ± 448 | 19986 ± 1418 | 38002 ± 1087 |
| 12 | 5'-TCG$_1$AACG$_1$TTC-X-CTTG$_1$CAAG$_1$CT-5' | 16090 ± 179 | 16712 ± 584 | 90560 ± 1690 |
| 13 | 5'-TCG$_1$TTCG$_1$AACG$_1$-X-G$_1$CAAG$_1$CTTG$_1$CT-5' | 9092 ± 291 | 9286 ± 615 | 60570 ± 867 |
| 14 | 5'-TCCAACCTTCG-X-GCTTCCAACCT-5' | 770 ± 158 | 208 ± 28 | 5529 ± 286 |
| 15 | 5'-TCG$_1$TTG$_1$CAACG$_1$-X-G$_1$CAACG$_1$TTG$_1$CT-5' | 40353 ± 542 | 33164 ± 419 | 72730 ± 954 |
| 4 | 5'-TCG$_2$AACG$_2$UCG$_2$-X-G$_2$CFFG$_2$CAAG$_2$CT-5' | | | |
| 16 | 5'-TCG$_2$AACG$_2$TTCT-X-TCTTG$_2$CAAG$_2$CT-5' | | | |
| 17 | 5'-TCG$_1$AACG$_2$TTCG$_1$-X-G$_1$CTTG$_2$CAAG$_1$CT-5' | | | |
| 18 | 5'-TCG$_1$AAC$_1$GTTCG$_1$-X-G$_1$CTTGC$_1$AAG$_1$CT-5' | | | |
| media | | 160 ± 7 | 259 ± 20 | 0 ± 0 |

| SEQ ID NO | Sequences and Modification (5'-3') | IFN-α (pg/ml) 10 µg/ml DN4 | IFN-α (pg/ml) 10 µg/ml DN5 | IFN-α (pg/ml) 10 µg/ml DN6 |
|---|---|---|---|---|
| 1 | 5'-TCG$_1$AACG$_1$TTCG$_1$-X-G$_1$CTTG$_1$CAAG$_1$CT-5' | 66980 ± 217 | 6552 ± 1 | 7992 ± 24 |
| 40 | 5'-TCG$_1$AACG$_1$TTCT-X-TCTTG$_1$CAAG$_1$CT-5' | 83115 ± 134 | | |
| 12 | 5'-TCG$_1$AACG$_1$TTC-X-CTTG$_1$CAAG$_1$CT-5' | 61230 ± 1120 | | |
| 13 | 5'-TCG$_1$TTCG$_1$AACG$_1$-X-G$_1$CAAG$_1$CTTG$_1$CT-5' | 34430 ± 451 | | |
| 14 | 5'-TCCAACCTTCG-X-GCTTCCAACCT-5' | 2044 ± 62 | | |

TABLE 2C-continued

Immunomer Structure and Immunostimulatory Activity in Human DC Assay (24 hs)

| SEQ ID NO | Sequences and Modification (5'-3') | | | |
|---|---|---|---|---|
| 15 | 5'-TCG$_1$TTG$_1$CAACG$_1$-X-G$_1$CAACG$_1$TTG$_1$CT-5' | 33716 ± 872 | | |
| 4 | 5'-TCG$_2$AACG$_2$TTCG$_2$-X-G$_2$CTTG$_2$CAAG$_2$CT-5' | | 2440 ± 23 | 2403 ± 4 |
| 16 | 5'-TCG$_2$AACG$_2$TTCT-X-TCTTG$_2$CAAG$_2$CT-5' | | 1316 ± 0 | 1683 ± 10 |
| 17 | 5'-TCG$_1$AACG$_2$TTCG$_1$-X-G$_1$CTTG$_2$CAAG$_1$CT-5' | | | |
| 18 | 5'-TCG$_1$AAC$_1$GTTCG$_1$-X-G$_1$CTTGC$_1$AAG$_1$CT-5' | | | |
| media | | 546 ± 0 | 0 ± 0 | 0 ± 0 |

| SEQ ID NO | Sequences and Modification (5'-3') | IFN-60 (pg/ml) 10 µg/ml DN7 | IFN-60 (pg/ml) 10 µg/ml DN8 | IFN-60 (pg/ml) 10 µg/ml DN9 |
|---|---|---|---|---|
| 1 | 5'-TCG$_1$AACG$_1$TTCG$_1$-X-G$_1$CTTG$_1$CAAG$_1$CT-5' | 31227 ± 1341 | 9777 ± 10 | 10008 ± 10 |
| 40 | 5'-TCG$_1$AACG$_1$TTCT-X-TCTTG$_1$CAAG$_1$CT-5' | | | |
| 12 | 5'-TCG$_1$AACG$_1$TTC-X-CTTG$_1$CAAG$_1$CT-5' | | | |
| 13 | 5'-TCG$_1$TTCG$_1$AACG$_1$-X-G$_1$CAAG$_1$CTTG$_1$CT-5' | | | |
| 14 | 5'-TCCAACCTTCG-X-GCTTCCAACCT-5' | | | |
| 15 | 5'-TCG$_1$TTG$_1$CAACG$_1$-X-G$_1$CAACG$_1$TTG$_1$CT-5' | | | |
| 4 | 5'-TCG$_2$AACG$_2$TTCG$_2$-X-G$_2$CTTG$_2$CAAG$_2$CT-5' | 6083 ± 184 | | |
| 16 | 5'-TCG$_2$AACG$_2$TTCT-X-TCTTG$_2$CAAG$_2$CT-5' | 2164 ± 4 | | |
| 17 | 5'-TCG$_1$AACG$_2$TTCG$_1$-X-G$_1$CTTG$_2$CAAG$_1$CT-5' | | | |
| 18 | 5'-TCG$_1$AAC$_1$GTTCG$_1$-X-G$_1$CTTGC$_1$AAG$_1$CT-5' | | | |
| media | | 0 ± 0 | 0 ± 0 | 0 ± 0 |

| SEQ ID NO | Sequences and Modification (5'-3') | IFN-62 (pg/ml) 10 µg/ml DN8 | IFN-β (pg/ml) 10 µg/ml DN9 |
|---|---|---|---|
| 1 | 5'-TCG$_1$AACG$_1$TTCG$_1$-X-G$_1$CTTG$_1$CAAG$_1$CT-5' | 1370 ± 54 | 650 ± 38 |
| 40 | 5'-TCG$_1$AACG$_1$TTCT-X-TCTTG$_1$CAAG$_1$CT-5' | | |
| 12 | 5'-TCG$_1$AACG$_1$TTC-X-CTTG$_1$CAAG$_1$CT-5' | | |
| 13 | 5'-TCG$_1$TTCG$_1$AACG$_1$-X-G$_1$CAAG$_1$CTTG$_1$CT-5' | | |
| 14 | 5'-TCCAACCTTCG-X-GCTTCCAACCT-5' | | |
| 15 | 5'-TCG$_1$1TG$_1$CAACG$_1$-X-G$_1$CAACG$_1$TTG$_1$CT-5' | | |
| 4 | 5'-TCG$_2$AACG$_2$TTCG$_2$-X-G$_2$CTTG$_2$CAAG$_2$CT-5' | | |
| 16 | 5'-TCG$_2$AACG$_2$TTCT-X-TCTTG$_2$CAAG$_2$CT-5' | | |
| 17 | 5'-TCG$_1$AACG$_2$UCG$_1$-X-G$_1$CTTG$_2$CAAG$_1$CT-5' | | |
| 18 | 5'-TCG$_1$AAC$_1$GTTCG$_1$-X-G$_1$CTTGC$_1$AAG$_1$CT-5 | | |
| media | | 0 ± 0 | 0 ± 0 |

Normal phase represents a phosphorothioate linkage
G$_1$ = 2'-deoxy-7-deazaguanosine
G$_2$ = Arabinoguanosine
C$_1$ = 1-(2'-deoxy-β-D-ribofuranosyl)-2-oxo-7-deaza-8-methylpurine
X = Glycerol Linker

TABLE 2D

Immunomer Structure and Immunostimulatory Activity in Human DC Assay (24 hs)

| SEQ ID NO | Sequences and Modification (5'-3') | IFN-α (pg/ml) 10 µg/ml DN1 | IFN-α (pg/ml) 10 µg/ml DN2 | IFN-α (pg/ml) 10 µg/ml DN3 |
|---|---|---|---|---|
| 19 | 5'-TCG$_1$AACG$_2$TTCG$_1$-X-G$_1$CTTG$_2$CAAG$_1$CT-5' | 3145 ± 4 | 5808 ± 28 | 22050 ± 407 |
| 20 | 5'-TCG$_1$AAC$_1$GTTCG$_1$-X-G$_1$CTTGC$_1$AAG$_1$CT-5' | 4710 ± 31 | 5656 ± 0 | 14157 ± 10 |
| 21 and 34 | 5'-TCG$_1$AACG$_1$TTCG$_1$-Y-TCTTG$_1$CTGTCT-5' | | | |
| 22 and 35 | 5'-TCG$_1$AACG$_1$TTCG$_1$-Y-TCTTG$_2$CTGTCT-5' | | | |
| 23 and 36 | 5'-TCG$_1$AACG$_1$TTCG$_1$-Y-TCTTGC$_1$TGTCT-5' | | | |
| 24 and 37 | 5'-TCG$_1$AACG$_1$TTCG$_1$-Y-TCTTCCACTCT-5' | | | |
| 25 and 34 | 5'-TG$_1$CAAG$_1$CTTG$_1$C-Y-TCTTG$_1$CTGTCT-5' | | | |
| 26 and 37 | 5'-TG$_1$CAAG$_1$CTTG$_1$C-Y-TCTTCCACTCT-5' | | | |
| 27 | 5'-TG$_1$CAAG$_1$CTTG$_1$C-X-CG$_1$TTCG$_1$AACG$_1$T-5' | | | |
| 28 | 5'-CTGTCG$_2$TTCTCo-X-oCTCTTG$_2$CTGTC-5' | | | |
| 29 | 5'-CTGTCoG$_2$TTCTC-X-CTCTTG$_2$oCTGTC-5' | | | |
| 30 | 5'-TCG$_1$TGTCG$_1$TTT-X-TTTG$_1$CTGTG$_1$CT-5' | | | |
| 31 | 5'-TG$_1$CTGTG$_1$CUT-X-TTTCG$_1$TGTCG$_1$T-5' | | | |
| 32 and 38 | 5'-TCG$_1$AACG$_1$TTCG$_1$-Y-GACAG$_1$CTGTCT-5' | | | |
| 33 and 39 | 5'-TG$_1$CAACG$_1$CTTG$_1$C-Y-GACACG$_1$ TGTCT-5' | | | |
| Media | | 228 ± 0 | 234 ± 0 | 116 ± 0 |

| SEQ ID NO | Sequences and Modification (5'-3') | IFN-α (pg/ml) 10 µg/ml DN1 | IFN-α (pg/ml) 10 µg/ml DN2 | IFN-α (pg/ml) 10 µg/ml DN3 |
|---|---|---|---|---|
| 19 | 5'-TCG$_1$AACG$_2$TTCG$_1$-X-G$_1$CTTG$_2$CAAG$_1$CT-5' | 16100 ± 542 | | |
| 20 | 5'-TCG$_1$AAC$_1$GTTCG$_1$-X-G$_1$CTTGC$_1$AAG$_1$CT-5' | 23768 ± 1371 | | |
| 21 and 34 | 5'-TCG$_1$AACG$_1$TTCG$_1$-Y-TCTTG$_1$CTGTCT-5' | | 5824 ± 530 | 2090 ± 81 |
| 22 and 35 | 5'-TCG$_1$AACG$_1$TTCG$_1$-Y-TCTTG$_2$CTGTCT-5' | | 9582 ± 49 | 1623 ± 108 |
| 23 and 36 | 5'-TCG$_1$AACG$_1$TTCG$_1$-Y-TCTTGC$_1$TGTCT-5' | | 6912 ± 157 | 1577 ± 168 |
| 24 and 37 | 5'-TCG$_1$AACG$_1$TTCG$_1$-Y-TCTTCCACTCT-5' | | 19570 ± 467 | 2254 ± 25 |
| 25 and 34 | 5'-TG$_1$CAAG$_1$CTTG$_1$C-Y-TCTTG$_1$CTGTCT-5' | | | |
| 26 and 37 | 5'-TG$_1$CAAG$_1$CTTG$_1$C-Y-TCTTCCACTCT-5' | | | |
| 27 | 5'-TG$_1$CAAG$_1$CTTG$_1$C-X-CG$_1$TTCG$_1$AACG$_1$T-5' | | | |
| 28 | 5'-CTGTCG$_2$TTCTCo-X-oCTCTTG$_2$CTGTC-5' | | | |
| 29 | 5'-CTGTCoG$_2$TTCTC-X-CTCTTG$_2$oCTGTC-5' | | | |
| 30 | 5'-TCG$_1$TGTCG$_1$TTT-X-TTTG$_1$CTGTG$_1$CT-5' | | | |
| 31 | 5'-TG$_1$CTGTG$_1$CTTT-X-TTTCG$_1$TGTCG$_1$T-5' | | | |
| 32 and 38 | 5'-TCG$_1$AACG$_1$TTCG$_1$-Y-GACAG$_1$CTGTCT-5' | | | |
| 33 and 39 | 5'-TG$_1$CAACG$_1$CTTG$_1$C-Y-GACACG$_1$TGTCT-5' | | | |
| Media | | 125 ± 3 | 157 ± 0 | 179 ± 0 |

TABLE 2D-continued

Immunomer Structure and Immunostimulatory Activity in Human DC Assay (24 hs)

| SEQ ID NO | Sequences and Modification (5'-3') | IFN-α (pg/ml) 10 µg/ml DN7 | IFN-α (pg/ml) 10 µg/ml DN8 | IFN-α (pg/ml) 10 µg/ml DN9 |
|---|---|---|---|---|
| 19 | 5'-TCG$_1$AACG$_2$TTCG$_1$-X-G$_1$CTTG$_2$CAAG$_1$CT-5' | | | |
| 20 | 5'-TCG$_1$AAC$_1$GTTCG$_1$-X-G$_1$CTTGC$_1$AAG$_1$CT-5' | | | |
| 21 and 34 | 5'-TCG$_1$AACG$_1$TTCG$_1$-Y-TCTTG$_1$CTGTCT-5' | 1049 ± 13 | 15594 ± 48 | 6024 ± 135 |
| 22 and 35 | 5'-TCG$_1$AACG$_1$TTCG$_1$-Y-TCTTG$_2$CTGTCT-5' | 2230 ± 78 | 6118 ± 3 | 3162 ± 189 |
| 23 and 36 | 5'-TCG$_1$AACG$_1$TTCG$_1$-Y-TCTTGC$_1$TGTCT-5' | 1535 ± 130 | 6680 ± 35 | 1558 ± 45 |
| 24 and 37 | 5'-TCG$_1$AACG$_1$TTCG$_1$-Y-TCTTCCACTCT-5' | 16053 ± 3815 | 9502 ± 57 | 6228 ± 0 |
| 25 and 34 | 5'-TG$_1$CAAG$_1$CTTG$_1$C-Y-TCTTG$_1$CTGTCT-5' | | | |
| 26 and 37 | 5'-TG$_1$CAAG$_1$CTTG$_1$C-Y-TCTTCCACTCT-5' | | | |
| 27 | 5'-TG$_1$CAAG$_1$CTTG$_1$C-X-CG$_1$TTCG$_1$AACG$_1$T-5' | | | |
| 28 | 5'-CTGTCG$_2$TTCTCo-X-oCTCTTG$_2$CTGTC-5' | | 6632 ± 184 | 3166 ± 242 |
| 29 | 5'-CTGTCoG$_2$TTCTC-X-CTCTTG$_2$oCTGTC-5' | | 6864 ± 394 | 1146 ± 42 |
| 30 | 5'-TCG$_1$TGTCG$_1$TTT-X-TTTG$_1$CTGTG$_1$CT-5' | | | |
| 31 | 5'-TG$_1$CTGTG$_1$CTTT-X-TTTCG$_1$TGTCG$_1$T-5' | | | |
| 32 and 38 | 5'-TCG$_1$AACG$_1$TCG$_1$-Y-GACAG$_1$CTGTCT-5' | | | |
| 33 and 39 | 5'-TG$_1$CAACG$_1$CTTG$_1$C-Y-GACACG$_1$ TGTCT-5' | | | |
| Media | | 157 ± 0 | 82 ± 0 | 94 ± 2 |

| SEQ ID NO | Sequences and Modification (5'-3') | IFN-α (pg/ml) 10 µg/ml DN11 | IFN-α (pg/ml) 10 µg/ml DN22 | IFN-α (pg/ml) 10 µg/ml DN12 |
|---|---|---|---|---|
| 19 | 5'-TCG$_1$AACG$_2$TTCG$_1$-X-G$_1$CTTG$_2$CAAG$_1$CT-5' | | | |
| 20 | 5'-TCG$_1$AAC$_1$GTTCG$_1$-X-G$_1$CTTGC$_1$AAG$_1$CT-5' | | | |
| 21 and 34 | 5'-TCG$_1$AACG$_1$TTCG$_1$-Y-TCTTG$_1$CTGTCT-5' | 8154 ± 597 | 31854 ± 136 | |
| 22 and 35 | 5'-TCG$_1$AACG$_1$TTCG$_1$-Y-TCTTG$_2$CTGTCT-5' | 6413 ± 876 | 14493 ± 613 | 9642 ± 129 |
| 23 and 36 | 5'-TCG$_1$AACG$_1$TTCG$_1$-Y-TCTTGC$_1$TGTCT-5' | 2688 ± 293 | 4486 ± 94 | |
| 24 and 37 | 5'-TCG$_1$AACG$_1$TTCG$_1$-Y-TCTTCCACTCT-5' | 7214 ± 18 | 10068 ± 31 | |
| 25 and 34 | 5'-TG$_1$CAAG$_1$CTTG$_1$C-Y-TCTTG$_1$CTGTCT-5' | | | 11474 ± 402 |
| 26 and 37 | 5'-TG$_1$CAAG$_1$CTTG$_1$C-Y-TCTTCCACTCT-5' | | | 375 ± 23 |
| 27 | 5'-TG$_1$CAAG$_1$CTTG$_1$C-X-CG$_1$TTCG$_1$AACG$_1$T-5' | | | |
| 28 | 5'-CTGTCG$_2$TTCTCo-X-oCTCTTG$_2$CTGTC-5' | 5508 ± 410 | 13956 ± 355 | 6009 ± 240 |
| 29 | 5'-CTGTCoG$_2$TTCTC-X-CTCTTG$_2$oCTGTC-5' | 5599 ± 146 | 11824 ± 720 | 9977 ± 1379 |
| 30 | 5'-TCG$_1$TGTCG$_1$TTT-X-TTTG$_1$CTGTG$_1$CT-5' | | | 11946 ± 159 |
| 31 | 5'-TG$_1$CTGTG$_1$CTTT-X-TTTCG$_1$TGTCG$_1$T-5' | | | 0 ± 0 |
| 32 and 38 | 5'-TCG$_1$AACG$_1$TCG$_1$-Y-GACAG$_1$CTGTCT-5' | | | 10032 ± 9 |

TABLE 2D-continued

Immunomer Structure and Immunostimulatory Activity in Human DC Assay (24 hs)

| | | | | |
|---|---|---|---|---|
| 33 and 39 | 5'-TG₁CAACG₁C₁TG₁C-Y-GACACG₁TGTCT-5' | | | 6420 ± 139 |
| Media | | 80 ± 0 | 101 ± 7 | 0 ± 0 |

Normal phase represents a phosphorothioate linkage; o represents a phosphodiester linkage.
$G_1$ = 2'-deoxy-7-deazaguanosine
$G_2$ = Arabinoguanosine
$C_1$ = 1-(2'-deoxy-β-D-ribofuranosyl)-2-oxo-7-deaza-8-methylpurine
X = Glycerol Linker
Y = C3 Linker

Example 9

Cytokine Analysis

The secretion of IFN-α in vertebrate cells, preferably BALB/c mouse spleen cells or human PBMC, was measured by sandwich ELISA. The required reagents including cytokine antibodies and cytokine standards were purchased form PharMingen, San Diego, Calif. ELISA plates (Costar) were incubated with appropriate antibodies at 5 μg/mL in PBSN buffer (PBS/0.05% sodium azide, pH 9.6) overnight at 4° C. and then blocked with PBS/1% BSA at 37° C. for 30 minutes. Cell culture supernatants and cytokine standards were appropriately diluted with PBS/10% FBS, added to the plates in triplicate, and incubated at 25° C. for 2 hours. Plates were overlaid with 1 μg/mL appropriate biotinylated antibody and incubated at 25° C. for 1.5 hours. The plates were then washed extensively with PBS-T Buffer (PBS/0.05% Tween 20) and further incubated at 25° C. for 1.5 hours after adding streptavidin conjugated peroxidase (Sigma, St. Louis, Mo.). The plates were developed with Sure Blue™ (Kirkegaard and Perry) chromogenic reagent and the reaction was terminated by adding Stop Solution (Kirkegaard and Perry). The color change was measured on a Ceres 900 HDI Spectrophotometer (Bio-Tek Instruments).

Human peripheral blood mononuclear cells (PBMCs) were isolated from peripheral blood of healthy volunteers by Ficoll-Paque density gradient centrifugation (Histopaque-1077, Sigma, St. Louis, Mo.). Briefly, heparinized blood was layered onto the Histopaque-1077 (equal volume) in a conical centrifuge and centrifuged at 400×g for 30 minutes at room temperature. The buffy coat, containing the mononuclear cells, was removed carefully and washed twice with isotonic phosphate buffered saline (PBS) by centrifugation at 250×g for 10 minutes. The resulting cell pellet was then resuspended in RPMI 1640 medium containing L-glutamine (MediaTech, Inc., Herndon, Va.) and supplemented with 10% heat inactivated FCS and penicillin-streptomycin (100 U/ml). Cells were cultured in 24 well plates for different time periods at 1×10⁶ cells/ml/well in the presence or absence of oligonucleotides. At the end of the incubation period, supernatants were harvested and stored frozen at −70° C. until assayed for various cytokines including IFN-α (BioSource International) by sandwich ELISA. The results are shown in Table 3A-3D below.

In all instances, the levels of IFN-α in the cell culture supernatants was calculated from the standard curve constructed under the same experimental conditions for IFN-α.

TABLE 3A

Immunomer Structure and Immunostimulatory Activity in Human PBMC Assay (24 hs)

| SEQ ID NO | Sequences and Modification (5'-3') | IFN-α (pg/ml) 10 μg/ml DN4 | IFN-α (pg/ml) 10 μg/ml DN5 | IFN-α (pg/ml) 10 μg/ml DN6 |
|---|---|---|---|---|
| 1 | 5'-TCG₁AACG₁TTCG₁-X-G₁CTTG₁CAAG₁CT-5' | 8222 ± 44 | 6114 ± 1 | 3604 ± 1 |
| 2 | 5'-TCG₁AACG₁TTCG-X-GCTTG₁CAAG₁CT-5' | 6700 ± 7 | 6272 ± 24 | 2822 ± 24 |
| 3 | 5'-TCTCACCTTCT-X-TCTTCCACTCT-5' | 0 ± 0 | 80 ± 0 | 80 ± 0 |
| 4 | 5'-TCG₂AACG₂TTCG₂-X-G₂CTTG₂CAAG₂CT-5' | | | |
| 5 | 5'-TCG₂AACG₂TTCG-X-GCTTG₂CAAG₂CT-5' | | | |
| media | | 0 ± 0 | 78 ± 0 | 83 ± 0 |

| SEQ ID NO | Sequences and Modification (5'-3') | IFN-α (pg/ml) 10 μg/ml DN1 | IFN-α (pg/ml) 10 μg/ml DN2 | IFN-α (pg/ml) 10 μg/ml DN3 |
|---|---|---|---|---|
| 1 | 5'-TCG₁AACG₁TTCG₁-X-G₁CTTG₁CAAG₁CT-5' | 7038 ± 11 | 2921 ± 321 | 12514 ± 351 |

TABLE 3A-continued

Immunomer Structure and Immunostimulatory Activity in Human PBMC Assay (24 hs)

| | | | | |
|---|---|---|---|---|
| 2 | 5'-TCG$_1$AACG$_1$TTCG-X-GCTTG$_1$CAAG$_1$CT-5' | 7332 ± 269 | 3647 ± 704 | 10872 ± 613 |
| 3 | 5'-TCTCACCTTCT-X-TCTTCCACTCT-5' | 19 ± 7 | 0 ± 0 | 0 ± 0 |
| 4 | 5'-TCG$_2$AACG$_2$TTCG$_2$X-G$_2$CTTG$_2$CAAG$_2$CT-5' | | | |
| 5 | 5'-TCG$_2$AACG$_2$TTCG-X-GCTTG$_2$CAAG$_2$CT-5' | | | |
| media | | 33 ± 0 | 0 ± 0 | 0 ± 0 |

Normal phase represents a phosphorothioate linkage
$G_1$ = 2'-deoxy-7-deazaguanosine
$G_2$ = Arabinoguanosine
X = Glycerol linker

TABLE 3B

Immunomer Structure and Immunostimulatory Activity in Human PBMC Assay (24 hs)

| SEQ ID NO | Sequences and Modification (5'-3') | IFN-α (pg/ml) 10 µg/ml DN1 | IFN-α (pg/ml) 10 µg/ml DN2 | IFN-α (pg/ml) 10 µg/ml DN3 |
|---|---|---|---|---|
| 6 | 5'-TCG$_1$TCG$_1$AACG$_1$TTCG$_1$AGATGAT-3' | 3487 ± 1015 | 268 ± 3 | 3883 ± 50 |
| 7 | 5'-TCG$_2$TCG$_2$AACG$_2$TTCG$_2$AGATGAT-3' | 9 ± 0 | 30 ± 0 | 0 ± 0 |
| 8 | 5'-TCG$_3$TCG$_3$AACG$_3$TTCG$_3$AGATGAT-3' | 126 ± 1 | 0 ± 0 | 0 ± 0 |
| 9 | 5'-TC$_1$GTC$_1$GAAC$_1$GTTC$_1$GAGATGAT-3' | 0 ± 0 | 0 ± 0 | 0 ± 0 |
| 10 | 5'-TC$_2$GTC$_2$GAAC$_2$GTTC$_2$GAGATGAT-3' | 0 ± 0 | 20 ± 0 | 0 ± 0 |
| 11 | 5'-TC$_3$GTC$_3$GAAC$_3$GTTC$_3$GAGATGAT-3' | 11 ± 1 | 5 ± 0 | 76 ± 0 |
| media | | 33 ± 0 | 0 ± 0 | 0 ± 0 |

| SEQ ID NO | Sequences and Modification (5'-3') | IFN-α (pg/ml) 10 µg/ml DN4 | IFN-α (pg/ml) 10 µg/ml DN5 | IFN-α (pg/ml) 10 µg/ml DN6 |
|---|---|---|---|---|
| 6 | 5'-TCG$_1$TCG$_1$AACG$_1$TTCG$_1$AGATGAT-3' | 1950 ± 88 | 4342 ± 225 | 426 ± 85 |
| 7 | 5'-TCG$_2$TCG$_2$AACG$_2$TTCG$_2$AGATGAT-3' | 0 ± 0 | 1807 ± 0 | 31 ± 15 |
| 8 | 5'-TCG$_3$TCG$_3$AACG$_3$TTCG$_3$AGATGAT-3' | 0 ± 0 | 2876 ± 344 | 48 ± 5 |
| 9 | 5'-TC$_1$GTC$_1$GAAC$_1$GTTC$_1$GAGATGAT-3' | 0 ± 0 | 5 ± 0 | 4 ± 0 |
| 10 | 5'-TC$_2$GTC$_2$GAAC$_2$GTTC$_2$GAGATGAT-3' | 0 ± 0 | 8 ± 0 | 5 ± 3 |
| 11 | 5'-TC$_3$GTC$_3$GAAC$_3$GTTC$_3$GAGATGAT-3' | 0 ± 0 | 2111 ± 330 | 11 ± 3 |
| media | | 0 ± 0 | 48 ± 9 | 11 ± 2 |

Normal phase represents a phosphorothioate linkage
$G_1$ = 2'-deoxy-7-deazaguanosine
$G_2$ = Arabinoguanosine
$G_3$ = 2'-deoxyinosine
$C_1$ = 1-(2'-deoxy-β-D-ribofuranosyl)-2-oxo-7-deaza-8-methylpurine
$C_2$ = Arabinocytidine
$C_3$ = 2'-deoxy-5-hydroxycytidine

TABLE 3C

Immunomer Structure and Immunostimulatory Activity in Human PBMC Assay (24 hs)

| SEQ ID NO | Sequences and Modification (5'-3') | IFN-α (pg/ml) 10 µg/ml DN1 | IFN-α (pg/ml) 10 µg/ml DN2 | IFN-α (pg/ml) 10 µg/ml DN3 |
|---|---|---|---|---|
| 1 | 5'-TCG$_1$AACG$_1$TTCG$_1$-X-G$_1$CTTG$_1$CAAG$_1$CT-5' | 208 ± 33 | 432 ± 5 | 1345 ± 20 |
| 40 | 5'-TCG$_1$AACG$_1$TTCT-X-TCTTG$_1$CAAG$_1$CT-5' | 11 ± 1 | 59 ± 0 | 173 ± 41 |
| 12 | 5'-TCG$_1$AACG$_1$TTC-X-CTTG$_1$CAAG$_1$CT-5' | 16 ± 1 | 55 ± 7 | 324 ± 49 |
| 13 | 5'-TCG$_1$TTCG$_1$AACG$_1$-X-G$_1$CAAG$_1$CTTG$_1$CT-5' | 882 ± 32 | 733 ± 80 | 2035 ± 16 |
| 14 | 5'-TCCAACCTTCG-X-GCTTCCAACCT-5' | 50 ± 27 | 39 ± 17 | 4 ± 0 |
| 15 | 5'-TCG$_1$TTG$_1$CAACG$_1$-X-G$_1$CAACG$_1$TTG$_1$CT-5' | 604 ± 6 | 465 ± 70 | 1902 ± 30 |
| 4 | 5'-TCG$_2$AACG$_2$TTCG$_2$-X-G$_2$CTTG$_2$CAAG$_2$CT-5' | | | |
| 16 | 5'-TCG$_2$AACG$_2$TTCT-X-TCTTG$_2$CAAG$_2$CT-5' | | | |
| 17 | 5'-TCG$_1$AACG$_2$TTCG$_1$-X-G$_1$CTTG$_2$CAAG$_1$CT-5' | | | |
| 18 | 5'-TCG$_1$AAC$_1$GTTCG$_1$-X-G$_1$CTTGC$_1$AAG$_1$CT-5' | | | |
| media | | 20 ± 4 | 12 ± 0 | 3 ± 0 |

| SEQ ID NO | Sequences and Modification (5'-3') | IFN-α (pg/ml) 10 µg/ml DN4 | IFN-α (pg/ml) 10 µg/ml DN5 | IFN-α (pg/ml) 10 µg/ml DN6 |
|---|---|---|---|---|
| 1 | 5'-TCG$_1$AACG$_1$TTCG$_1$-X-G$_1$CTTG$_1$CAAG$_1$CT-5' | 900 ± 8 | 432 ± 26 | 582 ± 20 |
| 40 | 5'-TCG$_1$AACG$_1$TTCT-X-TCTTG$_1$CAAG$_1$CT-5' | 92 ± 6 | | |
| 12 | 5'-TCG$_1$AACG$_1$TTC-X-CTTG$_1$CAAG$_1$CT-5' | 441 ± 76 | | |
| 13 | 5'-TCG$_1$TTCG$_1$AACG$_1$-X-G$_1$CAAG$_1$CTTG$_1$CT-5' | 732 ± 8 | | |
| 14 | 5'-TCCAACCTTCG-X-GCTTCCAACCT-5' | 19 ± 5 | | |
| 15 | 5'-TCG$_1$TTG$_1$CAACG$_1$-X-G$_1$CAACG$_1$TTG$_1$CT-5' | 880 ± 8 | | |
| 4 | 5'-TCG$_2$AACG$_2$TTCG$_2$-X-G$_2$CTTG$_2$CAAG$_2$CT-5' | | 27 ± 0 | 26 ± 0 |
| 16 | 5'-TCG$_2$AACG$_2$TTCT-X-TCTTG$_2$CAAG$_2$CT-5' | | 19 ± 0 | 23 ± 0 |
| 17 | 5'-TCG$_1$AACG$_2$TTCG$_1$-X-G$_1$CTTG$_2$CAAG$_1$CT-5' | | | |
| 18 | 5'-TCG$_1$AAC$_1$GTTCG$_1$-X-G$_1$CTTGC$_1$AAG$_1$CT-5' | | | |
| media | | 6 ± 1 | 0 ± 0 | 0 ± 0 |

| SEQ ID NO | Sequences and Modification (5'-3') | IFN-α (pg/ml) 10 µg/ml DN7 | IFN-α (pg/ml) 10 µg/ml DN8 | IFN-α (pg/ml) 10 µg/ml DN9 |
|---|---|---|---|---|
| 1 | 5'-TCG$_1$AACG$_1$TTCG$_1$-X-G$_1$CTTG$_1$CAAG$_1$CT-5' | 324 ± 18 | 578 ± 28 | 741 ± 25 |
| 40 | 5'-TCG$_1$AACG$_1$TTCT-X-TCTTG$_1$CAAG$_1$CT-5' | | | |
| 12 | 5'-TCG$_1$AACG$_1$TTC-X-CTTG$_1$CAAG$_1$CT-5' | | | |
| 13 | 5'-TCG$_1$TTCG$_1$AACG$_1$-X-G$_1$CAAG$_1$CTTG$_1$CT-5' | | | |
| 14 | 5'-TCCAACCTTCG-X-GCTTCCAACCT-5' | | | |
| 15 | 5'-TCG$_1$TTG$_1$CAACG$_1$-X-G$_1$CAACG$_1$TTG$_1$CT-5' | | | |
| 4 | 5'-TCG$_2$AACG$_2$TTCG$_2$-X-G$_2$CTTG$_2$CAAG$_2$CT-5' | 6 ± 0 | | |
| 16 | 5'-TCG$_2$AACG$_2$TTCT-X-TCTTG$_2$CAAG$_2$CT-5' | 0 ± 0 | | |
| 17 | 5'-TCG$_1$AACG$_2$TTCG$_1$-X-G$_1$CTTG$_2$CAAG$_1$CT-5' | | | |

TABLE 3C-continued

Immunomer Structure and Immunostimulatory Activity in Human PBMC Assay (24 hs)

| | | | | |
|---|---|---|---|---|
| 18 | 5'-TCG₁AAC₁GTTCG₁-X-G₁CTTGC₁AAG₁CT-5' | | | |
| media | | 0 ± 0 | 0 ± 0 | 0 ± 0 |

Normal phase represents a phosphorothioate linkage
G₁ = 2'-deoxy-7-deazaguanosine
G₂ = Arabinoguanosine
C₁ = 1-(2'-deoxy-β-D-ribofuranosyl)-2-oxo-7-deaza-8-methylpurine
X = Glycerol Linker

TABLE 3D

Immunomer Structure and Immunostimulatoiy Activity in Human PBMC Assay (24 hs)

| SEQ ID NO | Sequences and Modification (5'-3') | IFN-α (pg/ml) 10 µg/ml DN1 | IFN-α (pg/ml) 10 µg/ml DN2 | IFN-α (pg/ml) 10 µg/ml DN3 |
|---|---|---|---|---|
| 19 | 5'-TCG₁AACG₂TTCG₁-X-G₁CTTG₂CAAG₁CT-5' | 8 ± 0 | 65 ± 3 | 314 ± 23 |
| 20 | 5'-TCG₁AAC₁GTTCG₁-X-G₁CTTGC₁AAG₁CT-5' | 9 ± 0 | 10 ± 2 | 487 ± 87 |
| 21 and 34 | 5'-TCG₁AACG₁TTCG₁-Y-TCTTG₁CTGTCT-5' | | | |
| 22 and 35 | 5'-TCG₁AACG₁TTCG₁-Y-TCTTG₂CTGTCT-5' | | | |
| 23 and 36 | 5'-TCG₁AACG₁TTCG₁-Y-TCTTGC₁TGTCT-5' | | | |
| 24 and 37 | 5'-TCG₁AACG₁TTCG₁-Y-TCTTCCACTCT-5' | | | |
| 25 and 34 | 5'-TG₁CAAG₁CTTG₁C-Y-TCTTG₁CTGTCT-5 | | | |
| 26 and 37 | 5'-TG₁CAAG₁CTTG₁C-Y-TCTTCCACTCT-5' | | | |
| 27 | 5'-TG₁CAAG₁CTTG₁C-X-CG₁TTCG₁AACG₁T-5' | | | |
| 28 | 5'-CTGTCG₂TTCTCo-X-oCTCTTG₂CTGTC-5' | | | |
| 29 | 5'-CTGTCoG₂TTCTC-X-CTCTTG₂oCTGTC-5' | | | |
| 30 | 5'-TCG₁TGTCG₁TTT-X-TTTG₁CTGTG₁CT-5' | | | |
| 31 | 5'-TG₁CTGTG₁CTTT-X-TTTCG₁TGTCG₁T-5' | | | |
| 32 and 38 | 5'-TCG₁AACG₁TTCG₁-Y-GACAG₁CTGTCT-5 | | | |
| 33 and 39 | 5'-TG₁CAACG₁CTTG₁C-Y-GACACG₁ TGTCT-5' | | | |
| Media | | 11 ± 0 | 10 ± 0 | 0 ± 0 |

| SEQ ID NO | Sequences and Modification (5'-3') | IFN-α (pg/ml) 10 µg/ml DN4 | IL-10 (pg/ml) 10 µg/ml DN5 | IL-10 (pg/ml) 10 µg/ml DN6 |
|---|---|---|---|---|
| 19 | 5'-TCG₁AACG₂TTCG₁-X-G₁CTTG₂CAAG₁CT-5' | 1446 ± 7 | | |
| 20 | 5'-TCG₁AAC₁GTTCG₁-X-G₁CTTGC₁AAG₁CT-5' | 942 ± 1 | | |
| 21 and 34 | 5'-TCG₁AACG₁TTCG₁-Y-TCTTG₁CTGTCT-5' | | 126 ± 2 | 159 ± 13 |
| 22 and 35 | 5'-TCG₁AACG₁TTCG₁-Y-TCTTG₂CTGTCT-5' | | 239 ± 23 | 356 ± 109 |
| 23 and 36 | 5'-TCG₁AACG₁TTCG₁-Y-TCTTGC₁TGTCT-5' | | 147 ± 23 | 185 ± 46 |
| 24 and 37 | 5'-TCG₁AACG₁TTCG₁-Y-TCTTCCACTCT-5' | | 107 ± 15 | 148 ± 37 |
| 25 and 34 | 5'-TG₁CAAG₁CTTG₁C-Y-TCTTG₁CTGTCT-5' | | | |
| 26 and 37 | 5'-TG₁CAAG₁CTTG₁C-Y-TCTTCCACTCT-5' | | | |
| 27 | 5'-TG₁CAAG₁CTTG₁C-X-CG₁TTCG₁AACG₁T-5' | | | |

TABLE 3D-continued

Immunomer Structure and Immunostimulatoiy Activity in Human PBMC Assay (24 hs)

| SEQ ID NO | Sequences and Modification (5'-3') | | | |
|---|---|---|---|---|
| 28 | 5'-CTGTCG$_2$TTCTCo-X-oCTCTTG$_2$CTGTC-5' | | | |
| 29 | 5'-CTGTCoG$_2$TTCTC-X-CTCTTG$_2$oCTGTC-5' | | | |
| 30 | 5'-TCG$_1$TGTCG$_1$TTT-X-TTTG$_1$CTGTG$_1$CT-5' | | | |
| 31 | 5'-TG$_1$CTGTG$_1$CTTT-X-TTTCG$_1$TGTCG$_1$T-5' | | | |
| 32 and 38 | 5'-TCG$_1$AACG$_1$TTCG$_1$-Y-GACAG$_1$CTGTCT-5 | | | |
| 33 and 39 | 5'-TG$_1$CAACG$_1$CTTG$_1$C-Y-GACACG$_1$ TGTCT-5' | | | |
| Media | | 0 ± 0 | 68 ± 5 | 67 ± 0 |

| SEQ ID NO | Sequences and Modification (5'-3') | IL-10 (pg/ml) 10 μg/ml DN7 | IFN-α (pg/ml) 10 μg/ml DN8 | IFN-α (pg/ml) 10 μg/ml DN9 |
|---|---|---|---|---|
| 19 | 5'-TCG$_1$AACG$_2$TTCG$_1$-X-G$_1$CTTG$_2$CAAG$_1$CT-5' | | | |
| 20 | 5'-TCG$_1$AAC$_1$GTTCG$_1$-X-G$_1$CTTGC$_1$AAG$_1$CT-5' | | | |
| 21 and 34 | 5'-TCG$_1$AACG$_1$TTCG$_1$-Y-TCTTG$_1$CTGTCT-5' | 242 ± 1 | 549 ± 37 | 9 ± 0 |
| 22 and 35 | 5'-TCG$_1$AACG$_1$TTCG$_1$-Y-TCTTG$_2$CTGTCT-5' | 241 ± 2 | 250 ± 12 | 14 ± 1 |
| 23 and 36 | 5'-TCG$_1$AACG$_1$TTCG$_1$-Y-TCTTGC$_1$TGTCT-5' | 238 ± 0 | 224 ± 25 | 8 ± 1 |
| 24 and 37 | 5'-TCG$_1$AACG$_1$TTCG$_1$-Y-TCTTCCACTCT-5' | 238 ± 10 | 668 ± 7 | 41 ± 0 |
| 25 and 34 | 5'-TG$_1$CAAG$_1$CTTG$_1$C-Y-TCTTG$_1$CTGTCT-5' | | | |
| 26 and 37 | 5'-TG$_1$CAAG$_1$CTTG$_1$C-Y-TCTTCCACTCT-5' | | | |
| 27 | 5'-TG$_1$CAAG$_1$CTTG$_1$C-X-CG$_1$TTCG$_1$AACG$_1$T-5' | | | |
| 28 | 5'-CTGTCG$_2$TTCTCo-X-oCTCTTG$_2$CTGTC-5' | 223 ± 31 | 12 ± 0 | |
| 29 | 5'-CTGTCoG$_2$TTCTC-X-CTCTTG$_2$oCTGTC-5' | 47 ± 4 | 5 ± 1 | |
| 30 | 5'-TCG$_1$TGTCG$_1$TTT-X-TTTG$_1$CTGTG$_1$CT-5' | | | |
| 31 | 5'-TG$_1$CTGTG$_1$CTTT-X-TTTCG$_1$TGTCG$_1$T-5' | | | |
| 32 and 38 | 5'-TCG$_1$AACG$_1$TTCG$_1$-Y-GACAG$_1$CTGTCT-5' | | | |
| 33 and 39 | 5'-TG$_1$CAACG$_1$CTTG$_1$C-Y-GACACG$_1$ TGTCT-5' | | | |
| Media | | 0 ± 0 | 0 ± 0 | 2 ± 0 |

| SEQ ID NO | Sequences and Modification (5'-3') | IFN-α (pg/ml) 10 μg/ml DN10 | IFN-α (pg/ml) 10 μg/ml DN11 | IFN-α (pg/ml) 10 μg/ml DN12 |
|---|---|---|---|---|
| 19 | 5'-TCG$_1$AACG$_2$TTCG$_1$-X-G$_1$CTTG$_2$CAAG$_1$CT-5' | | | |
| 20 | 5'-TCG$_1$AAC$_1$GTTCG$_1$-X-G$_1$CTTGC$_1$AAG$_1$CT-5' | | | |
| 21 and 34 | 5'-TCG$_1$AACG$_1$TTCG$_1$-Y-TCTTG$_1$CTGTCT-5' | 232 ± 8 | 252 ± 16 | |
| 22 and 35 | 5'-TCG$_1$AACG$_1$TTCG$_1$-Y-TCTTG$_2$CTGTCT-5' | 67 ± 1 | 195 ± 3 | 364 ± 8 |
| 23 and 36 | 5'-TCG$_1$AACG$_1$TTCG$_1$-Y-TCTTGC$_1$TGTCT-5' | 70 ± 1 | 148 ± 3 | |
| 24 and 37 | 5'-TCG$_1$AACG$_1$TTCG$_1$-Y-TCTTCCACTCT-5' | 443 ± 29 | 678 ± 133 | |
| 25 and 34 | 5'-TG$_1$CAAG$_1$CTTG$_1$C-Y-TCTTG$_1$CTGTCT-5' | | | 298 ± 16 |
| 26 and 37 | 5'-TG$_1$CAAG1 CTTG$_1$C-Y-TCTTCCACTCT-5' | | | 12 ± 1 |
| 27 | 5'-TG$_1$CAAG$_1$CTTG$_1$C-X-CG$_1$TTCG$_1$AACG$_1$T-5' | | | |

TABLE 3D-continued

Immunomer Structure and Immunostimulatoiy Activity in Human PBMC Assay (24 hs)

| | | | | |
|---|---|---|---|---|
| 28 | 5'-CTGTCG$_2$TTCTCo-X-oCTCTTG$_2$CTGTC-5' | 2 ± 0 | 94 ± 5 | 512 ± 33 |
| 29 | 5'-CTGTCoG$_2$TTCTC-X-CTCTTG$_2$oCTGTC-5' | 3 ± 0 | 61 ± 18 | 168 ± 25 |
| 30 | 5'-TCG$_1$TGTCG$_1$TTT-X-TTTG$_1$CTGTG$_1$CT-5' | | | 992 ± 2 |
| 31 | 5'-TG$_1$CTGTG$_1$CTTT-X-TTTCG$_1$TGTCG$_1$T-5' | | | 9 ± 0 |
| 32 and 38 | 5'-TCG$_1$AACG$_1$TTCG$_1$-Y-GACAG$_1$CTGTCT-5' | | | 1528 ± 20 |
| 33 and 39 | 5'-TG$_1$CAACG$_1$CTTG$_1$C-Y-GACACG$_1$ TGTCT-5' | | | 69 ± 10 |
| Media | | 0 ± 0 | 6 ± 0 | 7 ± 0 |

Normal phase represents a phosphorothioate linkage; o represents a phosphodiester linkage.
$G_1$ = 2'-deoxy-7-deazaguanosine
$G_2$ = Arabinoguanosine
$C_1$ = 1-(2'-deoxy-β-D-ribofuranosyl)-2-oxo-7-deaza-8-methylpurine
X = Glycerol Linker
Y = C3 Linker Example 10

Flow Cytometric Analysis

Cell surface markers of CD69 and CD86 were detected with a Coulter Epics-XL Flow Cytometer using anti-human CD69-Fitc and CD86-Fitc, which were purchased from BD Pharmingen (San Diego, USA). Staining methods were briefly described as follow. The activated culture cells were blocked with 10% Human AB serum (Sigma) in staining buffer (PBS with 1% BSA and 0.1% NaN$_3$) at 4° C. for 1 hour and stained with the antibodies at 4° C. overnight. PBMCs ($4\times10^5$) were stained with CD69-Fitc and CD86-Fitc. PDCs ($2\times10^5$) were stained CD86-Fitc. The cell staining data were acquired and analyzed with Coulter System II software (see Tables 4A-4F below).

TABLE 4A

Immunomer Structure and Expression of BC from Human PBMC ($2 \times 10^6$ cell/ml) (24 hs)

| SEQ ID NO | Sequences and Modification (5'-3') | % CD86 1 µg/ml DN1 | % CD86 1 µg/ml DN2 | % CD86 1 µg/ml DN3 |
|---|---|---|---|---|
| 1 | 5'-TCG$_1$AACG$_1$TTCG$_1$-X-G$_1$CTTG$_1$CAAG$_1$CT-5' | 36.4 | 17.7 | 36.4 |
| 2 | 5'-TCG$_1$AACG$_1$TTCG-X-GCTTG$_1$CAAG$_1$CT-5' | 27.2 | 6.3 | 30.4 |
| 3 | 5'-TCTCACCTTCT-X-TCTTCCACTCT-5' | 15 | 7.3 | 11.3 |
| 4 | 5'-TCG$_2$AACG$_2$TTCG$_2$-X-G$_2$CTTG$_2$CAAG$_2$CT-5' | | | |
| 5 | 5'-TCG$_2$AACG$_2$TTCG-X-GCTTG$_2$CAAG$_2$CT-5' | | | |
| media | | 10.7 | 8 | 7.6 |
| SEQ ID NO | Sequences and Modification (5'-3') | % CD86 1 µg/ml DN4 | % CD86 1 µg/ml DN5 | % CD86 1 µg/ml DN6 |
| 1 | 5'-TCG$_1$AACG$_1$TTCG$_1$-X-G$_1$CTTG$_1$CA.AG$_1$CT-5' | 33.3 | 12.9 | 27.6 |
| 2 | 5'-TCG$_1$AACG$_1$TTCG-X-GCTTG$_1$CAAG$_1$CT-5' | 25 | 17.5 | 32.4 |
| 3 | 5'-TCTCACCTTCT-X-TCTTCCACTCT-5' | 10 | 21.3 | 17.6 |
| 4 | 5'-TCG$_2$AACG$_2$TTCG$_2$-X-G$_2$CTTG$_2$CAAG$_2$CT-5' | | | |
| 5 | 5'-TCG$_2$AACG$_2$TTCG-X-GCTTG$_2$CAAG$_2$CT-5' | | | |
| media | | 5.2 | 5.4 | 11.8 |
| SEQ ID NO | Sequences and Modification (5'-3') | % CD69 1 µg/ml DN1 | % CD69 1 µg/ml DN2 | % CD69 1 µg/ml DN3 |
| 1 | 5'-TCG$_1$AACG$_1$TTCG$_1$-X-G$_1$CTTG$_1$CAAG$_1$CT-5' | 27.5 | 61 | 75.8 |
| 2 | 5'-TCG$_1$AACG$_1$TTCG-X-GCTTG$_1$CAAG$_1$CT-5' | 52.5 | 46.5 | 69.7 |

TABLE 4A-continued

Immunomer Structure and Expression of BC from Human PBMC
(2 × 10⁶ cell/ml) (24 hs)

| | | | | |
|---|---|---|---|---|
| 3 | 5'-TCTCACCTTCT-X-TCTTCCACTCT-5' | 0 | 11.8 | 8.5 |
| 4 | 5'-TCG₂AACG₂TTCG₂-X-G₂CTTG₂CAAG₂CT-5' | | | |
| 5 | 5'-TCG₂AACG₂TTCG-X-GCTTG₂CAAG₂CT-5' | | | |
| media | | 0 | 11.1 | 11.1 |

| SEQ ID NO | Sequences and Modification (5'-3') | % CD69 1 µg/ml | % CD69 1 µg/ml DN5 | % CD69 1 µg/ml |
|---|---|---|---|---|
| 1 | 5'-TCG₁AACG₁TTCG₁-X-G₁CTTG₁CAAG₁CT-5' | 58.3 | 51.8 | 39.1 |
| 2 | 5'-TCG₁AACG₁TTCG-X-GCTTG₁CAAG₁CT-5' | 62.5 | 56.5 | 43.6 |
| 3 | 5'-TCTCACCTTCT-X-TCTTCCACTCT-5' | 0 | 31.1 | 16.9 |
| 4 | 5'-TCG₂AACG₂TTCG₂-X-G₂CTTG₂CAAG₂CT-5' | | | |
| 5 | 5'-TCG₂AACG₂TTCG-X-GCTTG₂CAAG₂CT-5' | | | |
| media | | 5.2 | 18.9 | 8.9 |

Normal phase represents a phosphorothioate linkage
G₁ = 2'-deoxy-7-deazaguanosine
G₂ = Arabinoguanosine
X = Glycerol linker

TABLE 4B

Immunomer Structure and Expression of BC from Human PBMC
(2 × 10⁶ cell/ml) (24 hs)

| SEQ ID NO | Sequences and Modification (5'-3') | % CD86 1 µg/ml DN1 | % CD86 1 µg/ml DN2 | % CD86 1 µg/ml DN3 |
|---|---|---|---|---|
| 6 | 5'-TCG₁TCG₁AACG₁TTCG₁AGATGAT-3' | 43.4 | 25 | 34.6 |
| 7 | 5'-TCG₂TCG₂AACG₂TTCG₂AGATGAT-3' | 46.7 | 42.6 | 47.6 |
| 8 | 5'-TCG₃TCG₃AACG₃TTCG₃AGATGAT-3' | 41.1 | 25.7 | 38.5 |
| 9 | 5'-TC₁GTC₁GAAC₁GTTC₁GAGATGAT-3' | 25 | 20.8 | 27.6 |
| 10 | 5'-TC₂GTC₂GAAC₂GTTC₂GAGATGAT-3' | 36.4 | 22.2 | 26 |
| 11 | 5'-TC₃GTC₃GAAC₃GTTC₃GAGATGAT-3' | 30 | 17 | 22.2 |
| media | | 10.7 | 8 | 7.6 |

| SEQ ID NO | Sequences and Modification (5'-3') | % CD86 1 µg/ml DN4 | % CD86 1 µg/ml DN5 | % CD86 1 µg/ml DN6 |
|---|---|---|---|---|
| 6 | 5'-TCG₁TCG₁AACG₁TTCG₁AGATGAT-3' | 40 | 43.5 | 24.8 |
| 7 | 5'-TCG₂TCG₂AACG₂TTCG₂AGATGAT-3' | 36.4 | 41 | 36.2 |
| 8 | 5'-TCG₃TCG₃AACG₃TTCG₃AGATGAT-3' | 57.1 | 30.4 | 34.9 |
| 9 | 5'-TC₁GTC₁GAAC₁GTTC₁GAGATGAT-3' | 13.3 | 12.1 | 15.2 |
| 10 | 5'-TC₂GTC₂GAAC₂GTTC₂GAGATGAT-3' | 25 | 14.4 | 16.3 |
| 11 | 5'-TC₃GTC₃GAAC₃GTTC₃GAGATGAT-3' | 18.1 | 15 | 16.8 |
| media | | 5.2 | 3.9 | 6.8 |

| SEQ ID NO | Sequences and Modification (5'-3') | % CD69 1 µg/ml DN1 | % CD69 1 µg/ml DN2 | % CD69 1 µg/ml DN3 |
|---|---|---|---|---|
| 6 | 5'-TCG₁TCG₁AACG₁TTCG₁AGATGAT-3' | 56.4 | 43.8 | 68.7 |
| 7 | 5'-TCG₂TCG₂AACG₂TTCG₂AGATGAT-3' | 55.6 | 58.6 | 65.5 |

TABLE 4B-continued

Immunomer Structure and Expression of BC from Human PBMC
($2 \times 10^6$ cell/ml) (24 hs)

| | | | | |
|---|---|---|---|---|
| 8 | 5'-TCG$_3$TCG$_3$AACG$_3$TTCG$_3$AGATGAT-3' | 50 | 39.3 | 73.1 |
| 9 | 5'-TC$_1$GTC$_1$GAAC$_1$GTTC$_1$GAGATGAT-3' | 15.4 | 27 | 20 |
| 10 | 5'-TC$_2$GTC$_2$GAAC$_2$GTTC$_2$GAGATGAT-3' | 20 | 31.4 | 31.5 |
| 11 | 5'-TC$_3$GTC$_3$GAAC$_3$GTTC$_3$GAGATGAT-3' | 10 | 22.2 | 24.3 |
| media | | 0 | 11.1 | 11.1 |

| SEQ ID NO | Sequences and Modification (5'-3') | % CD69 1 µg/ml DN4 | % CD69 1 µg/ml DN5 | % CD69 1 µg/ml DN6 |
|---|---|---|---|---|
| 6 | 5'-TCG$_1$TCG$_1$AACG$_1$TTCG$_1$AGATGAT-3' | 57.1 | | |
| 7 | 5'-TCG$_2$TCG$_2$AACG$_2$TTCG$_2$AGATGAT-3' | 60 | | |
| 8 | 5'-TCG$_3$TCG$_3$AACG$_3$TTCG$_3$AGATGAT-3' | 37.5 | | |
| 9 | 5'-TC$_1$GTC$_1$GAAC$_1$GTTC$_1$GAGATGAT-3' | 15.4 | | |
| 10 | 5'-TC$_2$GTC$_2$GAAC$_2$GTTC$_2$GAGATGAT-3' | 11.1 | | |
| 11 | 5'-TC$_3$GTC$_3$GAAC$_3$GTTC$_3$GAGATGAT-3' | 14.3 | | |
| media | | 5.2 | | |

Normal phase represents a phosphorothioate linkage
$G_1$ = 2'-deoxy-7-deazaguanosine
$G_2$ = Arabinoguanosine
$G_3$ = 2'-deoxyinosine
$C_1$ = 1-(2'-deoxy-β-D-ribofuranosyl)-2-oxo-7-deaza-8-methylpurine
$C_2$ = Arabinocytidine
$C_3$ = 2'-deoxy-5-hydroxycytidine

TABLE 4C

Immunomer Structure and Expression of BC from Human PBMC
($2 \times 10^6$ cell/ml) (24 hs)

| SEQ ID NO | Sequences and Modification (5'-3') | % CD86 1 µg/ml DN1 | % CD86 1 µg/ml DN2 | % CD86 1 µg/ml DN3 |
|---|---|---|---|---|
| 1 | 5'-TCG$_1$AACG$_1$TTCG$_1$-X-G$_1$CTTG$_1$CAAG$_1$CT-5' | 32.3 | 34.8 | |
| 40 | 5'-TCG$_1$AACG$_1$TTCT-X-TCTTG$_1$CAAG$_1$CT-5' | 41.4 | 51.6 | |
| 12 | 5'-TCG$_1$AACG$_1$TTC-X-CTTG$_1$CAAG$_1$CT-5' | 33.3 | 51.5 | |
| 13 | 5'-TCG$_1$TTCG$_1$AACG$_1$-X-G$_1$CAAG$_1$CTTG$_1$CT-5' | 20 | 25.6 | |
| 14 | 5'-TCCAACCTTCG-X-GCTTCCAACCT-5' | 31.1 | 26.1 | |
| 15 | 5'-TCG$_1$TTG$_1$CAACG$_1$-X-G$_1$CAACG$_1$TTG$_1$CT-5' | 17.1 | 23.9 | |
| 4 | 5'-TCG$_2$AACG$_2$TTCG$_2$-X-G$_2$CTTG$_2$CAAG$_2$CT-5' | | | |
| 16 | 5'-TCG$_2$AACG$_2$TTCT-X-TCTTG$_2$CAAG$_2$CT-5' | | | |
| 17 | 5'-TCG$_1$AACG$_2$TTCG$_1$-X-G$_1$CTTG$_2$CAAG$_1$CT-5' | | | |
| 18 | 5'-TCG$_1$AAC$_1$GTTCG$_1$-X-G$_1$CTTGC$_1$AAG$_1$CT-5' | | | |
| media | | 19.4 | 20.9 | |

| SEQ ID NO | Sequences and Modification (5'-3') | % CD86 1 µg/ml DN4 | % CD86 1 µg/ml DN5 | % CD86 1 µg/ml DN6 |
|---|---|---|---|---|
| 1 | 5'-TCG$_1$AACG$_1$TTCG$_1$-X-G$_1$CTTG$_1$CAAG$_1$CT-5' | | 15.4 | 33.3 |
| 40 | 5'-TCG$_1$AACG$_1$TTCT-X-TCTTG$_1$CAAG$_1$CT-5' | | | |
| 12 | 5'-TCG$_1$AACG$_1$TTC-X-CTTG$_1$CAAG$_1$CT-5' | | | |

TABLE 4C-continued

Immunomer Structure and Expression of BC from Human PBMC
(2 × 10⁶ cell/ml) (24 hs)

| SEQ ID NO | Sequences and Modification (5'-3') | | |
|---|---|---|---|
| 13 | 5'-TCG$_1$TTCG$_1$AACG$_1$-X-G$_1$CAAG$_1$CTTG$_1$CT-5' | | |
| 14 | 5'-TCCAACCTTCG-X-GCTTCCAACCT-5' | | |
| 15 | 5'-TCG$_1$TTG$_1$CAACG$_1$-X-G$_1$CAACG$_1$TTG$_1$CT-5' | | |
| 4 | 5'-TCG$_2$AACG$_2$TTCG$_2$-X-G$_2$CTTG$_2$CAAG$_2$CT-5' | 30.7 | 45.4 |
| 16 | 5'-TCG$_2$AACG$_2$TTCT-X-TCTTG$_2$CAAG$_2$CT-5' | 30 | 41.6 |
| 17 | 5'-TCG$_1$AACG$_2$TTCG$_1$-X-G$_1$CTTG$_2$CAAG$_1$CT-5' | | |
| 18 | 5'-TCG$_1$AAC$_1$GTTCG$_1$-X-G$_1$CTTGC$_1$AAG$_1$CT-5' | | |
| media | | 8.6 | 2.7 |

| SEQ ID NO | Sequences and Modification (5'-3') | % CD86 1 µg/ml DN7 | % CD86 1 µg/ml DN8 | % CD86 1 µg/ml DN9 |
|---|---|---|---|---|
| 1 | 5'-TCG$_1$AACG$_1$TTCG$_1$-X-G$_1$CTTG$_1$CAAG$_1$CT-5' | 35.5 | 23.5 | 17.6 |
| 40 | 5'-TCG$_1$AACG$_1$TTCT-X-TCTTG$_1$CAAG$_1$CT-5' | | | |
| 12 | 5'-TCG$_1$AACG$_1$TTC-X-CTTG$_1$CAAG$_1$CT-5' | | | |
| 13 | 5'-TCG$_1$TTCG$_1$AACG$_1$-X-G$_1$CAAG$_1$CTTG$_1$CT-5' | | | |
| 14 | 5'-TCCAACCTTCG-X-GCTTCCAACCT-5' | | | |
| 15 | 5'-TCG$_1$TTG$_1$CAACG$_1$-X-G$_1$CAACG$_1$TTG$_1$CT-5' | | | |
| 4 | 5'-TCG$_2$AACG$_2$TTCG$_2$-X-G$_2$CTTG$_2$CAAG$_2$CT-5' | 56.5 | | |
| 16 | 5'-TCG$_2$AACG$_2$TTCT-X-TCTTG$_2$CAAG$_2$CT-5' | 46.7 | | |
| 17 | 5'-TCG$_1$AACG$_2$TTCG$_1$-X-G$_1$CTTG$_2$CAAG$_1$CT-5' | | | |
| 18 | 5'-TCG$_1$AAC$_1$GTTCG$_1$-X-G$_1$CTTGC$_1$AAG$_1$CT-5' | | | |
| media | | 9 | 20 | 15.3 |

| SEQ ID NO | Sequences and Modification (5'-3') | % CD69 1 µg/ml DN1 | % CD69 1 µg/ml DN2 | % CD69 1 µg/ml DN3 |
|---|---|---|---|---|
| 1 | 5'-TCG$_1$AACG$_1$TTCG$_1$-X-G$_1$CTTG$_1$CAAG$_1$CT-5' | 23.5 | 64 | |
| 40 | 5'-TCG$_1$AACG$_1$TTCT-X-TCTTG$_1$CAAG$_1$CT-5' | 20.8 | 62.5 | |
| 12 | 5'-TCG$_1$AACG$_1$TTC-X-CTTG$_1$CAAG$_1$CT-5' | 13.6 | 59 | |
| 13 | 5'-TCG$_1$1TCG$_1$AACG$_1$-X-G$_1$CAAG$_1$CTTG$_1$CT-5' | 12.5 | 46.4 | |
| 14 | 5'-TCCAACCTTCG-X-GCTTCCAACCT-5' | 15.9 | 52.9 | |
| 15 | 5'-TCG$_1$TTG$_1$CAACG$_1$-X-G$_1$CAACG$_1$TTG$_1$CT-5' | 12.2 | 51.6 | |
| 4 | 5'-TCG$_2$AACG$_2$TTCG$_2$-X-G$_2$CTTG$_2$CAAG$_2$CT-5' | | | |
| 16 | 5'-TCG$_2$AACG$_2$TTCT-X-TCTTG$_2$CAAG$_2$CT-5' | | | |
| 17 | 5'-TCG$_1$AACG$_2$TTCG$_1$-X-G$_1$CTTG$_2$CAAG$_1$CT-5' | | | |
| 18 | 5'-TCG$_1$AAC$_1$GTTCG$_1$-X-G$_1$CTTGC$_1$AAG$_1$CT-5' | | | |
| media | | 14.8 | 34 | |

| SEQ ID NO | Sequences and Modification (5'-3') | % CD69 1 µg/ml DN4 | % CD69 1 µg/ml DN5 | % CD69 1 µg/ml DN6 |
|---|---|---|---|---|
| 1 | 5'-TCG$_1$AACG$_1$TTCG$_1$-X-G$_1$CTTG$_1$CAAG$_1$CT-5' | | 53.8 | 62.5 |
| 40 | 5'-TCG$_1$AACG$_1$TTCT-X-TCTTG$_1$CAAG$_1$CT-5' | | | |
| 12 | 5'-TCG$_1$AACG$_1$TTC-X-CTTG$_1$CAAG$_1$CT-5' | | | |
| 13 | 5'-TCG$_1$TTCG$_1$AACG$_1$-X-G$_1$CAAG$_1$CTTG$_1$CT-5' | | | |

TABLE 4C-continued

Immunomer Structure and Expression of BC from Human PBMC
(2 × 10⁶ cell/ml) (24 hs)

| SEQ ID NO | Sequences and Modification (5'-3') | | |
|---|---|---|---|
| 14 | 5'-TCCAACCTTCG-X-GCTTCCAACCT-5' | | |
| 15 | 5'-TCG$_1$TTG$_1$CAACG$_1$-X-G1CAACG$_1$TTG$_1$CT-5' | | |
| 4 | 5'-TCG$_2$AACG$_2$TTCG$_2$-X-G$_2$CTTG$_2$CAAG$_2$CT-5' | 77.7 | 70.6 |
| 16 | 5'-TCG$_2$AACG$_2$TTCT-X-TCTTG$_2$CAAG$_2$CT-5' | 57.1 | 64.7 |
| 17 | 5'-TCG$_1$AACG$_2$TTCG$_1$-X-G$_1$CTTG$_2$CAAG$_1$CT-5' | | |
| 18 | 5'-TCG$_1$AAC$_1$GTTCG$_1$-X-G$_1$CTTGC$_1$AAG$_1$CT-5' | | |
| media | | 26.3 | 15 |

| SEQ ID NO | Sequences and Modification (5'-3') | % CD69 1 μg/ml DN7 | % CD69 1 μg/ml DN8 | % CD69 1 μg/ml DN9 |
|---|---|---|---|---|
| 1 | 5'-TCG$_1$AACG$_1$TTCG$_1$-X-G$_1$CTTG$_1$CAAG$_1$CT-5' | 28.6 | 50 | 25 |
| 40 | 5'-TCG$_1$AACG$_1$TTCT-X-TCTTG$_1$CAAG$_1$CT-5' | | | |
| 12 | 5'-TCG$_1$AACG$_1$TTC-X-CTTG$_1$CAAG$_1$CT-5 | | | |
| 13 | 5'-TCG$_1$TTCG$_1$AACG$_1$-X-G$_1$CAAG$_1$CTTG$_1$CT-5' | | | |
| 14 | 5'-TCCAACCTTCG-X-GCTTCCAACCT-5' | | | |
| 15 | 5'-TCG$_1$TTG$_1$CAACG$_1$-X-G$_1$CAACG$_1$TTG$_1$CT-5' | | | |
| 4 | 5'-TCG$_2$AACG$_2$TTCG$_2$-X-G$_2$CTTG$_2$CAAG$_2$CT-5' | 70.6 | | |
| 16 | 5'-TCG$_2$AACG$_2$TTCT-X-TCTTG$_2$CAAG$_2$CT-5' | 72.7 | | |
| 17 | 5'-TCG$_1$AACG$_2$TTCG$_1$-X-G$_1$CTTG$_2$CAAG$_1$CT-5' | | | |
| 18 | 5'-TCG$_1$AAC$_1$GTTCG$_1$-X-G$_1$CTTGC$_1$AAG$_1$CT-5' | | | |
| media | | 14.1 | 13.2 | 12 |

Normal phase represents a phosphorothioate linkage
$G_1$ = 2'-deoxy-7-deazaguanosine
$G_2$ = Arabinoguanosine
$C_1$ = 1-(2'-deoxy-β-D-ribofuranosyl)-2-oxo-7-deaza-8-methylpurine
X = Glycerol Linker

TABLE 4D

Immunomer Structure and Expression of BC from Human PBMC
(2 × 10⁶ cell/ml) (24 hs)

| SEQ ID NO | Sequences and Modification (5'-3') | % CD86 1 μg/ml DN1 | % CD86 1 μg/ml DN2 | % CD86 1 μg/ml DN3 |
|---|---|---|---|---|
| 1 | 5'-TCG$_1$AACG$_1$TTCG$_1$-X-G$_1$CTTG$_1$CAAG$_1$CT-5' | | 64.3 | 57.2 |
| 40 | 5'-TCG$_1$AACG$_1$TTCT-X-TCTTG$_1$CAAG$_1$CT-5' | | 59.2 | 58.3 |
| 12 | 5'-TCG$_1$AACG$_1$TTC-X-CTTG$_1$CAAG$_1$CT-5' | | 49.3 | 40.9 |
| 13 | 5'-TCG$_1$TTCG$_1$AACG$_1$-X-G$_1$CAAG$_1$CTTG$_1$CT-5' | | 25.3 | 24.7 |
| 14 | 5'-TCCAACCTTCG-X-GCTTCCAACCT-5' | | 15.4 | 17.2 |
| 15 | 5'-TCG$_1$TTG$_1$CAACG$_1$-X-G$_1$CAACG$_1$TTG$_1$CT-5' | | 30.6 | 23.7 |
| 4 | 5'-TCG$_2$AACG$_2$TTCG$_2$-X-G$_2$CTTG$_2$CAAG$_2$CT-5' | | | |
| 16 | 5'-TCG$_2$AACG$_2$TTCT-X-TCTTG$_2$CAAG$_2$CT-5' | | | |
| 17 | 5'-TCG$_1$AACG$_2$TTCG$_1$-X-G$_1$CTTG$_2$CAAG$_1$CT-5' | | | |
| 18 | 5'-TCG$_1$AAC$_1$GTTCG$_1$-X-G$_1$CTTGC$_1$AAG$_1$CT-5' | | | |

TABLE 4D-continued

Immunomer Structure and Expression of BC from Human PBMC
(2 × 10⁶ cell/ml) (24 hs)

| | | | | |
|---|---|---|---|---|
| media | | | 2.6 | 13.9 |

| SEQ ID NO | Sequences and Modification (5'-3') | % CD86 1 µg/ml DN4 | % CD86 1 µg/ml DN5 | % CD86 1 µg/ml DN6 |
|---|---|---|---|---|
| 1 | 5'-TCG₁AACG₁TTCG₁-X-G₁CTTG₁CAAG₁CT-5' | 35.9 | 30.3 | 35.6 |
| 40 | 5'-TCG₁AACG₁TTCT-X-TCTTG₁CAAG₁CT-5' | 57.9 | | |
| 12 | 5'-TCG₁AACG₁TTC-X-CTTG₁CAAG₁CT-5' | 34.9 | | |
| 13 | 5'-TCG₁TCG₁AACG₁-X-G₁CAAG₁CTTG₁CT-5' | | | |
| 14 | 5'-TCCAACCTTCG-X-GCTTCCAACCT-5' | | | |
| 15 | 5'-TCG₁TTG₁CAACG₁-X-G₁CAACG₁TTG₁CT-5' | | | |
| 4 | 5'-TCG₂AACG₂TTCG₂-X-G₂CTTG₂CAAG₂CT-5' | | | |
| 16 | 5'-TCG₂AACG₂TTCT-X-TCTTG₂CAAG₂CT-5' | | | |
| 17 | 5'-TCG₁AACG₂TTCG₁-X-G₁CTTG₂CAAG₁CT-5' | | | |
| 18 | 5'-TCG₁AAC₁GTTCG₁-X-G₁CTTGC₁AAG₁CT-5' | | | |

| | | | | |
|---|---|---|---|---|
| media | | 12.3 | 11.1 | 14 |

| SEQ ID NO | Sequences and Modification (5'-3') | % CD86 1 µg/ml DN7 | % CD86 1 µg/ml DN8 | % CD86 1 µg/ml DN9 |
|---|---|---|---|---|
| 1 | 5'-TCG₁AACG₁TTCG₁-X-G₁CTTG₁CAAG₁CT-5' | | 28 | 32.3 |
| 40 | 5'-TCG₁AACG₁TTCT-X-TCTTG₁CAAG₁CT-5' | | | |
| 3 | 5'-TCG₁AACG₁TTC-X-CTTG₁CAAG₁CT-5' | | | |
| 4 | 5'-TCGlTTCG₁AACG₁-X-GlCAAG₁CTTG₁CT-5' | | | |
| 5 | 5'-TCCAACCTTCG-X-GCTTCCAACCT-5' | | | |
| 6 | 5'-TCG₁TTG₁CAACG₁-X-G₁CAACG₁TTG₁CT-5' | | | |
| 7 | 5'-TCG₂AACG₂TTCG₂-XG₂CTTG₂CAAG₂CT-5' | | | |
| 8 | 5'-TCG₂AACG₂TTCT-X-TCTTG₂CAAG₂CT-5' | | | |
| 9 | 5'-TCG₁AACG₂TTCG₁-X-G₁CTTG₂CAAG₁CT-5' | | | |
| 10 | 5'-TCG₁AAC₁GTTCG₁-X-G₁CTTGC₁AAG₁CT-5' | | | |

| | | | | |
|---|---|---|---|---|
| media | | | 10.9 | 12.6 |

Normal phase represents a phosphorothioate linkage
G₁ = 2'-deoxy-7-deazaguanosine
G₂ = Arabinoguanosine
C₁ = 1-(2'-deoxy-β-D-ribofuranosyl)-2-oxo-7-deaza-8-methylpurine
X = Glycerol Linker

TABLE 4E

Immunomer Structure and Expression of BC from Human PBMC assay
(24 hs)

| SEQ ID NO | Sequences and Modification (5'-3') | % CD86 1 µg/ml DN1 | % CD86 1 µg/ml DN2 | % CD86 1 µg/ml DN3 |
|---|---|---|---|---|
| 19 | 5'-TCG₁AACG₂TTCG₁-X-G₁CTTG₂CAAG₁CT-5' | 20 | 9 | 34.6 |
| 20 | 5'-TCG₁AAC₁GTTCG₁-X-G₁CTTGC₁AAG₁CT-5' | 21.7 | 12.5 | 31.4 |
| 21 and 34 | 5'-TCG₁AACG₁TTCG₁-Y-TCTTG₁CTGTCT-5' | | | |

TABLE 4E-continued

Immunomer Structure and Expression of BC from Human PBMC assay
(24 hs)

| SEQ ID NO | Sequences and Modification (5'-3') |
|---|---|
| 22 and 35 | 5'-TCG$_1$AACG$_1$TTCG$_1$-Y-TCTTG$_2$CTGTCT-5' |
| 23 and 36 | 5'-TCG$_1$AACG$_1$TTCG$_1$-Y-TCTTGC$_1$TGTCT-5' |
| 24 and 37 | 5'-TCG$_1$AACG$_1$TTCG$_1$-Y-TCTTCCACTCT-5' |
| 25 and 34 | 5'-TG$_1$CAAG$_1$CTTG$_1$C-Y-TCTTG$_1$CTGTCT-5' |
| 26 and 37 | 5'-TG$_1$CAAG$_1$CTTG$_1$C-Y-TCTTCCACTCT-5' |
| 27 | 5'-TG$_1$CAAG$_1$CTTG$_1$C-X-CG$_1$TTCG$_1$AACG$_1$T-5' |
| 28 | 5'-CTGTCG$_2$TTCTCo-X-oCTCTTG$_2$CTGTC-5' |
| 29 | 5'-CTGTCoG$_2$TTCTC-X-CTCTTG$_2$oCTGTC-5' |
| 30 | 5'-TCG$_1$TGTCG$_1$TTT-X-TTTG$_1$CTGTG$_1$CT-5' |
| 31 | 5'-TG$_1$CTGTG$_1$CTTT-X-TTTCG$_1$TGTCG$_1$T-5' |
| 32 and 38 | 5'-TCG$_1$AACG$_1$TTCG$_1$-Y-GACAG$_1$CTGTCT-5' |
| 33 and 39 | 5'-TG$_1$CAACG$_1$CTTG$_1$C-Y-GACACG$_1$ TGTCT-5' |
| Media | 8.7 |

| SEQ ID NO | Sequences and Modification (5'-3') | % CD86 1 μg/ml DN4 | % CD86 1 μg/ml DN5 | % CD86 1 μg/ml DN6 |
|---|---|---|---|---|
| 19 | 5'-TCG$_1$AACG$_2$TTCG$_1$-X-G$_1$CTTG$_2$CAAG$_1$CT-5' | 42.3 | | |
| 20 | 5'-TCG$_1$AAC$_1$GTTCG$_1$-X-G$_1$CTTGC$_1$AAG$_1$CT-5' | 72.7 | | |
| 21 and 34 | 5'-TCG$_1$AACG$_1$TTCG$_1$-Y-TCTTG$_1$CTGTCT-5' | | 14.5 | 17.1 |
| 22 and 35 | 5'-TCG$_1$AACG$_1$TTCG$_1$-Y-TCTTG$_2$CTGTCT-5' | | 27.8 | 28.6 |
| 23 and 36 | 5'-TCG$_1$AACG$_1$TTCG$_1$-Y-TCTTGC$_1$TGTCT-5' | | 28.9 | 22.2 |
| 24 and 37 | 5'-TCG$_1$AACG$_1$TTCG$_1$-Y-TCTTCCACTCT-5' | | 23.2 | 21.8 |
| 25 and 34 | 5'-TG$_1$CAAG$_1$CTTG$_1$C-Y-TCTTG$_1$CTGTCT-5' | | | |
| 26 and 37 | 5'-TG$_1$CAAG$_1$CTTG$_1$C-Y-TCTTCCACTCT-5' | | | |
| 27 | 5'-TG$_1$CAAG$_1$CTTG$_1$C-X-CG$_1$TTCG$_1$AACG$_1$T-5' | | | |
| 28 | 5'-CTGTCG$_2$TTCTCo-X-oCTCTTG$_2$CTGTC-5' | | | |
| 29 | 5'-CTGTCoG$_2$TTCTC-X-CTCTTG$_2$oCTGTC-5' | | | |
| 30 | 5'-TCG$_1$TGTCG$_1$TTT-X-TTTG$_1$CTGTG$_1$CT-5' | | | |
| 31 | 5'-TG$_1$CTGTG$_1$CTTT-X-TTTCG$_1$TGTCG$_1$T-5' | | | |
| 32 and 38 | 5'-TCG$_1$AACGJTCG$_1$-Y-GACAG$_1$CTGTCT-5' | | | |
| 33 and 39 | 5'-TG$_1$CAACG$_1$CTTG$_1$C-Y-GACACG$_1$ TGTCT-5 | | | |
| Media | | 5.9 | 4.0 | 6.0 |

| SEQ ID NO | Sequences and Modification (5'-3') | % CD86 1 μg/ml DN7 | % CD86 1 μg/ml DN8 | % CD86 1 μg/ml DN9 |
|---|---|---|---|---|
| 19 | 5'-TCG$_1$AACG$_2$TTCG$_1$-X-G$_1$CTTG$_2$CkAG$_1$CT-5' | | | |
| 20 | 5'-TCG$_1$AAC$_1$GTTCG$_1$-X-G$_1$CTTGC$_1$AAG$_1$CT-5' | | | |
| 21 and 34 | 5'-TCG$_1$AACG$_1$TTCG$_1$-Y-TCTTG$_1$CTGTCT-5' | 65 | 46.3 | 40.3 |
| 22 and 35 | 5'-TCG$_1$AACG$_1$TTCG$_1$-Y-TCTTG$_2$CTGTCT-5' | 75 | 49.2 | 46.5 |
| 23 and 36 | 5'-TCG$_1$AACG$_1$TTCG$_1$-Y-TCTTGC$_1$TGTCT-5' | 78.9 | 54.3 | 45 |
| 24 and 37 | 5'-TCG$_1$AACG$_1$TTCG$_1$-Y-TCTTCCACTCT-5' | 83.3 | 33.8 | 29.4 |

TABLE 4E-continued

Immunomer Structure and Expression of BC from Human PBMC assay (24 hs)

| SEQ ID NO | Sequences and Modification (5'-3') | | |
|---|---|---|---|
| 25 and 34 | 5'-TG$_1$CAAG$_1$CTTG$_1$C-Y-TCTTG$_1$CTGTCT-5' | | |
| 26 and 37 | 5'-TG$_1$CAAG$_1$CTTG$_1$C-Y-TCTTCCACTCT-5' | | |
| 27 | 5'-TG$_1$CAAG$_1$CTTG$_1$C-X-CG$_1$TTCG$_1$AACG$_1$T-5' | | |
| 28 | 5'-CTGTCG$_2$TTCTCo-X-oCTCTTG$_2$CTGTC-5' | 22.5 | 35.6 |
| 29 | 5'-CTGTCoG$_2$TTCTC-X-CTCTTG$_2$oCTGTC-5' | 43.1 | 47.8 |
| 30 | 5'-TCG$_1$TGTCG$_1$TTT-X-TTTG$_1$CTGTG$_1$CT-5' | | |
| 31 | 5'-TG$_1$CTGTG$_1$CTTT-X-TTTCG$_1$TGTCG$_1$T-5' | | |
| 32 and 38 | 5'-TCG$_1$AACG$_1$TTCG$_1$-Y-GACAG$_1$CTGTCT-5' | | |
| 33 and 39 | 5'-TG$_1$CAACG$_1$CTTG$_1$C-Y-GACACG$_1$ TGTCT-5' | | |
| Media | | 4.6 | 0 | 10.5 |

| SEQ ID NO | Sequences and Modification (5'-3') | % CD86 1 µg/ml DN10 | % CD86 1 µg/ml DN11 | % CD86 1 µg/ml DN12 |
|---|---|---|---|---|
| 19 | 5'-TCG$_1$AACG$_2$TTCG$_1$-X-G$_1$CTTG$_2$CAAG$_1$CT-5' | | | |
| 20 | 5'-TCG$_1$AAC$_1$GTTCG$_1$-X-G$_1$CTTGC$_1$AAG$_1$CT-5' | | | |
| 21 and 34 | 5'-TCG$_1$AACG$_1$TTCG$_1$-Y-TCTTG$_1$CTGTCT-5' | 24.4 | 60.7 | |
| 22 and 35 | 5'-TCG$_1$AACG$_1$TTCG$_1$-Y-TCTTG$_2$CTGTCT-5' | 23.9 | 61.5 | 53.8 |
| 23 and 36 | 5'-TCG$_1$AACG$_1$TTCG$_1$-Y-TCTTGC$_1$TGTCT-5' | 32.8 | 72 | |
| 24 and 37 | 5'-TCG$_1$AACG$_1$TTCG$_1$-Y-TCTTCCACTCT-5' | 22.7 | 52.6 | |
| 25 and 34 | 5'-TG$_1$CAAG$_1$CTTG$_1$C-Y-TCTTG$_1$CTGTCT-5' | | | 31.7 |
| 26 and 37 | 5'-TG$_1$CAAG$_1$CTTG$_1$C-Y-TCTTCCACTCT-5' | | | 23.9 |
| 27 | 5'-TG$_1$CAAG$_1$CTTG$_1$C-X-CG$_1$TTCG$_1$AACG$_1$T-5' | | | |
| 28 | 5'-CTGTCG$_2$TTCTCo-X-oCTCTTG$_2$CTGTC-5' | 21 | 57.1 | 29.6 |
| 29 | 5'-CTGTCoG$_2$TTCTC-X-CTCTTG$_2$oCTGTC-5' | 34.7 | 63.1 | 43.5 |
| 30 | 5'-TCG$_1$TGTCG$_1$TTT-X-TTTG$_1$CTGTG$_1$CT-5' | | | 24.5 |
| 31 | 5'-TG$_1$CTGTG$_1$CTTT-X-TTTCG$_1$TGTCG$_1$T-5' | | | 28.6 |
| 32 and 38 | 5'-TCG$_1$AACG$_1$TTCG$_1$-Y-GACAG$_1$CTGTCT-5' | | | 44.2 |
| 33 and 39 | 5'-TG$_1$CAACG$_1$CTTG$_1$C-Y-GACACG$_1$ TGTCT-5' | | | 28.3 |
| Media | | 19 | 8.6 | 18 |

| SEQ ID NO | Sequences and Modification (5'-3') | % CD69 1 µg/ml DN1 | % CD69 1 µg/ml DN2 | % CD69 1 µg/ml DN3 |
|---|---|---|---|---|
| 19 | 5'-TCG$_1$AACG$_2$TTCG$_1$-X-G$_1$CTTG$_2$CAAG$_1$CT-5' | 13 | 22.2 | 19.2 |
| 20 | 5'-TCG$_1$AAC$_1$GTTCG$_1$-X-G$_1$CTTGC$_1$AAG$_1$CT-5' | 52 | 30.7 | 59.3 |
| 21 and 34 | 5'-TCG$_1$AACG$_1$TTCG$_1$-Y-TCTTG$_1$CTGTCT-5' | | | |
| 22 and 35 | 5'-TCG$_1$AACG$_1$TTCG$_1$-Y-TCTTG$_2$CTGTCT-5' | | | |
| 23 and 36 | 5'-TCG$_1$AACG$_1$TTCG$_1$-Y-TCTTGC$_1$TGTCT-5' | | | |
| 24 and 37 | 5'-TCG$_1$AACG$_1$TTCG$_1$-Y-TCTTCCACTCT-5' | | | |
| 25 and 34 | 5'-TG$_1$CAAGl CTTG$_1$C-Y-TCTTG$_1$CTGTCT-5' | | | |
| 26 and 37 | 5'-TG$_1$CAAG$_1$CTTG$_1$C-Y-TCTTCCACTCT-5' | | | |
| 27 | 5'-TG$_1$CAAG$_1$CTTG$_1$C-X-CG$_1$TTCG$_1$AACG$_1$T-5' | | | |

TABLE 4E-continued

Immunomer Structure and Expression of BC from Human PBMC assay
(24 hs)

| SEQ ID NO | Sequences and Modification (5'-3') |
|---|---|
| 28 | 5'-CTGTCG$_2$TTCTCo-X-oCTCTTG$_2$CTGTC-5' |
| 29 | 5'-CTGTCoG$_2$TTCTC-X-CTCTTG$_2$oCTGTC-5' |
| 30 | 5'-TCG$_1$TGTCG$_1$TTT-X-TTTG$_1$CTGTG$_1$CT-5' |
| 31 | 5'-TG$_1$CTGTG$_1$CTTT-X-TTTCG$_1$TGTCG$_1$T-5' |
| 32 and 38 | 5'-TCG$_1$AACG$_1$TTCG$_1$-Y-GACAG$_1$CTGTCT-5' |
| 33 and 39 | 5'-TG$_1$CAACG$_1$CTTG$_1$C-Y-GACACG$_1$ TGTCT-5' |
| Media | 3 |

| SEQ ID NO | Sequences and Modification (5'-3') | % CD69 1 µg/ml DN4 | % CD69 1 µg/ml DN5 | % CD69 1 µg/ml DN6 |
|---|---|---|---|---|
| 19 | 5'-TCG$_1$AACG$_2$TTCG$_1$-X-G$_1$CTTG$_2$CAAG$_1$CT-5' | 76 | | |
| 20 | 5'-TCG$_1$AAC$_1$GTTCG$_1$-X-G$_1$CTTGC$_1$AAG$_1$CT-5' | 85.1 | | |
| 21 and 34 | 5'-TCG$_1$AACG$_1$TTCG$_1$-Y-TCTTG$_1$CTGTCT-5' | | 35 | 20 |
| 22 and 35 | 5'-TCG$_1$AACG$_1$TTCG$_1$-Y-TCTTG$_2$CTGTCT-5' | | 57.3 | 39.4 |
| 23 and 36 | 5'-TCG$_1$AACG$_1$TTCG$_1$-Y-TCTTGC$_1$TGTCT-5' | | 60.4 | 54.2 |
| 24 and 37 | 5'-TCG$_1$AACG$_1$TTCG$_1$-Y-TCTTCCACTCT-5' | | 69 | 30.2 |
| 25 and 34 | 5'-TG$_1$CAAG$_1$CTTG$_1$C-Y-TCTTG$_1$CTGTCT-5' | | | |
| 26 and 37 | 5'-TG$_1$CAAG$_1$CTTG$_1$C-Y-TCTTCCACTCT-5' | | | |
| 27 | 5'-TG$_1$CAAG$_1$CTTG$_1$C-X-CG$_1$TTCG$_1$AACG$_1$T-5' | | | |
| 28 | 5'-CTGTCG$_2$TTCTCo-X-oCTCTTG$_2$CTGTC-5' | | | |
| 29 | 5'-CTGTCoG$_2$TTCTC-X-CTCTTG$_2$oCTGTC-5' | | | |
| 30 | 5-TCG$_1$TGTCG$_1$TTT-X-TTTG$_1$CTGTG$_1$CT-5' | | | |
| 31 | 5'-TG$_1$CTGTG$_1$CTTT-X-TTTCG$_1$TGTCG$_1$T-5' | | | |
| 32 and 38 | 5'-TCG$_1$AACG$_1$TTCG$_1$-Y-GACAG$_1$CTGTCT-5' | | | |
| 33 and 39 | 5'-TG$_1$CAACG$_1$CTTG$_1$C-Y-GACACG$_1$ TGTCT-5' | | | |
| Media | | 10 | 5.9 | 10.1 |

| SEQ ID NO | Sequences and Modification (5'-3') | % CD69 1 µg/ml DN7 | % CD69 1 µg/ml DN8 | % CD69 1 µg/ml DN9 |
|---|---|---|---|---|
| 19 | 5'-TCG$_1$AACG$_2$TTCG$_1$-X-G$_1$CTTG$_2$CAAG$_1$CT-5' | | | |
| 20 | 5'-TCG$_1$AAC$_1$GTTCG$_1$-X-G$_1$CTTGC$_1$AAG$_1$CT-5' | | | |
| 21 and 34 | 5'-TCG$_1$AACG$_1$TTCG$_1$-Y-TCTTG$_1$CTGTCT-5' | 88.2 | 47.7 | 59.7 |
| 22 and 35 | 5'-TCG$_1$AACG$_1$TTCG$_1$-Y-TCTTG$_2$CTGTCT-5' | 97 | 55 | 63.3 |
| 23 and 36 | 5'-TCG$_1$AACG$_1$TTCG$_1$-Y-TCTTGC$_1$TGTCT-5' | 96.8 | 68.3 | 60.2 |
| 24 and 37 | 5'-TCG$_1$AACG$_1$TTCG$_1$-Y-TCTTCCACTCT-5' | 91.9 | 40.3 | 41.9 |
| 25 and 34 | 5'-TG$_1$CAAG$_1$CTTG$_1$C-Y-TCTTG$_1$CTGTCT-5' | | | |
| 26 and 37 | 5'-TG$_1$CAAG$_1$CTTG$_1$C-Y-TCTTCCACTCT-5' | | | |
| 27 | 5'-TG$_1$CAAG$_1$CTTG$_1$C-X-CG$_1$1TCG$_1$AACG$_1$T-5' | | | |
| 28 | 5'-CTGTCG$_2$TTCTCo-X-oCTCTTG$_2$CTGTC-5' | | 36 | 51.2 |
| 29 | 5'-CTGTCoG$_2$TTCTC-X-CTCTTG$_2$oCTGTC-5' | | 51.6 | 66.7 |
| 30 | 5'-TCG$_1$TGTCG$_1$TTT-X-TTTG$_1$CTGTG$_1$CT-5' | | | |

TABLE 4E-continued

Immunomer Structure and Expression of BC from Human PBMC assay (24 hs)

| SEQ ID NO | Sequences and Modification (5'-3') | | |
|---|---|---|---|
| 31 | 5'-TG$_1$CTGTG$_1$CTTT-X-TTTCG$_1$TGTCG$_1$T-5' | | |
| 32 and 38 | 5'-TCG$_1$AACG$_1$TTCG$_1$-Y-GACAG$_1$CTGTCT-5' | | |
| 33 and 39 | 5'-TG$_1$CAACG$_1$CTTG$_1$C-Y-GACACG$_1$ TGTCT-5' | | |
| Media | | 9 | 10.3 | 11.1 |

| SEQ ID NO | Sequences and Modification (5'-3') | % CD69 1 µg/ml DN10 | % CD69 1 µg/ml DN11 | % CD69 1 µg/ml DN12 |
|---|---|---|---|---|
| 19 | 5'-TCG$_1$AACG$_2$TTCG$_1$-X-G$_1$CTTG$_2$CAAG$_1$CT-5' | | | |
| 20 | 5'-TCG$_1$AAC$_1$GTrCG$_1$-X-G$_1$CTTGC$_1$AAG$_1$CT-5' | | | |
| 21 and 34 | 5'-TCG$_1$AACG$_1$TTCG$_1$-Y-TCTTG$_1$CTGTCT-5' | 24 | 61.7 | |
| 22 and 35 | 5'-TCG$_1$AACG$_1$TTCG$_1$-Y-TCTTG$_2$CTGTCT-5' | 29.2 | 71.4 | 58 |
| 23 and 36 | 5'-TCG$_1$AACG$_1$TTCG$_1$-Y-TCTTGC$_1$TGTCT-5' | 35.7 | 60.5 | |
| 24 and 37 | 5'-TCGAACG$_1$TTCG$_1$-Y-TCTTCCACTCT-5' | 32.2 | 62.9 | |
| 25 and 34 | 5'-TG$_1$CAAG$_1$CTTG$_1$C-Y-TCTTG$_1$CTGTCT-5' | | | 23.6 |
| 26 and 37 | 5'-TG$_1$CAAG$_1$CTTG$_1$C-Y-TCTTCCACTCT-5' | | | 16.7 |
| 27 | 5'-TG$_1$CAAG$_1$CTTG$_1$C-X-CG$_1$TrCG$_1$AACG$_1$T-5' | | | |
| 28 | 5'-CTGTCG$_2$TTCTCo-X-oCTCTTG$_2$CTGTC-5' | 22.1 | 50 | 42.5 |
| 29 | 5'-CTGTCoG$_2$TTCTC-X-CTCTTG$_2$oCTGTC-5' | 31.5 | 70.5 | 54.4 |
| 30 | 5'-TCG$_1$TGTCG$_1$TTT-X-TTTG$_1$CTGTG$_1$CT-5' | 19.5 | | |
| 31 | 5'-TG$_1$CTGTG$_1$CTTT-X-TTTCG$_1$TGTCG$_1$T-5' | 15.5 | | |
| 32 and 38 | 5'-TCG$_1$AACG$_1$TTCG$_1$-Y-GACAG$_1$CTGTCT-5' | 40 | | |
| 33 and 39 | 5'-TG$_1$CAACG$_1$CTTG$_1$C-Y-GACACG$_1$ TGTCT-5' | 19.3 | | |
| Media | | 13.4 | 13.4 | 12.9 |

Normal phase represents a phosphorothioate linkage; o represents a phosphodiester linkage.
G$_1$ = 2'-deoxy-7-deazaguanosine
G$_2$ = Arabinoguanosine
C$_1$ = 1-(2'-deoxy-β-D-ribofuranosyl)-2-oxo-7-deaza-8-methylpurine
X = Glycerol Linker
Y = C3 Linker

TABLE 4F

Immunomer Structure and Expression of DC from Human PBMC assay (24 hs)

| SEQ ID NO | Sequences and Modification (5'-3') | % CD86 1 µg/ml DN1 | % CD86 1 µg/ml DN2 | % CD86 1 µg/ml DN3 |
|---|---|---|---|---|
| 19 | 5'-TCG$_1$AACG$_2$TTCG$_1$-X-G$_1$CTTG$_2$CAAG$_1$CT-5' | | | 11.9 |
| 20 | 5'-TCG$_1$AAC$_1$GTTCG$_1$-X-G$_1$CTTGC$_1$AAG$_1$CT-5' | | | 12.5 |
| 21 and 34 | 5'-TCG$_1$AACG$_1$TTCG$_1$-Y-TCTTG$_1$CTGTCT-5' | | | |
| 22 and 35 | 5'-TCG$_1$AACG$_1$TTCG$_1$-Y-TCTTG$_2$CTGTCT-5' | | | |
| 23 and 36 | 5'-TCG$_1$AACG$_1$TTCG$_1$-Y-TCTTGC$_1$TGTCT-5' | | | |
| 24 and 37 | 5'-TCG$_1$AACG$_1$TTCG$_1$-Y-TCTTCCACTCT-5' | | | |
| 25 and 34 | 5'-TG$_1$CAAG$_1$CTTG$_1$C-Y-TCTTG$_1$CTGTCT-5' | | | |

TABLE-continued

4F

Immunomer Structure and Expression of DC from Human PBMC assay (24 hs)

| SEQ ID NO | Sequences and Modification (5'-3') | | | |
|---|---|---|---|---|
| 26 and 37 | 5'-TG$_1$CAAG$_1$CTTG$_1$C-Y-TCTTCCACTCT-5' | | | |
| 27 | 5'-TG$_1$CAAG$_1$CTTG$_1$C-X-CG$_1$TTCG$_1$AACG$_1$T-5' | | | |
| 28 | 5'-CTGTCG$_2$TTCTCo-X-oCTCTTG$_2$CTGTC-5' | | | |
| 29 | 5'-CTGTCoG$_2$TTCTC-X-CTCTTG$_2$oCTGTC-5' | | | |
| 30 | 5'-TCG$_1$TGTCG$_1$TTT-X-TTTG$_1$CTGTG$_1$CT-5' | | | |
| 31 | 5'-TG$_1$CTGTG$_1$CTTT-X-TTTCG$_1$TGTCG$_1$T-5' | | | |
| 32 and 38 | 5'-TCG$_1$AACG$_1$TTCG$_1$-Y-GACAG$_1$CTGTCT-5' | | | |
| 33 and 39 | 5'-TG$_1$CAACG$_1$CTTG$_1$C-Y-GACACG$_1$ TGTCT-5' | | | |
| Media | | | | 13.7 |

| SEQ ID NO | Sequences and Modification (5'-3') | % CD86 1 μg/ml DN4 | % CD86 1 μg/ml DN5 | % CD86 1 μg/ml DN6 |
|---|---|---|---|---|
| 19 | 5'-TCG$_1$AACG$_2$TTCG$_1$-X-G$_1$CTTG$_2$CAAG$_1$CT-5' | | | |
| 20 | 5'-TCG$_1$AAC$_1$GTTCG$_1$-X-G$_1$CTTGC$_1$AAG$_1$CT-5' | | | |
| 21 and 34 | 5'-TCG$_1$AACG$_1$TTCG$_1$-Y-TCTTG$_1$CTGTCT-5' | | 54.7 | 68 |
| 22 and 35 | 5'-TCG$_1$AACG$_1$TTCG$_1$-Y-TCTTG$_2$CTGTCT-5' | | 58.8 | 75.3 |
| 23 and 36 | 5'-TCG$_1$AACG$_1$TTCG$_1$-Y-TCTTGC$_1$TGTCT-5' | 60.3 | 73.4 | |
| 24 and 37 | 5'-TCG$_1$AACG$_1$rTCG$_1$-Y-TCTTCCACTCT-5' | 51.8 | 61.1 | |
| 25 and 34 | 5'-TG$_1$CAAG$_1$CTTG$_1$C-Y-TCTTG$_1$CTGTCT-5 | | | |
| 26 and 37 | 5'-TG$_1$CAAG$_1$CTTG$_1$C-Y-TCTTCCACTCT-5' | | | |
| 27 | 5'-TG$_1$CAAG$_1$CTTG$_1$C-X-CG$_1$TTCG$_1$AACG$_1$T-5' | | | |
| 28 | 5'-CTGTCG$_2$TTCTCo-X-oCTCTTG$_2$CTGTC-5' | | | |
| 29 | 5'-CTGTCoG$_2$TTCTC-X-CTCTTG$_2$oCTGTC-5' | | | |
| 30 | 5'-TCG$_1$TGTCG$_1$TTT-X-TTTG$_1$CTGTG$_1$CT-5' | | | |
| 31 | 5'-TG$_1$CTGTG$_1$CTTT-X-TTTCG$_1$TGTCG$_1$T-5' | | | |
| 32 and 38 | 5'-TCG$_1$AACG$_1$TTCG$_1$-Y-GACAG$_1$CTGTCT-5' | | | |
| 33 and 39 | 5'-TG$_1$CAACG$_1$CTTG$_1$C-Y-GACACG$_1$ TGTCT-5' | | | |
| Media | | | 33.7 | 62.8 |

| SEQ ID NO | Sequences and Modification (5'-3') | % CD86 1 μg/ml DN7 | % CD86 1 μg/ml DN8 | % CD86 1 μg/ml DN9 |
|---|---|---|---|---|
| 19 | 5'-TCG$_1$AACG$_1$TTCG$_1$-X-G$_1$CTTG$_2$CAAG$_1$CT-5' | | | |
| 20 | 5'-TCG$_1$AAC$_1$GTTCG$_1$-X-G$_1$CTTGC$_1$AAG$_1$CT-5' | | | |
| 21 and 34 | 5'-TCG$_1$AACG$_1$TTCG$_1$-Y-TCTTG$_1$CTGTCT-5' | 45.4 | 88.7 | 78.3 |
| 22 and 35 | 5'-TCG$_1$AACG$_1$TTCG$_1$-Y-TCTTG$_2$CTGTCT-5' | 54.9 | 89.3 | 79.1 |
| 23 and 36 | 5'-TCG$_1$AACG$_1$TTCG$_1$-Y-TCTTGC$_1$TGTCT-5' | 55.3 | 88.6 | 79.9 |
| 24 and 37 | 5'-TCG$_1$AACG$_1$TTCG$_1$-Y-TCTTCCACTCT-5' | 47 | 85.7 | n/a |
| 25 and 34 | 5'-TG$_1$CAAGl CTTG$_1$C-Y-TCTTG$_1$CTGTCT-5' | | | |
| 26 and 37 | 5'-TG$_1$CAAG$_1$CTTG$_1$C-Y-TCTTCCACTCT-5' | | | |
| 27 | 5'-TG$_1$CAAG$_1$CTTG$_1$C-X-CG$_1$TTCG$_1$AACG$_1$T-5' | | | |
| 28 | 5'-CTGTCG$_2$TTCTCo-X-oCTCTTG$_2$CTGTC-5' | | 82.1 | |

TABLE-continued
4F

Immunomer Structure and Expression of DC from Human PBMC assay (24 hs)

| 29 | 5'-CTGTCoG$_2$TTCTC-X-CTCTTG$_2$oCTGTC-5' | | 89 | |
|---|---|---|---|---|
| 30 | 5'-TCG$_1$TGTCG$_1$TTT-X-TTTG$_1$CTGTG$_1$CT-5' | | | |
| 31 | 5'-TG$_1$CTGTG$_1$CTTT-X-TTTCGITGTCG$_1$T-5' | | | |
| 32 and 38 | 5'-TCG$_1$AACG$_1$TTCG$_1$-Y-GACAG$_1$CTGTCT-5' | | | |
| 33 and 39 | 5'-TG$_1$CAACG$_1$CTTG$_1$C-Y-GACACG$_1$ TGTCT-5' | | | |
| Media | | 47.5 | 56.1 | 53.2 |

| SEQ ID NO | Sequences and Modification (5'-3') | % CD86 1 µg/ml DN10 | % CD86 1 µg/ml DN11 | % CD86 1 µg/ml DN12 |
|---|---|---|---|---|
| 19 | 5'-TCG$_1$AACG$_2$TTCG$_1$-X-G$_1$CTTG$_2$CAAG$_1$CT-5' | | | |
| 20 | 5'-TCG$_1$AAC$_1$GTTCG$_1$-X-G$_1$CTTGC$_1$AAG$_1$CT-5' | | | |
| 21 and 34 | 5'-TCG$_1$AACG$_1$TTCG$_1$-Y-TCTTG$_1$CTGTCT-5' | 72 | 86.3 | |
| 22 and 35 | 5'-TCG$_1$AACG$_1$TTCG$_1$-Y-TCTTG$_2$CTGTCT-5' | 74.4 | 88.1 | 81.8 |
| 23 and 36 | 5'-TCG$_1$AACG$_1$TTCG$_1$-Y-TCTTGC$_1$TGTCT-5' | 77.1 | 87.5 | |
| 24 and 37 | 5'-TCG$_1$AACG$_1$TTCG$_1$-Y-TCTTCCACTCT-5' | 68.3 | 83.8 | |
| 25 and 34 | 5'-TG$_1$CAAG$_1$CTTG$_1$C-Y-TCTTG$_1$CTGTCT-5' | | | 60.4 |
| 26 and 37 | 5'-TG$_1$CAAG$_1$CTTG$_1$C-Y-TCTTCCACTCT-5' | | | 37.4 |
| 27 | 5'-TG$_1$CAAG$_1$CTTG$_1$C-X-CG$_1$TTCG$_1$AACG$_1$T-5' | | | |
| 28 | 5'-CTGTCG$_2$TTCTCo-X-oCTCTTG$_2$CTGTC-5' | 61.1 | 79.6 | 58.2 |
| 29 | 5'-CTGTCoG$_2$TTCTC-X-CTCTTG$_2$oCTGTC-5' | 68.2 | 87.3 | 69.5 |
| 30 | 5'-TCG$_1$TGTCG$_1$TTT-X-TTTG$_1$CTGTG$_1$CT-5' | | | 60.3 |
| 31 | 5'-TG$_1$CTGTG$_1$CTTT-X-TTTCG$_1$TGTCG$_1$T-5' | | | 44.7 |
| 32 and 38 | 5'-TCG$_1$AACG$_1$TTCG$_1$-Y-GACAG$_1$CTGTCT-5' | | | 65.8 |
| 33 and 39 | 5'-TG$_1$CAACG$_1$CTTG$_1$C-Y-GACACG$_1$ TGTCT-5' | | | 49.1 |
| Media | | 69.6 | 58.3 | 35.8 |

Normal phase represents a phosphorothioate linkage; o represents a phosphodiester linkage.
G$_1$ = 2'-deoxy-7-deazaguanosine
G$_2$ = Arabinoguanosine
C$_1$ = 1-(2'-deoxy-β-D-ribofuranosyl)-2-oxo-7-deaza-8-methylpurine
X = Glycerol Linker
Y = C3 Linker

Example 11

B Cell Proliferation Assay

A total of 1×10⁵ B cells/200 µl were stimulated with 0.3, 1.0, 3.0, or 10.0 µg/mL concentrations of immunomer compounds of the invention for 16 hr, then pulsed with 0.75 µCi of [$^3$H]-thymidine and harvested 8 h later. The incorporation of radioactivity was measured using liquid scintillation counter. Table 5 shows an average±SD of B cell proliferation at a final concentration of 1.0 µg/mL.

TABLE 5

Immunomer Structure and Immunostimulatory Activity in Human B-Cell Proliferation Assay (24 hs)

| SEQ ID NO | Sequences and Modification (5'-3') | [$^3$H]T (cpm) 1 µg/ml DN4 | [$^3$H]T (cpm) 1 µg/ml DN5 | [$^3$H]T (cpm) 1 µg/ml DN6 |
|---|---|---|---|---|
| 19 | 5'-TCG$_1$AACG$_2$TTCG$_1$-X-G$_1$CTTG$_2$CAAG$_1$CT-5' | | | |
| 20 | 5'-TCG$_1$AAC$_1$GTTCG$_1$-X-G$_1$CTTGC$_1$AAG$_1$CT-5' | | | |

TABLE 5-continued

Immunomer Structure and Immunostimulatory Activity in Human B-Cell Proliferation Assay (24 hs)

| SEQ ID NO | Sequences and Modification (5'-3') | | |
|---|---|---|---|
| 21 and 34 | 5'-TCG$_1$AACG$_1$TTCG$_1$-Y-TCTTG$_1$CTGTCT-5' | 31127 ± 6800 | 17626 ± 2809 |
| 22 and 35 | 5'-TCG$_1$AACG$_1$TTCG$_1$-Y-TCTTG$_2$CTGTCT-5' | 33368 ± 1364 | 17131 ± 1366 |
| 23 and 36 | 5'-TCG$_1$AACG$_1$TTCG$_1$-Y-TCTTGC$_1$TGTCT-5' | 30845 ± 2514 | 13826 ± 2331 |
| 24 and 37 | 5'-TCG$_1$AACG$_1$TTCG$_1$-Y-TCTTCCACTCT-5' | 34077 35 3636 | 8073 ± 583 |
| 25 and 34 | 5'-TG$_1$CAAG$_1$CTTG$_1$C-Y-TCTTG$_1$CTGTCT-5' | | |
| 26 and 37 | 5'-TG$_1$CAAGI CTTG$_1$C-Y-TCTTCCACTCT-5' | | |
| 27 | 5'-TG$_1$CAAG$_1$CTTG$_1$C-X-CG$_1$TTCG$_1$AACG$_1$T-5' | | |
| 28 | 5'-CTGTCG$_2$TTCTCo-X-oCTCTTG$_2$CTGTC-5' | | |
| 29 | 5'-CTGTCoG$_2$TTCTC-X-CTCTTG$_2$oCTGTC-5' | | |
| 30 | 5'-TCG$_1$TGTCG$_1$TTT-X-TTTG$_1$CTGTG$_1$CT-5' | | |
| 31 | 5'-TG$_1$CTGTG$_1$CTTT-X-TTTCG$_1$TGTCG$_1$T-5' | | |
| 32 and 38 | 5'-TCG$_1$AACG$_1$TTCG$_1$-Y-GACAG$_1$CTGTCT-5' | | |
| 33 and 39 | 5'-TG$_1$CAACG$_1$CTTG$_1$C-Y-GACACG$_1$ TGTCT-5' | | |
| Media | | 646 ± 236 | 457 ± 121 |

| SEQ ID NO | Sequences and Modification (5'-3') | [³H]T (cpm) 1 µg/ml DN7 | [³H]T (cpm) 1 µg/ml DN8 | [³H]T (cpm) 1 µg/ml DN9 |
|---|---|---|---|---|
| 19 | 5'-TCG$_1$AACG$_2$TTCG$_1$-X-G$_1$CTTG$_2$CAAG$_1$CT-5' | | | |
| 20 | 5'-TCG$_1$AAC$_1$GTTCG$_1$-X-G$_1$CTTGC$_1$AAG$_1$CT-5' | | | |
| 21 and 34 | 5'-TCG$_1$AACG$_1$TTCG$_1$-Y-TCTTG$_1$CTGTCT-5' | 37731 ± 2901 | | |
| 22 and 35 | 5'-TCG$_1$AACG$_1$TTCG$_1$-Y-TCTTG$_2$CTGTCT-5' | 38405 ± 8056 | | |
| 23 and 36 | 5'-TCG$_1$AACG$_1$TTCG$_1$-Y-TCTTGC$_1$TGTCT-5' | 34702 ± 6196 | | |
| 24 and 37 | 5'-TCG$_1$AACG$_1$TTCG$_1$-Y-TCTTCCACTCT-5' | 23030 ± 1941 | | |
| 25 and 34 | 5'-TG$_1$CAAG$_1$CTTG$_1$C-Y-TCTTG$_1$CTGTCT-5' | | | |
| 26 and 37 | 5'-TG$_1$CAAG$_1$CTTG$_1$C-Y-TCTTCCACTCT-5' | | | |
| 27 | 5'-TG$_1$CAAG$_1$CTTG$_1$C-X-CG$_1$TTCG$_1$AACG$_1$T-5' | | | |
| 28 | 5'-CTGTCG$_2$TTCTCo-X-oCTCTTG$_2$CTGTC-5' | | | |
| 29 | 5'-CTGTCoG$_2$TTCTC-X-CTCTTG$_2$oCTGTC-5' | | | |
| 30 | 5'-TCG$_1$TGTCG$_1$TTT-X-TTTG$_1$CTGTG$_1$CT-5' | | | |
| 31 | 5'-TG$_1$CTGTG$_1$CTTT-X-TTTCG$_1$TGTCG$_1$T-5' | | | |
| 32 and 38 | 5'-TCG$_1$AACG$_1$TTCG$_1$-Y-GACAG$_1$CTGTCT-5' | | | |
| 33 and 39 | 5'-TG$_1$CAACG$_1$CTTG$_1$C-Y-GACACG$_1$ TGTCT-5' | | | |
| Media | | 658 ± 205 | | |

Normal phase represents a phosphorothioate linkage; o represents a phosphodiester linkage.
G$_1$ = 2'-deoxy-7-deazaguanosine
G$_2$ = Arabinoguanosine
C$_1$ = 1-(2'-deoxy-β-D-ribofuranosyl)-2-oxo-7-deaza-8-methylpurine
X = Glycerol Linker
Y = C3 Linker

Equivalents

While the foregoing invention has been described in some detail for purposes of clarity and understanding, it will be appreciated by one skilled in the art from a reading of this disclosure that various changes in form and detail can be made without departing from the true scope of the invention and appended claims.

What is claimed is:

1. An immunostimulatory oligonucleotide having the structure 5'-TCG$_1$AACG$_1$TTCG$_1$-Y-TCTTG$_2$CTGTCT-5'; wherein Y is a glycerol linker, G$_1$ is 2'-deoxy-7-deazaguanosine and G$_2$ is arabinoguanosine.

2. A composition comprising the oligonucleotide according to claim 1 and a physiologically acceptable carrier.

3. A method for generating an immune response in a vertebrate, the method comprising administering to the vertebrate an immunostimulatory oligonucleotide having the structure 5'-TCG$_1$AACG$_1$TTCG$_1$-Y-TCTTG$_2$CTGTCT-5'; wherein Y is a glycerol linker, G$_1$ is 2'-deoxy-7-deazaguanosine and G$_2$ is arabinoguanosine.

4. The method according to claim 3, wherein the route of administration is selected from parenteral, oral, sublingual, transdermal, topical, intranasal, aerosol, intraocular, intratracheal, intrarectal, vaginal, gene gun, dermal patch, eye drop and mouthwash.

5. The oligonucleotide according to claim 1, further comprising an antibody, antisense oligonucleotide, protein, antigen, allergen, chemotherapeutic agent or adjuvant.

6. The composition according to claim 2, further comprising an antibody, antisense oligonucleotide, protein, antigen, allergen, chemotherapeutic agent or adjuvant.

7. The method according to claim 3, further comprising administering an antibody, antisense oligonucleotide, protein, antigen, allergen, chemotherapeutic agent or adjuvant.

* * * * *

UNITED STATES PATENT AND TRADEMARK OFFICE
CERTIFICATE OF CORRECTION

PATENT NO. : 7,498,425 B2  Page 1 of 1
APPLICATION NO. : 11/174448
DATED : March 3, 2009
INVENTOR(S) : Agrawal et al.

It is certified that error appears in the above-identified patent and that said Letters Patent is hereby corrected as shown below:

Claim 1, column 89, line 62, please delete the text "Y is a glycerol linker" and insert the following text --Y is a C3-linker--

Claim 3, column 90, line 61, please delete the text "Y is a glycerol linker" and insert the following text --Y is a C3-linker--

Signed and Sealed this

Thirtieth Day of June, 2009

JOHN DOLL
*Acting Director of the United States Patent and Trademark Office*

UNITED STATES PATENT AND TRADEMARK OFFICE
CERTIFICATE OF CORRECTION

| | | |
|---|---|---|
| PATENT NO. | : 7,498,425 B2 | Page 1 of 1 |
| APPLICATION NO. | : 11/174448 | |
| DATED | : March 3, 2009 | |
| INVENTOR(S) | : Sudhir Agrawal et al. | |

It is certified that error appears in the above-identified patent and that said Letters Patent is hereby corrected as shown below:

Title Page, (*) Notice: Subject to any disclaimer, the term of this patent is extended or adjusted under 35 U.S.C. 154(b) by 385 days.

should read (*) Notice: Subject to any disclaimer, the term of this patent is extended or adjusted under 35 U.S.C. 154(b) by 630 days.

Signed and Sealed this

Twentieth Day of April, 2010

David J. Kappos
*Director of the United States Patent and Trademark Office*

```
                               SEQUENCE LISTING

<160> NUMBER OF SEQ ID NOS: 41

<210> SEQ ID NO 1
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)
<223> OTHER INFORMATION: 2'-deoxy-7-deazaguanosine
<220> FEATURE:
<221> NAME/KEY: modified_base
<222> LOCATION: (7)
<223> OTHER INFORMATION: 2'-deoxy-7-deazaguanosine
<220> FEATURE:
<221> NAME/KEY: modified_base
<222> LOCATION: (11)
<223> OTHER INFORMATION: 2'-deoxy-7-deazaguanosine

<400> SEQUENCE: 1
tcnaacnttc n                                                          11

<210> SEQ ID NO 2
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)
<223> OTHER INFORMATION: 2'-deoxy-7-deazaguanosine
<220> FEATURE:
<221> NAME/KEY: modified_base
<222> LOCATION: (7)
<223> OTHER INFORMATION: 2'-deoxy-7-deazaguanosine

<400> SEQUENCE: 2
tcnaacnttc g                                                          11

<210> SEQ ID NO 3
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
tctcaccttc t                                                          11

<210> SEQ ID NO 4
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
```

```
<222> LOCATION: (3)
<223> OTHER INFORMATION: Arabinoguanosine
<220> FEATURE:
<221> NAME/KEY: modified_base
<222> LOCATION: (7)
<223> OTHER INFORMATION: Arabinoguanosine
<220> FEATURE:
<221> NAME/KEY: modified_base
<222> LOCATION: (11)
<223> OTHER INFORMATION: Arabinoguanosine

<400> SEQUENCE: 4
tcnaacnttc n                                                           11

<210> SEQ ID NO 5
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)
<223> OTHER INFORMATION: Arabinoguanosine
<220> FEATURE:
<221> NAME/KEY: modified_base
<222> LOCATION: (7)
<223> OTHER INFORMATION: Arabinoguanosine

<400> SEQUENCE: 5
tcnaacnttc g                                                           11

<210> SEQ ID NO 6
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)
<223> OTHER INFORMATION: 2'-deoxy-7-deazaguanosine
<220> FEATURE:
<221> NAME/KEY: modified_base
<222> LOCATION: (6)
<223> OTHER INFORMATION: 2'-deoxy-7-deazaguanosine
<220> FEATURE:
<221> NAME/KEY: modified_base
<222> LOCATION: (10)
<223> OTHER INFORMATION: 2'-deoxy-7-deazaguanosine
<220> FEATURE:
<221> NAME/KEY: modified_base
<222> LOCATION: (14)
<223> OTHER INFORMATION: 2'-deoxy-7-deazaguanosine

<400> SEQUENCE: 6
tcntcnaacn ttcnagatga t                                                21

<210> SEQ ID NO 7
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)
<223> OTHER INFORMATION: Arabinoguanosine
<220> FEATURE:
<221> NAME/KEY: modified_base
```

```
<222> LOCATION: (6)
<223> OTHER INFORMATION: Arabinoguanosine
<220> FEATURE:
<221> NAME/KEY: modified_base
<222> LOCATION: (10)
<223> OTHER INFORMATION: Arabinoguanosine
<220> FEATURE:
<221> NAME/KEY: modified_base
<222> LOCATION: (14)
<223> OTHER INFORMATION: Arabinoguanosine

<400> SEQUENCE: 7
tcntcnaacn ttcnagatga t                                              21

<210> SEQ ID NO 8
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)
<223> OTHER INFORMATION: 2'-deoxyinosine
<220> FEATURE:
<221> NAME/KEY: modified_base
<222> LOCATION: (6)
<223> OTHER INFORMATION: 2'-deoxyinosine
<220> FEATURE:
<221> NAME/KEY: modified_base
<222> LOCATION: (10)
<223> OTHER INFORMATION: 2'-deoxyinosine
<220> FEATURE:
<221> NAME/KEY: modified_base
<222> LOCATION: (14)
<223> OTHER INFORMATION: 2'-deoxyinosine

<400> SEQUENCE: 8
tcntcnaacn ttcnagatga t                                              21

<210> SEQ ID NO 9
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (2)
<223> OTHER INFORMATION: 1-(2'-deoxy-beta-D-ribofuranosyl)-2-oxo-7-
      deaza-8-methylpurine
<220> FEATURE:
<221> NAME/KEY: modified_base
<222> LOCATION: (5)
<223> OTHER INFORMATION: 1-(2'-deoxy-beta-D-ribofuranosyl)-2-oxo-7-
      deaza-8-methylpurine
<220> FEATURE:
<221> NAME/KEY: modified_base
<222> LOCATION: (9)
<223> OTHER INFORMATION: 1-(2'-deoxy-beta-D-ribofuranosyl)-2-oxo-7-
      deaza-8-methylpurine
<220> FEATURE:
<221> NAME/KEY: modified_base
<222> LOCATION: (13)
<223> OTHER INFORMATION: 1-(2'-deoxy-beta-D-ribofuranosyl)-2-oxo-7-
      deaza-8-methylpurine

<400> SEQUENCE: 9
tngtngaang ttngagatga t                                              21

<210> SEQ ID NO 10
```

```
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (2)
<223> OTHER INFORMATION: Arabinocytidine
<220> FEATURE:
<221> NAME/KEY: modified_base
<222> LOCATION: (5)
<223> OTHER INFORMATION: Arabinocytidine
<220> FEATURE:
<221> NAME/KEY: modified_base
<222> LOCATION: (9)
<223> OTHER INFORMATION: Arabinocytidine
<220> FEATURE:
<221> NAME/KEY: modified_base
<222> LOCATION: (13)
<223> OTHER INFORMATION: Arabinocytidine

<400> SEQUENCE: 10
tngtngaang ttngagatga t                                              21

<210> SEQ ID NO 11
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (2)
<223> OTHER INFORMATION: 2'-deoxy-5-hydroxycytidine
<220> FEATURE:
<221> NAME/KEY: modified_base
<222> LOCATION: (5)
<223> OTHER INFORMATION: 2'-deoxy-5-hydroxycytidine
<220> FEATURE:
<221> NAME/KEY: modified_base
<222> LOCATION: (9)
<223> OTHER INFORMATION: 2'-deoxy-5-hydroxycytidine
<220> FEATURE:
<221> NAME/KEY: modified_base
<222> LOCATION: (13)
<223> OTHER INFORMATION: 2'-deoxy-5-hydroxycytidine

<400> SEQUENCE: 11
tngtngaang ttngagatga t                                              21

<210> SEQ ID NO 12
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)
<223> OTHER INFORMATION: 2'-deoxy-7-deazaguanosine
<220> FEATURE:
<221> NAME/KEY: modified_base
<222> LOCATION: (7)
<223> OTHER INFORMATION: 2'-deoxy-7-deazaguanosine

<400> SEQUENCE: 12 tcnaacnttc                                                           10

<210> SEQ ID NO 13
```

```
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)
<223> OTHER INFORMATION: 2'-deoxy-7-deazaguanosine
<220> FEATURE:
<221> NAME/KEY: modified_base
<222> LOCATION: (7)
<223> OTHER INFORMATION: 2'-deoxy-7-deazaguanosine
<220> FEATURE:
<221> NAME/KEY: modified_base
<222> LOCATION: (11)
<223> OTHER INFORMATION: 2'-deoxy-7-deazaguanosine

<400> SEQUENCE: 13
tcnttcnaac n                                                              11

<210> SEQ ID NO 14
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14
tccaaccttc g                                                              11

<210> SEQ ID NO 15
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)
<223> OTHER INFORMATION: 2'-deoxy-7-deazaguanosine
<220> FEATURE:
<221> NAME/KEY: modified_base
<222> LOCATION: (6)
<223> OTHER INFORMATION: 2'-deoxy-7-deazaguanosine
<220> FEATURE:
<221> NAME/KEY: modified_base
<222> LOCATION: (11)
<223> OTHER INFORMATION: 2'-deoxy-7-deazaguanosine

<400> SEQUENCE: 15
tcnttncaac n                                                              11

<210> SEQ ID NO 16
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)
<223> OTHER INFORMATION: Arabinoguanosine
<220> FEATURE:
<221> NAME/KEY: modified_base
<222> LOCATION: (7)
<223> OTHER INFORMATION: Arabinoguanosine

<400> SEQUENCE: 16
```

```
tcnaacnttc t                                              11

<210> SEQ ID NO 17
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)
<223> OTHER INFORMATION: 2'-deoxy-7-deazaguanosine
<220> FEATURE:
<221> NAME/KEY: modified_base
<222> LOCATION: (7)
<223> OTHER INFORMATION: Arabinoguanosine
<220> FEATURE:
<221> NAME/KEY: modified_base
<222> LOCATION: (11)
<223> OTHER INFORMATION: 2'-deoxy-7-deazaguanosine

<400> SEQUENCE: 17
tcnaacnttc n                                              11

<210> SEQ ID NO 18
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)
<223> OTHER INFORMATION: 2'-deoxy-7-deazaguanosine
<220> FEATURE:
<221> NAME/KEY: modified_base
<222> LOCATION: (6)
<223> OTHER INFORMATION: 1-(2'-deoxy-beta-D-ribofuranosyl)-2-oxo-7-
      deaza-8-methylpurine
<220> FEATURE:
<221> NAME/KEY: modified_base
<222> LOCATION: (11)
<223> OTHER INFORMATION: 2'-deoxy-7-deazaguanosine

<400> SEQUENCE: 18
tcnaangttc n                                              11

<210> SEQ ID NO 19
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)
<223> OTHER INFORMATION: 2'-deoxy-7-deazaguanosine
<220> FEATURE:
<221> NAME/KEY: modified_base
<222> LOCATION: (7)
<223> OTHER INFORMATION: Arabinoguanosine
<220> FEATURE:
<221> NAME/KEY: modified_base
<222> LOCATION: (11)
<223> OTHER INFORMATION: 2'-deoxy-7-deazaguanosine

<400> SEQUENCE: 19
tcnaacnttc n                                              11
```

```
<210> SEQ ID NO 20
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)
<223> OTHER INFORMATION: 2'-deoxy-7-deazaguanosine
<220> FEATURE:
<221> NAME/KEY: modified_base
<222> LOCATION: (6)
<223> OTHER INFORMATION: 1-(2'-deoxy-beta-D-ribofuranosyl)-2-oxo-7-
      deaza-8-methylpurine
<220> FEATURE:
<221> NAME/KEY: modified_base
<222> LOCATION: (11)
<223> OTHER INFORMATION: 2'-deoxy-7-deazaguanosine

<400> SEQUENCE: 20
tcnaangttc n                                                          11

<210> SEQ ID NO 21
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)
<223> OTHER INFORMATION: 2'-deoxy-7-deazaguanosine
<220> FEATURE:
<221> NAME/KEY: modified_base
<222> LOCATION: (7)
<223> OTHER INFORMATION: 2'-deoxy-7-deazaguanosine
<220> FEATURE:
<221> NAME/KEY: modified_base
<222> LOCATION: (11)
<223> OTHER INFORMATION: 2'-deoxy-7-deazaguanosine

<400> SEQUENCE: 21
tcnaacnttc n                                                          11

<210> SEQ ID NO 22
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)
<223> OTHER INFORMATION: 2'-deoxy-7-deazaguanosine
<220> FEATURE:
<221> NAME/KEY: modified_base
<222> LOCATION: (7)
<223> OTHER INFORMATION: 2'-deoxy-7-deazaguanosine
<220> FEATURE:
<221> NAME/KEY: modified_base
<222> LOCATION: (11)
<223> OTHER INFORMATION: 2'-deoxy-7-deazaguanosine

<400> SEQUENCE: 22
tcnaacnttc n                                                          11

<210> SEQ ID NO 23
<211> LENGTH: 11
```

```
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)
<223> OTHER INFORMATION: 2'-deoxy-7-deazaguanosine
<220> FEATURE:
<221> NAME/KEY: modified_base
<222> LOCATION: (7)
<223> OTHER INFORMATION: 2'-deoxy-7-deazaguanosine
<220> FEATURE:
<221> NAME/KEY: modified_base
<222> LOCATION: (11)
<223> OTHER INFORMATION: 2'-deoxy-7-deazaguanosine

<400> SEQUENCE: 23
tcnaacnttc n                                                            11

<210> SEQ ID NO 24
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)
<223> OTHER INFORMATION: 2'-deoxy-7-deazaguanosine
<220> FEATURE:
<221> NAME/KEY: modified_base
<222> LOCATION: (7)
<223> OTHER INFORMATION: 2'-deoxy-7-deazaguanosine
<220> FEATURE:
<221> NAME/KEY: modified_base
<222> LOCATION: (11)
<223> OTHER INFORMATION: 2'-deoxy-7-deazaguanosine

<400> SEQUENCE: 24
tcnaacnttc n                                                            11

<210> SEQ ID NO 25
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (2)
<223> OTHER INFORMATION: 2'-deoxy-7-deazaguanosine
<220> FEATURE:
<221> NAME/KEY: modified_base
<222> LOCATION: (6)
<223> OTHER INFORMATION: 2'-deoxy-7-deazaguanosine
<220> FEATURE:
<221> NAME/KEY: modified_base
<222> LOCATION: (10)
<223> OTHER INFORMATION: 2'-deoxy-7-deazaguanosine

<400> SEQUENCE: 25
tncaancttn c                                                            11

<210> SEQ ID NO 26
<211> LENGTH: 11
<212> TYPE: DNA
<213> ORGANISM: Artificial Sequence
<220> FEATURE:
<223> OTHER INFORMATION: Description of Artificial Sequence: Synthetic
``` oligonucleotide
<220> FEATURE:
<221> NAME/KEY: modified_base
<222> LOCATION: (2)
<223> OTHER INFORMATION: 2'-deoxy-7-deazaguanosine
<220> FEATURE:
<221> NAME/KEY: modified_base
<222> LOCATION: (6)
<223> OTHER INFORMATION: 2'-deoxy-7-deazaguanosine
<220> FEATURE:
<221> NAME/KEY: modified_base
<222> LOCATION: (10)
<223> OTHER INFORMATION: 2'-deoxy-7-deazaguanosine

<400> SEQUENCE: 26
tncaancttn c                                                              11

<210> SEQ ID NO 27
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (2)
<223> OTHER INFORMATION: 2'-deoxy-7-deazaguanosine
<220> FEATURE:
<221> NAME/KEY: modified_base
<222> LOCATION: (6)
<223> OTHER INFORMATION: 2'-deoxy-7-deazaguanosine
<220> FEATURE:
<221> NAME/KEY: modified_base
<222> LOCATION: (10)
<223> OTHER INFORMATION: 2'-deoxy-7-deazaguanosine

<400> SEQUENCE: 27
tncaancttn c                                                              11

<210> SEQ ID NO 28
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (6)
<223> OTHER INFORMATION: Arabinoguanosine

<400> SEQUENCE: 28
ctgtcnttct c                                                              11

<210> SEQ ID NO 29
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (6)
<223> OTHER INFORMATION: Arabinoguanosine

<400> SEQUENCE: 29
ctgtcnttct c                                                              11

<210> SEQ ID NO 30

```
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)
<223> OTHER INFORMATION: 2'-deoxy-7-deazaguanosine
<220> FEATURE:
<221> NAME/KEY: modified_base
<222> LOCATION: (8)
<223> OTHER INFORMATION: 2'-deoxy-7-deazaguanosine

<400> SEQUENCE: 30
tcntgtcntt t                                                           11

<210> SEQ ID NO 31
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (2)
<223> OTHER INFORMATION: 2'-deoxy-7-deazaguanosine
<220> FEATURE:
<221> NAME/KEY: modified_base
<222> LOCATION: (7)
<223> OTHER INFORMATION: 2'-deoxy-7-deazaguanosine

<400> SEQUENCE: 31
tnctgtnctt t                                                           11

<210> SEQ ID NO 32
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)
<223> OTHER INFORMATION: 2'-deoxy-7-deazaguanosine
<220> FEATURE:
<221> NAME/KEY: modified_base
<222> LOCATION: (7)
<223> OTHER INFORMATION: 2'-deoxy-7-deazaguanosine
<220> FEATURE:
<221> NAME/KEY: modified_base
<222> LOCATION: (11)
<223> OTHER INFORMATION: 2'-deoxy-7-deazaguanosine

<400> SEQUENCE: 32
tcnaacnttc n                                                           11

<210> SEQ ID NO 33
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (2)
<223> OTHER INFORMATION: 2'-deoxy-7-deazaguanosine
```

```
<220> FEATURE:
<221> NAME/KEY: modified_base
<222> LOCATION: (7)
<223> OTHER INFORMATION: 2'-deoxy-7-deazaguanosine
<220> FEATURE:
<221> NAME/KEY: modified_base
<222> LOCATION: (11)
<223> OTHER INFORMATION: 2'-deoxy-7-deazaguanosine

<400> SEQUENCE: 33
tncaacnctt nc                                                              12

<210> SEQ ID NO 34
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)
<223> OTHER INFORMATION: 2'-deoxy-7-deazaguanosine

<400> SEQUENCE: 34
tctgtcnttc t                                                               11

<210> SEQ ID NO 35
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)
<223> OTHER INFORMATION: Arabinoguanosine

<400> SEQUENCE: 35
tctgtcnttc t                                                               11

<210> SEQ ID NO 36
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (6)
<223> OTHER INFORMATION: 1-(2'-deoxy-beta-D-ribofuranosyl)-2-oxo-7-
      deaza-8-methylpurine

<400> SEQUENCE: 36
tctgtngttc t                                                               11

<210> SEQ ID NO 37
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 37
tctcaccttc t                                                               11
```

```
<210> SEQ ID NO 38
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)
<223> OTHER INFORMATION: 2'-deoxy-7-deazaguanosine

<400> SEQUENCE: 38
tctgtcnaca g                                                         11

<210> SEQ ID NO 39
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (6)
<223> OTHER INFORMATION: 2'-deoxy-7-deazaguanosine

<400> SEQUENCE: 39
tctgtncaca g                                                         11

<210> SEQ ID NO 40
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)
<223> OTHER INFORMATION: 2'-deoxy-7-deazaguanosine
<220> FEATURE:
<221> NAME/KEY: modified_base
<222> LOCATION: (7)
<223> OTHER INFORMATION: 2'-deoxy-7-deazaguanosine

<400> SEQUENCE: 40
tcnaacnttc t                                                         11

<210> SEQ ID NO 41
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 41
tcgaacgttc g                                                         11
```